US007160708B2

(12) United States Patent
Eirich et al.

(10) Patent No.: US 7,160,708 B2
(45) Date of Patent: Jan. 9, 2007

(54) **FATTY ALCOHOL OXIDASE GENES AND PROTEINS FROM *CANDIDA TROPICALIS* AND METHODS RELATING THERETO**

(75) Inventors: L. Dudley Eirich, Milford, OH (US); David L. Craft, Fort Thomas, KY (US)

(73) Assignee: Cognis Corporation, Ambler, PA (US)

( * ) Notice: Subject to any disclaimer, the term of this patent is extended or adjusted under 35 U.S.C. 154(b) by 401 days.

(21) Appl. No.: 10/418,819

(22) Filed: Apr. 18, 2003

(65) Prior Publication Data

US 2003/0224493 A1 Dec. 4, 2003

Related U.S. Application Data

(60) Provisional application No. 60/374,021, filed on Apr. 19, 2002.

(51) Int. Cl.

| | |
|---|---|
| ***C12N 9/02*** | (2006.01) |
| ***C12N 15/00*** | (2006.01) |
| ***C12N 1/20*** | (2006.01) |
| ***C12P 21/04*** | (2006.01) |
| ***C12Q 1/00*** | (2006.01) |
| ***C12Q 1/34*** | (2006.01) |
| ***C07H 21/04*** | (2006.01) |
| *C12Q 1/26* | (2006.01) |
| *C12Q 1/68* | (2006.01) |

(52) U.S. Cl. .............................. 435/189; 435/4; 435/6; 435/18; 435/25; 435/252.3; 435/320.1; 435/440; 435/69.1; 435/71.1; 536/23.2; 536/23.7

(58) Field of Classification Search ................ 435/189, 435/4, 6, 252.3, 320.1, 69.1, 71.1, 440, 18, 435/25; 536/23.2, 23.7
See application file for complete search history.

(56) References Cited

U.S. PATENT DOCUMENTS

| | | | |
|---|---|---|---|
| 4,136,094 | A | 1/1979 | Condie |
| 5,426,045 | A | 6/1995 | Sawyer et al. |
| 5,443,984 | A | 8/1995 | Sawyer et al. |
| 6,007,811 | A | 12/1999 | Sawyer et al. |
| 6,331,420 | B1 | 12/2001 | Wilson et al. |

FOREIGN PATENT DOCUMENTS

| | | |
|---|---|---|
| WO | WO 99/47685 | 9/1999 |

OTHER PUBLICATIONS

Slabas et al. Sequence Alignment.*
Blasig et al. (1988) "Degradation of long-chain n-alkanes by the yeast *Candida maltosa*", *Appl. Microbiol. Biotechnol.*, 28:589-597.

(Continued)

*Primary Examiner*—Tekchand Saidha
*Assistant Examiner*—Yong D. Pak
(74) *Attorney, Agent, or Firm*—John F. Daniels

(57) ABSTRACT

The present invention provides fatty alcohol oxidase (FAO) proteins and nucleic acid molecules encoding the FAO proteins. Also provided are analogs, derivatives, and enzymatically active fragments of the FAO proteins. Vectors and host cells comprising the nucleic acid molecules encoding the FAO proteins, analogs, derivatives and enzymatically active fragments thereof are also provided. In addition, FAO signature peptides and isolated nucleic acid molecules encoding the signature peptides are provided by the present invention. Methods of producing or increasing production of a subject FAO protein, methods for increasing aldehyde production during the second step of the ω-oxidation pathway of fatty acids, methods for increasing production of a ketone from an alcohol during the second step of the ω-oxidation pathway of fatty acids, and methods for increasing production of a dicarboxylic acid are also provided.

36 Claims, 10 Drawing Sheets

OTHER PUBLICATIONS

Dickinson et al. (1992) "Purification and some properties of alcohol oxidase from alkane-grown *Candida tropicalis*", *Biochem. J.*, 282:325-331.

Hommel et al. (1994) "The inducible microsomal fatty alcohol oxidase of *Candida* (*Torulopsis*) *apicola*", *Appl. Microbiol. Biotechnol*, 40:729-734.

Hommel et al. (1990) "Evidence for two fatty alcohol oxidases in the biosurfactant-producing yeast *Candida* (*Torulopsis*) *bombicola*" *FEMS Microbiology Letters*, 70:183-186.

Ilchenko et al. (1998) "Isolation and characterization of alcohol oxidase from higher alcohols of the yeast *Torulopsis candida* grown on hexadecane", *Biokhimiya* 53:263-271.

Kemp et al. (1990) "Light sensitivity of the n-alkane-induced fatty alcohol oxidase from *Candida tropicalis* and *Yarrowia lipolytica*" *Appl. Microbiol. Biotechnol.*, 32:461-464.

Kemp et al. (1988) "Inducible long chain alcohol oxidase from alkane-grown *Candida tropicalis*", *Appl. Microbiol. Biotechnol.*, 29:370-374.

Kemp et al. (1991) "Activity and substrate specificity of the fatty alcohol oxidase of *Candida tropicalis* in organic solvents", *Appl. Microbiol. Biotechnol.*, 34:441-445.

Mauersberger et al. (1992) "Substrate specificity and stereoselectivity of fatty alcohol oxidase from the yeast *Candida maltosa*", *Appl. Microbiol. Biotechnol.*, 37:66-73.

Vanhanen et al. (2000) "A Consensus Sequence for Long-chain Fatty-acid Alcohol Oxidases from *Candida* Identifies a Family of Genes Involved in Lipid ω-Oxidation in Yeast with Homologues in Plants and Bacteria", *The Journal of Biological Chemistry*, 275(6):4445-4452.

Babin et al.; Plasma Lipoproteins in Fish; Journal of Lipid Research; 1989; pp. 467-489; vol. 30; France.

Silver et al.; Preparation and Use of Fibrin Glue in Surgery; Biomaterials; 1995; pp. 891-903; vol. 16, No. 12; Butterworth Heinemann; Great Britain.

Hewlett; Strategies for Optimising Serum-Free Media; Cryotechnology; 1991; pp. 3-14; vol. 5; Kuwer Acedemic Publishers; Netherlands.

DeKoning et al.; Mitogenesis of Rainbow Trout Peripheral Blood Lymphocytes Requires Homologous Plasma for Optimal Resp.; In Vitro Cell Dev. Biol.; May 1991; pp. 381-386;vol. 27A.

Doolittle; The Evolution of the Vertebrate Plasma Proteins; Biol. Bull.; Jun. 1987; vol. 172; pp. 269-283.

Cohn et al.; Preparation and Properties of Serum and Plasma Proteins; Separation into Fractions of Protein and Lipoprotein Components; Mar. 1946; pp. 459-475.

Ngai et al.; A Novel One-Step Purification of Human a-Thrombin After Direct Activation of Crude Prothrombin Enriched from Plasma; Biochem. J.; 1991; pp. 805-808; Great Britain.

Denovan-Wright et al.; Nucleotide Seq. of Transferrin cDNAs and Tissue-Spec. Expr. of the Transferrin Gene in Atl. Cod; Comp. Bioch. Phys.;vol. 113B; No. 2; 1996; pp. 269-273.

Schense et al.; Enzymatic Incorporation of Bioactive Peptides into Fibrin Matrices Enhances Neurite Extension; Nature Biotechnology; vol. 18; Apr. 2000; pp. 415-419.

Durham; Aggregation of Intermediate Filaments by 2,5-Hexanedione; Journal of Neuropathology and Experimental Neurology; vol. 47; No. 4; Jul. 1998; pp. 432-442.

Ando; Adsorption of Serum Lipoproteins from Rainbow Trout to Dextran Sulfate Cellulose; Fisheries Science; vol. 62(3); pp. 410-415; 1996.

Summerfelt et al.; Anesthesia, Surgery, and Related Techniques; Methods for Fish Biology; Chapter 8; 1990; American Fisheries Society; pp. 213-218; USA.

Davidson et al.; Identification and Purification of Serum Albumin from Rainbow Trout; Comp. Biochem. Physiol.; vol. 93B, No. 1; 1989; pp. 5-9; Pergamon Press; Great Britain.

Beattie et al.; A Novel Approach to Increase Human Islet Call MAss While Preserving Beta-Cell Function . Diabetes Dec. 2002; vol. 51, No. 12; pp. 3435-3439.

Flanagan et al.; Neurite Branching on Deformable Substrates; Neuroreport; Dec. 20, 2002; vol. 13, No. 18; pp. 2411-2415.

Ivanova et al.; A Stem Cell Molecular Signature; Science; Oct. 18, 2002; vol. 298, No. 5593; pp. 601-604.

Ramalho-Santos et al.; "Stemness": Transcriptional Profiling of Embryonic and Adult Stem Cells; Science; Oct. 18, 2002; vol. 298, No. 5593; pp. 597-600.

* cited by examiner

FATTY ALCOHOL OXIDASE GENES AND PROTEINS FROM *CANDIDA TROPICALIS* AND METHODS RELATING THERETO

CROSS-REFERENCE TO RELATED APPLICATIONS

The present invention claims benefit of U.S. Provisional Application Ser. No. 60/374,021, filed Apr. 19, 2002, which application is incorporated by reference herein.

STATEMENT REGARDING FEDERALLY SPONSORED RESEARCH OR DEVELOPMENT

This invention was funded, at least in part, under a grant from the Department of Commerce, NIST-ATP Cooperative Agreement Number 70NANB8H4033. The Government may therefore have certain fights in the invention.

BACKGROUND OF THE INVENTION

Several genetically engineered strains of *Candida tropicalis* have been used in fermentations for the bioconversion of the 18-carbon fatty acid known as oleic acid to 18-carbon dicarboxylic acid. When grown on fatty acids, wild-type *C. tropicalis* converts long chain fatty acids to acetyl CoA by a process known as β-oxidation, which is the sequential catabolism of 2-carbon length fragments of a fatty acid to acetyl CoA. β-Oxidation is thus named because the initial oxidative attack occurs at the second carbon atom from the carboxylic group. *C. tropicalis* can also catabolize fatty acids through an ω-oxidation pathway in which only the terminal methyl carbon is oxidized to a carboxylic acid, yielding a dicarboxylic acid. In ω-oxidation, the fatty acid is converted to dicarboxylic acid along a three-step pathway beginning with the oxidation of the terminal methyl group to an alcohol. This step is catalyzed by the hydroxylase complex that contains both the cytochrome P450 monooxygenase (CYP) and cytochrome P450 reductase (NCP) proteins. The alcohol is then converted to an aldehyde by fatty alcohol oxidase (FAO) and then to the dicarboxylic acid by an aldehyde dehydrogenase. The desired product is the long-chain dicarboxylic acid. A fatty alcohol oxidase is distinguished from an alcohol oxidase in its chain length specificity. Alcohol oxidases in general are specific for methanol but can sometimes oxidize alcohols up to C4. Fatty alcohol oxidases generally do not oxidize alcohols with chain lengths less than eight.

In wild-type *Candida tropicalis*, β-oxidation consumes fatty acids much faster than the ω-oxidation pathway can oxidize them. However, by inactivating the POX 4 and POX 5 genes, which gene products are responsible for the initiation of β-oxidation, such genetically engineered *C. tropicalis* strains preferentially shunt fatty acids into the ω-oxidation pathway. The base strain used for the development of various gene-amplified strains is H5343, which is *C. tropicalis* strain 20336 (American Type Culture Collection) with both POX 4 and POX 5 genes inactivated by insertional inactivation. The primary strain used in larger-scale production fermentations is HDC23-3, which is derived from H5343, but also has the CYP52A2 (a cytochrome P450 monooxygenase) gene amplified. The hydroxylase complex is responsible for catalyzing the first step in ω-oxidation, which is considered the rate-limiting step. Amplification of the CYP52A2 and NCP genes help to overcome this rate-limitation, but then the next bottleneck becomes the conversion of the alcohol to the aldehyde by the FAO enzyme. During fermentations with HDC23-3, it has been discovered that a small amount (ca. 0.5% w/w in broth) of ω-hydroxy fatty acid (HFA) accumulates during the fermentation. This partial oxidation product interferes with later purification steps and causes lower overall yields. There is an additional need therefore, for reducing the bottleneck in the conversion of the alcohol to an aldehyde during the second step of the ω-oxidation pathway.

A small number of fatty alcohol oxidases have been described in the scientific literature in various yeasts, examples of which are *Candida tropicalis* (1, 2, 3, 4), *Candida maltosa* (5,6), *Candida cloacae* (4), *Torulopsis candida* (7), *Candida* (Torulopis) *bombicola* (8), and *Candida* (Torulopsis) *apicola* (9). The FAO was purified from the hexadecane-grown yeast, *T. candida* (7) and described as a tetramer (mw 290 kD) with subunit mol. wt. of 75 kD. It has a pH optimum of 7.6 and oxidizes higher alcohols with a carbon chain length of C4 to C16. Hexadecane-grown *C. bombicola* (8) apparently has two different alcohol oxidase activities, one with an optimal chain length specificity of 10 for n-alcohols and another with an optimal chain length specificity of 14. The FAO from *C. maltosa* (6) catalyzes the oxidation of 1-alkanols (C4 to C22) with highest activity utilizing 1-octanol. It also oxidizes 2-alkanols (C8 to C16). α,ω-Alkanediols, ω-hydroxypalmitic acid, phenylalkanols and terpene alcohols were all found to be substrates for the FAO, but at fairly low rates of oxidation. The oxidation of 2-alkanols is stereoselective for the R(−) enantiomers only.

The FAO from *C. tropicalis* (ATCC 20336) grown on hexadecane was first described by Kemp et al. in 1988 (1). It was found to oxidize 1-alkanols from C4 to C18, but has a maximal activity with dodecanol. It was found to oxidize 16-hydroxypalmitate but not 12-hydroxylaurate. The FAO was later purified (3) and was shown to be a dimer (mw=145 kD) with subunit molecular weight of 68–72 kD. The purified enzyme showed similar substrate specificity as described previously, but demonstrated additional activity with 12-hydroxylaurate and 2-dodecanol. The enzyme was found to be a light sensitive flavoprotein, but the identity of the flavin was not known.(10).

Recently two FAO genes from *C. cloacae* and one FAO gene from *C. tropicales* were cloned and the DNA sequences determined (4, 12). The open reading frame (ORF) for FAO1 and FAO2 from *C. cloacae* were 2094 bp and 2091 bp, respectively. The ORF for FAOT from *C. tropicalis* was 2112 bp. FAOT shares 60.6% and 61.7% nucleotide identities and 74.8% and 76.2% amino acid sequence similarities with *C. cloacae* FAO1 and FAO2, respectively. The FAO1 gene but not the FAO2 gene has been successfully cloned and expressed in *Escherichia coli.*

The present invention provides FAO genes from *C. tropicalis* and compositions and methods employing the FAO genes. The compositions and methods are useful for increasing FAO activity during the second step of omega-oxidation of fatty acids and ultimately result in an increase in diacid productivity.

SUMMARY OF THE INVENTION

Figure 1:
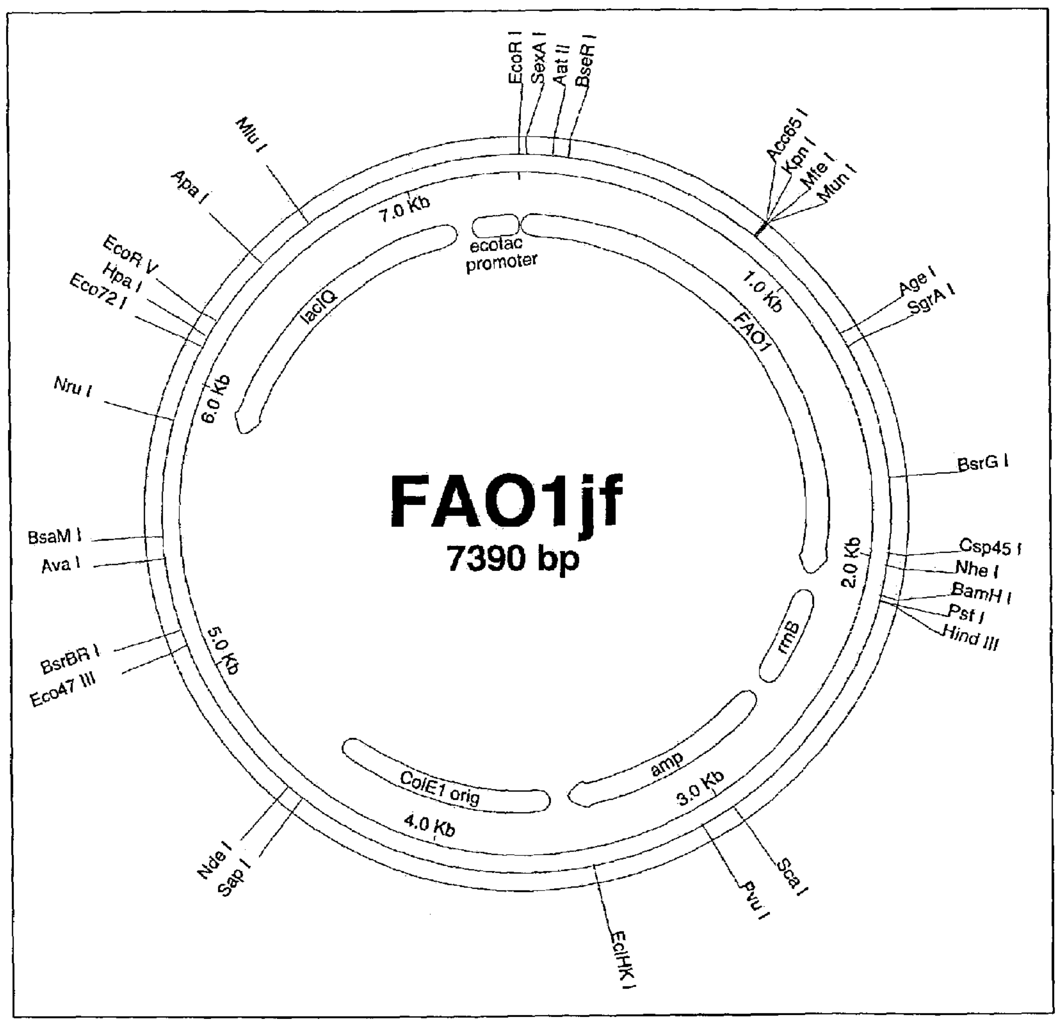
FIG. 1 is a restriction map of FAO1jf which is the coding region of the FAO1 gene ligated into the expression vector pJF118EH.

The present invention provides fatty alcohol oxidase proteins comprising the amino acid sequences set forth in SEQ ID NOs: 2, 4, 6, 10, or 12, including analogs, derivatives, or enzymatically active fragments thereof. Also provided are isolated nucleic acid molecules encoding fatty alcohol oxidase proteins comprising the amino acid sequences set forth in SEQ ID NOs: 2, 4, 6, 10, or 12, including analogs, derivatives, or enzymatically active fragments thereof. Examples of such isolated nucleic acid molecules include those having the sequences set forth in SEQ ID NOs: 1, 3, 5, 9, and 11.

The present invention also provides a peptide consisting of or comprising the sequence set forth in any one of SEQ ID NO:13, SEQ ID NO:14, or SEQ ID NO:19.

In addition, the present invention also provides a fatty alcohol oxidase or enzymatically active fragment thereof having an amino acid sequence identity of at least one of: greater than 82% when compared to the amino acid sequence set forth in SEQ ID NO:2, greater than 83% when compared to the amino acid sequence set forth in SEQ ID NO:2, greater than 84% when compared to the amino acid sequence set forth in SEQ ID NO:2, greater than 85% when compared to the amino acid sequence set forth in SEQ ID NO:2, greater than 90% when compared to the amino acid sequence set forth in SEQ ID NO:2, or greater than 95% when compared to the amino acid sequence set forth in SEQ ID NO:2. Preferably, this fatty alcohol oxidase further comprising a signature peptide having the amino acid sequence set forth in SEQ ID NO:13.

A fatty alcohol oxidase or enzymatically active fragment thereof having an amino acid sequence identity of at least one of: greater than 85% when compared to the amino acid sequence set forth in SEQ ID NO:4, greater than 86% when compared to the amino acid sequence set forth in SEQ ID NO:4, greater than 87% when compared to the amino acid sequence set forth in SEQ ID NO:4, greater than 88% when compared to the amino acid sequence set forth in SEQ ID NO:4 greater than 90% when compared to the amino acid sequence set forth in SEQ ID NO:4, or greater than 95% when compared to the amino acid sequence set forth in SEQ ID NO:4 is also provided. Preferably, this fatty alcohol oxidase comprises a signature peptide having the amino acid sequence set forth in at least one of SEQ ID NO:13, SEQ ID NO:14 or SEQ ID NO:19.

Also in accordance with the present invention, there is provided a fatty alcohol oxidase or enzymatically active fragment thereof having an amino acid sequence identity of at least one of: greater than 85% when compared to the amino acid sequence set forth in SEQ ID NO:6, greater than 86% when compared to the amino acid sequence set forth in SEQ ID NO:6, greater than 87% when compared to the amino acid sequence set forth in SEQ ID NO:6, greater than 88% when compared to the amino acid sequence set forth in SEQ ID NO:6 greater than 90% when compared to the amino acid sequence set forth in SEQ ID NO:6, or greater than 95% when compared to the amino acid sequence set forth in SEQ ID NO:6. Preferably, such a fatty alcohol oxidase also comprises a signature peptide having the sequence set forth in at least one of SEQ ID NO:13, SEQ ID NO:14 or SEQ ID NO:19.

In addition, there is provided an isolated nucleic acid molecule encoding the signature motif set forth in SEQ ID NO:13. For example, the isolated nucleic acid may comprise the nucleotide sequence:

TGY GGN TTY TGY TAY YTN GGN TGY as set forth in SEQ ID NO: 32, wherein:

Y is C or T, and N is A or G, or C or T.

Also provided is an isolated nucleic acid molecule encoding the signature motif set forth in SEQ ID NO:14. For example, such an isolated nucleic acid molecule may comprise the nucleotide sequence: ATH ATH GGN WSN GGN GCN GGN GCN GGN GTN AUG GCN wherein:

R is A or G, Y is C or T, M is A or C, K is G or T, S is G or C, W is A or T, H is A or T or C, B is G or T or C, D is G or A or T, N is A or G, or C or T.

The present invention also provides an isolated nucleic acid molecule encoding the signature motif set forth in SEQ ID NO:19. An example of such a nucleotide sequence includes an isolated nucleic acid molecule comprising the nucleotide sequence:

GCN GGN WSN ACN YTN GGN GGN GGN wherein R is A or G, Y is C or T, M is A or C, K is G or T, S is G or C, W is A or T, H is A or T or C, B is G or T or C, D is G or A or T, N is A or G, or C or T.

The present invention also provides an isolated nucleic acid molecule encoding the signature motif set forth in SEQ ID NO:13 and having a sequence identity of greater than 77% compared to the nucleotide sequence set forth in SEQ ID NO:1; an isolated nucleic acid molecule encoding the signature motif set forth in SEQ ID NO:14 and/or SEQ ID NO:13 and/or SEQ ID NO:19 and having a sequence identity of greater than 78% compared to the nucleotide sequence set forth in SEQ ID NO:3; an isolated nucleic acid molecule encoding the signature motif set forth in SEQ ID NO:14 and/or SEQ ID NO:13 and/or SEQ ID NO:19 and having a sequence identity of greater than 79% compared to the nucleotide sequence set forth in SEQ ID NO:5.

In addition, the present invention also provides an isolated nucleic acid molecule comprising a nucleotide sequence which encodes the signature motif set forth in SEQ ID NO:13 and which hybridizes under medium to high stringency conditions to nucleotides 1941–4054 of the nucleotide sequence set forth in SEQ ID NO:1, and an isolated nucleic acid molecule comprising a nucleotide sequence which encodes the signature motif set forth in SEQ ID NO:13 and/or SEQ ID NO:14 and/or SEQ ID NO:19 and which hybridizes under medium to high stringency conditions to nucleotides 1521–3635 of the nucleotide sequence set forth in SEQ ID NO:3 or nucleotides 1094–3213 of the nucleotides set forth in SEQ ID NO:5.

In accordance with the present invention, there is also provided an isolated nucleic acid molecule comprising an open reading frame (ORF) for a fatty alcohol oxidase (FAO) gene from *Candida tropicalis* wherein the ORF is operably linked to a promoter which is capable of affecting expression of the ORF. Preferably, the FAO comprises the amino acid sequence set forth in SEQ ID NO:2, SEQ ID NO:4, SEQ ID NO:6, SEQ ID NO:10, or SEQ ID NO:12. In another preferred embodiment, the ORF comprises nucleotides 1941–4054 of the nucleotide sequence set forth in SEQ ID NO:1, nucleotides 1521–3635 of the nucleotide sequence set forth in SEQ ID NO:3, or nucleotides 1099–3213 of the nucleotide sequence set forth in SEQ ID NO:5.

Vectors comprising the isolated nucleic acid molecules described herein are also provided. Such vectors include but are not limited to plasmids, phagemids, phage, cosmids, or linear DNA vectors. In addition, host cells are also provided which host cells comprise a subject vector or isolated nucleic acid molecule. Examples of host cells include bacterial cells, fungal cells, insect cells, animal cells or plant cells. examples of fungal cells include those of *Yarrowia* sp., *Bebaromyces* sp., *Saccharomyces* sp., *Schizosaccharomyces* sp., *Pichia* sp. and *Candida* sp. Host cells of *Candida tropicalis* are especially preferred.

The present invention also provides a method of producing an FAO1 protein. The method comprises: transforming a suitable host cell with a DNA sequence encoding a protein having the amino acid sequence as set forth in SEQ ID NO:2; and culturing the cell under conditions favoring expression of the FAO1 protein.

In addition, the present invention provides a method of producing an FAO2a protein. The method comprises the steps of: transforming a suitable host cell with a DNA sequence that encodes a protein having the amino acid sequence as set forth in SEQ ID NO:4; and culturing the cell under conditions favoring expression of the FAO2a protein.

A method of producing an FAO2b protein is further provided. The method comprises the steps of transforming a suitable host cell with a DNA sequence that encodes a protein having the amino acid sequence as set forth in SEQ ID NO:6; and culturing the cell under conditions favoring the expression of the protein.

In accordance with the present invention, there is also provided a method for increasing production of an aldehyde during the second step of the ω-oxidation pathway of fatty acids. The method comprises the steps of:

(a) providing a host cell having a naturally occurring number of FAO genes;

(b) increasing, in the host cell, the number of FAO1 genes which encode an FAO1 protein having the amino acid sequence as set forth in SEQ ID NO:2; and (c) culturing the host cell in media containing an organic substrate which upregulates the FAO1 gene, to effect increased production of an aldehyde. Preferably, the FAO1 gene comprises nucleotides 1941–4054 of the nucleotide sequence as set forth in SEQ ID NO:1.

Also provided by the present invention is a method for increasing production of an aldehyde during the second step of the ω-oxidation pathway of fatty acid. The method comprises the steps of:

(a) providing a host cell having a naturally occurring number of FAO genes;

(b) increasing, in the host cell, the number of FAO2 genes which encode an FAO2a protein having the amino acid sequence as set forth in SEQ ID NO:4; and (c) culturing the host cell in media containing an organic substrate which upregulates the FAO2 gene, to effect increased production of an aldehyde. Preferably, the FAO2a gene comprises nucleotides 1521–3635 of the nucleotide sequence as set forth in SEQ ID NO:3.

A method for increasing production of an aldehyde during the second step of the ω-oxidation pathway of fatty acids is still further provided. The method comprises the steps of:

(a) providing a host cell having a naturally occurring number of FAO genes;

(b) increasing, in the host cell, the number of FAO2 genes which encode an FAO2b protein having the amino acid sequence as set forth in SEQ ID NO:6; and (c) culturing the host cell in media containing an organic substrate which upregulates the FAO2b gene, to effect increased production of an aldehyde. Preferably, the FAO2b gene comprises nucleotides 1099–3213 of the nucleotide sequence as set forth in SEQ ID NO:5.

A method for increasing production of a dicarboxylic acid is also provided. The method comprises: (a) providing a host cell having a naturally occurring number of FAO genes; (b) increasing, in the host cell, the number of FAO1 genes which encode an FAO1 protein having the amino acid sequence as set forth in SEQ ID NO:2; and (c) culturing the host cell in media containing an organic substrate which upregulates the FAO1 gene, to effect increased production of dicarboxylic acid. Preferably, the FAO1 gene comprises nucleotides 1941–4054 of the nucleotide sequence as set forth in SEQ ID NO:1.

The present invention still further provides a method for increasing production of a dicarboxylic acid, said method comprising: (a) providing a host cell having a naturally occurring number of FAO genes; (b) increasing, in the host cell, the number of FAO2a genes which encode an FAO2 protein having the amino acid sequence as set forth in SEQ ID NO:4; and (c) culturing the host cell in media containing an organic substrate which upregulates the FAO2a gene, to effect increased production of dicarboxylic acid. Preferably, the FAO2a gene comprises nucleotides 1521–3635 of the nucleotide sequence as set forth in SEQ ID NO:3.

In still another embodiment of the present invention, there is provided a method for increasing production of a dicarboxylic acid. The method comprises the steps of: (a) providing a host cell having a naturally occurring number of FAO genes; (b) increasing, in the host cell, the number of FAO2b genes which encode an FAO2 protein having the amino acid sequence as set forth in SEQ ID NO:6; and (c) culturing the host cell in media containing an organic substrate which upregulates the FAO2b gene, to effect increased production of dicarboxylic acid. Preferably, the FAO2b gene comprises nucleotides 1099–3213 of the nucleotide sequence as set forth in SEQ ID NO:5.

In still another embodiment, the present invention provides a method for increasing the production of an FAO1 protein having an amino acid sequence as set forth in SEQ ID NO:2. The method comprises the steps of:

(a) transforming a host cell having a naturally occurring level of FAO1 protein with an increased copy number of an FAO1 gene that encodes the FAO1 protein having the amino acid sequence as set forth in SEQ ID NO:2; and (b) culturing the cell and thereby increasing expression of the protein compared with that of a host cell containing a naturally occurring copy number of the FAO1 gene.

A method for increasing the production of an FAO2 protein having an amino acid sequence as set forth in SEQ ID NO:4 is further provided. The method comprises:

(a) transforming a host cell having a naturally occurring amount of FAO2 protein with an increased copy number of an FAO2 gene that encodes the FAO2 protein having the amino acid sequence as set forth in SEQ ID NO:4; and (b) culturing the cell and thereby increasing expression of the protein compared with that of a host cell containing a naturally occurring copy number of the FAO2 gene.

In yet another aspect of the invention, there is provided a method for increasing production of an aldehyde during the second step of the ω-oxidation pathway of fatty acids. The method comprises the steps of:

(a) isolating a nucleic acid molecule comprising coding sequence for an FAO1 gene;

(b) isolating a promoter sequence from a gene which transcribes at a higher rate than the FAO1 gene;

(c) operably linking the promoter sequence to the open reading frame (ORF) of the FAO1 gene to create a fusion gene;

(d) inserting the fusion gene into an expression vector;

(e) transforming a host cell with the expression vector and (f) culturing the transformed host cell in a media containing an organic substrate that is biooxidizable to a mono- or polycarboxylic acid. Preferably, the nucleic acid molecule encodes an FAO1 comprising the amino acid sequence set forth in SEQ ID NO:2.

A method for increasing production of an aldehyde from an alcohol during the second step of the ω-oxidation pathway of fatty acids is still further provided. The method comprises the steps of:

(a) isolating a nucleic acid molecule comprising coding sequence for an FAO2 gene;

(b) isolating a promoter sequence from a gene which transcribes at a higher rate than the FAO2 gene, (c) operably linking the promoter sequence to the open reading frame (ORF) of the FAO2 gene to create a fusion gene;

(d) inserting the fusion gene into an expression vector;

(e) transforming a host cell with the expression vector and (f) culturing the transformed host cell in a media containing an organic substrate that is biooxidizable to a mono- or polycarboxylic acid. Preferably, the nucleic acid molecule encodes an FAO2 protein comprising the amino acid sequence as set forth in SEQ ID NOs:4 or 6.

A method of increasing production of an ketone from an alcohol during the second step of the ω-oxidation pathway of fatty acids is additionally provided. The method comprises the steps of:

(a) isolating a nucleic acid molecule comprising coding sequence for an FAO2 gene;

b) isolating a promoter sequence from a gene which transcribes at a higher rate than the FAO2 gene, (c) operably linking the promoter sequence to the open reading frame (ORF) of the FAO2 gene to create a fusion gene;

(d) inserting the fusion gene into an expression vector;

(e) transforming a host cell with the expression vector and (f) culturing the transformed host cell in a media containing an organic substrate that is biooxidizable to a mono- or polycarboxylic acid. Preferably, the nucleic acid molecule encodes an FAO2 protein comprising the amino acid sequence as set forth in SEQ ID NOs:4 or 6.

In still another aspect of the invention, there is provided a method for increasing dicarboxylic acid production. The method comprises the steps of:

(a) isolating a nucleic acid molecule comprising coding sequence for an FAO1 gene;

(b) isolating a promoter sequence from a gene which transcribes at a higher rate than the FAO1 gene;

(c) operably linking the promoter sequence to the open reading frame (ORF) of the FAO1 gene to create a fusion gene;

(d) inserting the fusion gene into an expression vector;

(e) transforming a host cell with the expression vector; and (f) culturing the transformed host cell in a media containing an organic substrate that is biooxidizable to a mono- or polycarboxylic acid. Preferably, the ORF of the FAO1 gene comprises nucleotides 1941–4054 of the nucleotide sequence set forth in SEQ ID NO:1.

A method of increasing dicarboxylic acid production is still further provided. The method comprises the steps of:

(a) isolating a nucleic acid molecule comprising coding sequence for an FAO2 gene;

(b) isolating a promoter sequence from a gene which transcribes at a higher rate than the FAO2 gene, (c) operably linking the promoter sequence to the open reading frame (ORF) of the FAO2 gene to create a fusion gene;

(d) inserting the fusion gene into an expression vector; (d) transforming a host cell with the expression vector; and (e) culturing the transformed host cell in a media containing an organic substrate that is biooxidizable to a mono- or polycarboxylic acid. Preferably, the ORF of the FAO2 gene comprises nucleotides 1521–3635 of the nucleotide sequence as set forth in SEQ ID NO:3 or nucleotides 1099–3213 of the nucleotide sequence set forth in SEQ ID NO:5.

DETAILED DESCRIPTION OF THE INVENTION

Diacid productivity is improved according to the present invention by selectively increasing enzymes which are known to be important to the oxidation of organic substrates such as fatty acids or aliphatic compounds, such as alkanes. In accordance with the present invention, two fatty alcohol oxidase (FAO) genes of *C. tropicalis*, have been identified and characterized. The FAO genes encode fatty alcohol oxidase enzymes, which catalyze the conversion of an alcohol to an aldehyde during the second step of the ω-oxidation pathway. Amplification of the FAO gene copy number and/or transcriptional activity in a host cell results in higher alcohol oxidase activity, higher diacid productivity, and, when fatty acid substrates are used, lower ω-hydroxy fatty acid levels.

The present invention provides nucleotide sequences from *C. tropicalis* that encode two different fatty alcohol oxidases, each of which has a different substrate specificity. In one embodiment, there is provided an isolated nucleic acid molecule which encodes the fatty alcohol oxidase enzyme FAO1, having the amino acid sequence as set forth in SEQ ID NO:2. An example of such an isolated nucleic acid molecule includes the FAO1 gene having the nucleotide sequence as set forth in SEQ ID NO:1.

In another aspect of the invention, there are provided isolated nucleic acid molecules that encode the fatty alcohol oxidase enzyme FAO2. In accordance with the present invention, two alleles have been identified and isolated which encode the FAO2 enzyme. The two alleles, FAO2a and FAO2b, are 95% identical by DNA sequence and have 98% similarity by amino acid sequence. The FAO2a enzyme comprises the amino acid sequence as set forth in SEQ ID NO:4. An example of a nucleotide sequence which encodes the FAO2a enzyme is set forth in SEQ ID NO:3. The FAO2b enzyme comprises the amino acid sequence as set forth in SEQ ID NO:6. An example of a nucleotide sequence which encodes the FAO2b enzyme is set forth in SEQ ID NO:5.

It has recently been determined that certain eukaryotes, e.g., certain yeasts, do not adhere, in some respects, to the "universal" genetic code which provides that particular codons (triplets of nucleic acids) code for specific amino acids. Indeed, the genetic code is "universal" because it is virtually the same in all living organisms. Certain *Candida* sp. are now known to translate the CTG codon (which, according to the "universal" code designates leucine), as serine. See, e.g., Ueda et al., *Biochemie* (1994) 76, 1217–1222, where *C. tropicalis, C. cylindracea, C. guilliermodii* and *C. lusitaniae* are shown to adhere to the "non-universal" code with respect to the CTG codon. Accordingly, nucleic acid sequences may code for one amino acid sequence in "universal" code organisms and a variant of that amino acid sequence in "non-universal" code organisms depending on the presence of CTG codons in the nucleic acid coding sequence. The difference may become evident when, in the course of genetic engineering, a nucleic acid molecule encoding a protein is transferred from a "non-universal" code organism to a "universal" code organism or vice versa. Obviously, there will be a different amino acid sequence depending on which organism is used to express the protein.

Thus, the present invention also provides an amino acid sequence (set forth in SEQ ID NO:10) for an FAO2a enzyme when FAO2a is expressed in a species of *Candida* such as *C. tropicalis*. The amino acid sequence set forth in SEQ ID NO:10 has a serine residue at position 177. An example of a nucleotide sequence encoding the amino acid sequence set forth in SEQ ID NO:10 is provided by the nucleotide sequence set forth in SEQ ID NO:9 where a TCG codon is substituted for a CTG codon at position 2049–2051.

The present invention also provides an amino acid sequence (set forth in SEQ ID NO:12) for an FAO2b enzyme when FAO2b is expressed in a species of *Candida* such as *C. tropicalis*. The amino acid sequence set forth in SEQ ID NO:12 has a serine residue at position 177. An example of a nucleotide sequence encoding the amino acid sequence set forth in SEQ ID NO:12 is provided by the nucleotide sequence set forth in SEQ ID NO:11 where a TCG codon is substituted for a CTG codon at positions 1627–1629.

The present invention also provides FAO proteins. For example, there is provided an FAO1 protein having the amino acid sequence as set forth in SEQ ID NO:2 or an enzymatically active fragment thereof. Further, there is provided an FAO2a protein comprising the amino acid sequence as set forth in SEQ ID NO:4 or an enzymatically active fragment thereof. In another embodiment, there is provided an FAO2b protein comprising the amino acid sequence as set forth in SEQ ID NO:6 or an enzymatically active fragment thereof. In yet another embodiment, there is provide an FAO2a protein comprising the amino acid sequence as set forth in SEQ ID NO:10 or an enzymatically active fragment thereof. In still another embodiment, an FAO2b protein having the amino acid sequence as set forth in SEQ ID NO:12 or an enzymatically active fragment thereof is provided. As used herein, "enzymatically active fragment" refers to a portion of the FAO enzyme which is sufficient to retain enzymatic activity in converting an alcohol to an aldehyde.

In accordance with the present invention, FAO1 and FAO2 proteins may be prepared by methods familiar to those skilled in the art such as by cloning the FAO1 and FAO2 genes (including the FAO2a and/or FAO2b alleles) into an appropriate expression vector followed by expression in a suitable host cell. See, e.g., U.S. Pat. No. 6,331,420, incorporated by reference herein as if fully set forth. The relevant enzyme or fragment thereof, may also be generated by direct amplification of corresponding coding sequence via PCR, followed by standard recombinant procedures and expression in a suitable host cell. With respect to FAO analogs, derivatives, FAO-like molecules, portions or enzymatically active fragments thereof (as defined herein), PCR primers may be designed to allow direct amplification of coding sequences for corresponding amino acid insertional, deletional, or substitutional amino acid variants (as defined herein). Primers for use in PCR may be synthetic oligonucleotides prepared on an automated oligonucleotide synthesizer such as an ABI DNA synthesizer available from Perkin-Elmer Corporation. In addition, oligonucleotides may be purchased from commercial manufacturers, for example, from Synthetic Genetics (San Diego, Calif.). FAO1 and FAO2 proteins may also be chemically synthesized using well-known methodologies.

The appropriate DNA sequence may be inserted into a vector by a variety of procedures deemed to be within the scope of those skilled in the art, which can include insertion of the DNA into an appropriate restriction endonuclease site(s) or cloning the DNA sequence into the expression vectors using high fidelity polymerase chain reaction. Standard techniques for the construction of such vectors are well-known to those of ordinary skill in the art and may be found in references such as Sambrook et al. (1989) *Molecular Cloning: A Laboratory Manual*, Cold Spring Harbor Laboratory Press, Cold Spring Harbor, N.Y., or any of the myriad of laboratory manuals on recombinant DNA technology which are widely available. A variety of strategies are available for ligating fragments of DNA, the choice of which depends on the nature of the termini of the DNA fragments. The vector may also include appropriate sequences for amplifying expression, or sequences that facilitate cloning, expression or processing.

In addition, the expression vectors preferably contain one or more selectable marker genes to provide a phenotypic trait for selection of transformed host cells such as dihydrofolate reductase or neomycin resistance for eukaryotic cell culture, or tetracycline or ampicillin resistance in *E. coli.*

The vector containing the appropriate DNA sequence as hereinabove described, as well as an appropriate promoter or control sequence, may be employed to transform an appropriate host to permit the host to express the enzyme. "Transformation" includes all forms of causing uptake of foreign DNA by a host cell. The transformed cells are then screened for those that contain the desired DNA and the successful transformants are cultured under conditions that affect the expression of the coding sequences.

Representative examples of appropriate hosts include bacterial cells, such as *E. coli* and *Streptomyces*; fungal cells, such as yeast; insect cells such as *Drosophila* S2 and *Spodoptera* Sf9; animal cells; adenoviruses; plant cells, etc. The selection of an appropriate host is deemed to be within the scope of those skilled in the art from the teachings herein and can include expression host BL21 or BL21 CodonPlus RIL strain (Stratagene, La Jolla, Calif.).

Following transformation of the host strain, the enzyme is induced by appropriate means (e.g., temperature shift or chemical induction) and cells are cultured for an additional period. If the FAO coding sequence is under control of its native promoter, oleic acid may be used to induce expression. If the FAO is operably linked to a heterologous promoter, other inducers may be used. One preferred method of induction is through the use of IPTG (Isopropyl-β-D-thiogalactopyranoside).

Cells are typically disrupted by physical or chemical means known to those skilled in the art, centrifuged, and the resulting crude extract retained for further purification. Purification of FAO1 or FAO2 or fragment thereof can be carried out by any means known to those skilled in the art and can include chromatographic techniques, such as histidine-tag affinity chromatography and Nickel affinity chromatography. Commercially available kits for this purification can be purchased from vendors (Qiagen, Inc. Chatsworth, Calif.; Novagen, Calif., USA). An immunoassay, such as a Western blot assay, can then be utilized to verify the presence of the recombinant enzyme.

Also in accordance with the present invention, three different signature peptide sequences which are unique to the FAO1 and FAO2 proteins of the present invention have been discovered. The first signature peptide has the amino acid sequence: CGFCYLGC (SEQ ID NO:13). This first signature peptide is found in both FAO1 and FAO2 proteins of the present invention but not in other previously characterized yeast FAO proteins. With reference to SEQ ID NO:2 (FAO1 protein), SEQ ID NO:4 (FAO2a protein), and SEQ ID NO:6 (FAO2b protein), the first signature peptide (SEQ ID NO:13) is located at amino acid positions 355 to 362. A second signature peptide has the amino acid sequence IIGSGAGAGVMA (SEQ ID NO:14). This second signature peptide is present in the FOA2a and FAO2b proteins of the present invention but not in the FAO1 protein of the present invention, nor previously characterized yeast FAO proteins. With reference to SEQ ID NOs:4 and 6, the second signature peptide is located at amino acid positions 198 to 209. A third signature peptide is found in the FAO2a and FAO2b proteins of the present invention but not in other previously characterized yeast FAO proteins. The third signature peptide has the amino acid sequence AGSTLGGG (SEQ ID NO:19). With reference to SEQ ID NOs:4 and 6, this third signature peptide is located at amino acid positions 262 to 269.

Thus in accordance with the present invention, there is provided a peptide having the amino acid sequence: CGFCYLGC (SEQ ID NO:13). Also in accordance with the present invention, there is provided a peptide having the amino acid sequence IIGSGAGAGVMA (SEQ ID NO:14). A peptide having the amino acid sequence AGSTLGGG (SEQ ID NO:19) is also provided by the present invention. These peptides are useful e.g., in producing antibodies which specifically bind to a yeast FAO comprising the amino acid sequence of the signature peptides. Such antibodies are useful in immunoassays such as radioimmunoassays, enzyme-linked immunosorbent assays (ELISA), Westerns blot, immunofluorescent assays, chemiluminescent assays and bioluminescent assays. These types of assays are useful for monitoring the FAO enzyme levels at different times during a fermentation run and can aid in solving problems that might arise during fermentation.

Structurally related amino acid sequences may be substituted for the disclosed sequences set forth in SEQ ID NOs: 2, 4, 6, 10, 12, 13, 14, or 19 in practicing the present invention. Amino acid insertional derivatives of the proteins and peptides of the present invention include amino and/or carboxyl terminal fusions as well as intra-sequence insertions of single or multiple amino acids. Insertional amino acid sequence variants are those in which one or more amino acid residues are introduced into a predetermined site in a subject FAO protein or peptide although random insertion is also possible with suitable screening of the resulting product. Deletional variants may be made by removing one or more amino acids from the sequence of a subject peptide. Substitutional amino acid variants are those in which at least one residue in the sequence has been removed and a different residue inserted in its place. Typical substitutions are those made in accordance with the following Table 1:

TABLE 1

Suitable residues for amino acid substitutions

| Original Residue | Exemplary Substitutions |
|---|---|
| Ala (A) | Ser |
| Arg (R) | Lys |
| Asn (N) | Gln; His |
| Asp (D) | Glu |
| Cys (C) | Ser |
| Gln (Q) | Asn |
| Glu (E) | Asp |
| Gly (G) | Pro |
| His (H) | Asn; Gln |
| Ile (I) | Leu; Val |
| Leu (L) | Ile; Val |
| Lys (K) | Arg; Gln; Glu |
| Met (M) | Leu; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

When a subject FAO protein or peptide is derivatised by amino acid substitution, the amino acids are generally replaced by other amino acids having like properties such as hydrophobicity, hydrophilicity, electronegativety, bulky side chains and the like. As used herein, the terms "derivative", "analogue", "fragment", "portion" and "like molecule" refer to a subject FAO protein having an amino acid sequence as set forth in SEQ ID NOs: 2, 4, 6, 10 or 12 and having an amino acid substitution, insertion, addition, or deletion, as long as said derivative, analogue, fragment, portion, or like molecule retains the ability to function as a fatty alcohol oxidase, i.e., retains the ability to convert an alcohol to an aldehyde. Likewise, the terms "derivative", "analogue", "fragment", "portion" and "like molecule" may also refer to a subject FAO signature peptide having an amino acid sequence as set forth in SEQ ID NOs: 13, 14, or 19 and having an amino acid substitution, insertion, addition, or deletion, as long as said derivative, analogue, fragment, portion, or like molecule of an FAO signature peptide, when incorporated within a larger FAO protein, derivative, analogue, fragment, portion or like-molecule, does not diminish FAO activity.

The synthetic peptides of the present invention may be synthesized by a number of known techniques. For example, the peptides may be prepared using the solid-phase technique initially described by Merrifield (1963) in *J. Am. Chem. Soc.* 85:2149–2154. Other peptide synthesis techniques may be found in M. Bodanszky et al. *Peptide Synthesis*, John Wiley and Sons, 2d Ed., (1976) and other references readily available to those skilled in the art. A summary of polypeptide synthesis techniques may be found in J. Sturart and J. S. Young, *Solid Phase Peptide Synthesis*, Pierce Chemical Company, Rockford, Ill., (1984). Peptides may also be synthesized by solution methods as described in The Proteins, Vol. II, 3d Ed., Neurath, H. et al., Eds., pp. 105–237, Academic Press, New York, N.Y. (1976). Appropriate protective groups for use in different peptide syntheses are described in the texts listed above as well as in J. F.

W. McOmie, *Protective Groups in Organic Chemistry*, Plenum Press, New York, N.Y. (1973). The peptides of the present invention may also be prepared by chemical or enzymatic cleavage from larger portions of a subject FAO protein or from a full length FAO protein.

Additionally, the FAO proteins and peptides of the present invention may also be prepared by recombinant DNA techniques. For most amino acids used to build proteins, more than one coding nucleotide triplet (codon) can code for a particular amino acid residue. This property of the genetic code is known as redundancy. Therefore, a number of different nucleotide sequences may code for a particular FAO protein or peptide.

Thus, other FAO proteins or enzymatically active fragments thereof, which share sufficient amino acid identities with the FAO1, FAO2a, and FAO2b of the present invention (SEQ ID NOs: 2, 4, and 6) are within the scope of the present invention. For example, the present invention provides an FAO enzyme having an amino acid sequence identity greater than 82% when compared to the amino acid sequence of the FAO1 as set forth in SEQ ID NO:2. Preferably, an FAO enzyme having an amino acid sequence identity greater than 82% when compared to the amino acid sequence of the FAO1 set forth in SEQ ID NO:2 comprises the signature motif CGFCYLGC (SEQ ID NO:13). In another embodiment, the FAO enzyme has an amino acid sequence identity greater than 83% when compared to the amino acid sequence of FAO1 as set forth in SEQ ID NO:2. Preferably, an FAO enzyme having an amino acid sequence identity greater than 83% when compared to the amino acid sequence set forth in SEQ ID NO:2 comprises the signature motif CGFCYLGC (SEQ ID NO:13). In still another embodiment, an FAO enzyme has an amino acid sequence identity greater than 84% when compared to the amino acid sequence of FAO1 as set forth in SEQ ID NO:2. Preferably, an FAO enzyme having an amino acid sequence identity greater than 84% when compared to the amino acid sequence set forth in SEQ ID NO:2 comprises the signature motif GGFCYLGC (SEQ ID NO:13). Even more preferably, the FAO enzyme has an amino acid sequence identity greater than 85% when compared to the amino acid sequence of FAO1 as set forth in SEQ ID NO:2. Preferably, an FAO enzyme having an amino acid sequence identity greater than 85% when compared to the amino acid sequence of FAO1 as set forth in SEQ ID NO:2 comprises the signature motif GGFCYLGC (SEQ ID NO:13). In a still more preferred embodiment, a subject FAO enzyme has an amino acid sequence identity greater than 90% when compared to the amino acid sequence of FAO1 as set forth in SEQ ID NO:2. In this embodiment, it is preferable that a subject FAO enzyme having an amino acid identity greater than 90% when compared to the amino acid sequence of FAO1 as set forth in SEQ ID NO:2 also comprises the signature motif GGFCYLGC (SEQ ID NO:13). In a most preferred embodiment, the FAO enzyme has an amino acid identity greater than 95% when compared to the amino acid sequence of FAO1 as set forth in SEQ ID NO:2. In this embodiment, it is preferable that a subject FAO enzyme having an amino acid identity of greater than 95% when compared to the amino acid sequence of FAO1 as set forth in SEQ ID NO:2 also comprises the signature motif GGFCYLGC (SEQ ID NO:13).

In another embodiment, the present invention provides an FAO enzyme having an amino acid sequence identity greater than 85% when compared to the amino acid sequence of FAO2a as set forth in SEQ ID NO:4. In this embodiment, the subject FAO enzyme preferably also comprises the signature motif IIGSGAGAGVMA (SEQ ID NO:14) and/or AGSTLGGG (SEQ ID NO:19), and/or GGFCYLGC (SEQ ID NO:13). In another embodiment, a subject FAO enzyme has an amino acid sequence identity greater than 86% when compared to the amino acid sequence of the FAO2a as set forth in SEQ ID NO:4. In this embodiment, it is preferred that the subject FAO enzyme comprises the signature motif IIGSGAGAGVMA (SEQ ID NO:14) and/or AGSTLGGG (SEQ ID NO:19), and/or GGFCYLGC (SEQ ID NO:13). In an even more preferred embodiment, a subject FAO enzyme has an amino acid sequence identity greater than 87% when compared to the amino acid sequence of the FAO2a as set forth in SEQ ID NO:4. In this embodiment, a subject FAO enzyme having an amino acid sequence identity greater than 87% preferably also comprises the signature motif IIGSGAGAGVMA (SEQ ID NO:14) and/or AGSTLGGG (SEQ ID NO:19), and/or GGFCYLGC (SEQ ID NO:13). Still more preferably, the FAO enzyme has an amino acid sequence identity greater than 88% when compared to the amino acid sequence of the FAO2a as set forth in SEQ ID NO:4. In this embodiment, the FAO enzyme having an amino acid sequence identity greater than 88% when compared to the amino acid sequence of the FAO2a as set forth in SEQ ID NO:4 preferably comprises the signature motif IIGSGAGAGVMA (SEQ ID NO:14) and/or AGSTLGGG (SEQ ID NO:19), and/or GGFCYLGC (SEQ ID NO:13). In an even more preferred embodiment, the FAO enzyme has an amino acid sequence identity greater than 90% when compared to the amino acid sequence of the FAO2a as set forth in SEQ ID NO:4. In this embodiment, it is preferred that the FAO enzyme having an amino acid sequence identity greater than 90% when compared to the amino acid sequence of the FAO2a as set forth in SEQ ID NO:4 also comprises the signature motif IIGSGAGAGVM (SEQ ID NO:14) and/or AGSTLGGG (SEQ ID NO:19), and/or GGFCYLGC (SEQ ID NO:13). In a most preferred embodiment, the FAO enzyme has an amino acid sequence identity greater than 95% when compared to the amino acid sequence of the FAO2a as set forth in SEQ ID NO:4. In this embodiment, the FAO enzyme having an amino acid sequence identity greater than 95% when compared to the amino acid sequence of the FAO2a as set forth in SEQ ID NO:4 preferably also comprises the signature motif IIGSGAGAGVM (SEQ ID NO:14) and/or AGSTLGGG (SEQ ID NO:19), and/or GGFCYLGC (SEQ ID NO:13).

In still another embodiment, the present invention provides an FAO enzyme having an amino acid sequence identity greater than 85% when compared to the amino acid sequence of FAO2b as set forth in SEQ ID NO:6. Preferably, an FAO enzyme having an amino acid sequence identity greater than 85% when compared to the amino acid sequence of FAO2b as set forth in SEQ ID NO:6 also comprises the signature motif IIGSGAGAGVMA (SEQ ID NO:14) and/or AGSTLGGG (SEQ ID NO:19), and/or GGFCYLGC (SEQ ID NO:13). In another embodiment, a subject FAO enzyme has an amino acid sequence identity greater than 86% when compared to the amino acid sequence of the FAO2b as set forth in SEQ ID NO:6. In this embodiment, the FAO enzyme having an amino acid sequence identity greater than 86% when compared to the amino acid sequence of the FAO2b as set forth in SEQ ID NO:6 preferably comprises the signature motif IIGSGAGAGVMA (SEQ ID NO:14) and/or AGSTLGGG (SEQ ID NO:19), and/or GGFCYLGC (SEQ ID NO:13). Even more preferably, the FAO enzyme has an amino acid sequence identity greater than 87% when compared to the amino acid sequence of the FAO2b as set forth in SEQ ID NO:6. In this embodiment, the FAO enzyme having an amino acid sequence identity greater than 87% when compared to the amino acid sequence of the FAO2b as set forth in SEQ ID NO:6 preferably comprises the signature motif IIGSGAGAGVMA (SEQ ID NO:14) and/or AGSTLGGG (SEQ ID NO:19), and/or GGFCYLGC (SEQ ID NO:13). Still more preferably, the FAO enzyme has an amino acid sequence identity greater than 88% when compared to the amino acid sequence of the FAO2b as set forth in SEQ ID NO:6. In this embodiment, the FAO enzyme having an amino acid sequence identity greater than 88% when compared to the amino acid sequence of the FAO2b as set forth in SEQ ID NO:6 preferably also comprises the signature motif IIGSGAGAGVM (SEQ ID NO:14) and/or AGSTLGGG (SEQ ID NO:19), and/or GGFCYLGC (SEQ ID NO:13). In an even more preferred embodiment, the FAO enzyme has an amino acid sequence identity greater than 90% when compared to the amino acid sequence of the FAO2b as set forth in SEQ ID NO:6. Preferably, the FAO enzyme having an amino acid sequence identity greater than 90% when compared to the amino acid sequence of the FAO2b enzyme as set forth in SEQ ID NO:6 also comprises the signature motif IIGSGAGAGVM (SEQ ID NO:14) and/or AGSTLGGG (SEQ ID NO:19), and/or GGFCYLGC (SEQ ID NO:13). In a most preferred embodiment, the FAO enzyme has an amino acid sequence identity greater than 95% when compared to the amino acid sequence of the FAO2b as set forth in SEQ ID NO:6. In this embodiment, the FAO enzyme having an amino acid identity greater than 95% when compared to the amino acid sequence of the FAO2b as set forth in SEQ ID NO:6 also preferably comprises the signature motif IIGSGAGAGVM (SEQ ID NO:14) and/or AGSTLGGG (SEQ ID NO:19), and/or GGFCYLGC (SEQ ID NO:13).

The present invention also provides nucleic acid molecules comprising nucleotide sequences which code for the signature motif of a subject FAO1 and FAO2. For example, a nucleotide sequence which encodes the signature motif CGFCYLGC (SEQ ID NO:13) is provided as:

```
TGY GGN TTY TGY TAY YTN GGN TGY (SEQ ID NO:32)
```

wherein:

R is A or G, Y is C or T, M is A or C, K is G or T, S is G or C, W is A or T, H is A or T or C, B is G or T or C, D is G or A or T, N is A or G, or C or T.

In addition, a nucleic acid molecule comprising a nucleotide sequence which codes for the signature motif IIGSGAGAGVMA (SEQ ID NO:14) of a subject FAO2 is provided which has the following sequence:

ATH ATH GGN WSN GGN GCN GGN GCN GGN GTN ATG GCN (SEQ ID NO:33)

wherein:

R is A or G, Y is C or T, M is A or C, K is G or T, S is G or C, W is A or T, H is A or T or C, B is G or T or C, D is G or A or T, N is A or G, or C or T.

Further, a nucleic acid molecule comprising a nucleotide sequence which codes for the signature motif AGSTLGGG (SEQ ID NO:19) is provided as:

```
GCN GGN WSN ACN YTN GGN GGN GGN (SEQ ID NO:34)
```

wherein R is A or G, Y is C or T, M is A or C, K is G or T, S is G or C, W is A or T, H is A or T or C, B is G or T or C, D is G or A or T, N is A or G, or C or T.

The nucleic acid molecules encoding the FAO1 and FAO2 signature motifs are useful for identifying and isolating genes encoding FAO proteins from *Candida tropicalis.*

In another aspect of the invention, there are provided nucleotide sequences which have a sequence identity of greater than 77% when compared to the nucleotide sequence of the subject FAO1 ORF (SEQ ID NO:1) and which also encode the signature motif CGFCYLGC (SEQ ID NO:13). Preferably, the nucleotide sequence has a sequence identity of greater than 78% when compared to the nucleotide sequence of the subject FAO1 ORF (SEQ ID NO:1) and encodes the signature motif CGFCYLGC (SEQ ID NO:13). More preferably, the nucleotide sequence has a nucleic acid sequence identity of greater than 79% when compared to the nucleotide sequence of the subject FAO1 ORF (SEQ ID NO:1) and encodes the signature motif CGFCYLGC (SEQ ID NO:13). Even more preferably, the nucleotide sequence has a sequence identity of greater than 79% when compared to the nucleotide sequence of the subject FAO1 ORF (SEQ ID NO:1) and encodes the signature motif CGFCYLGC (SEQ ID NO:13). In a most preferred embodiment, the nucleotide sequence has a sequence identity of greater than 80% when compared to the nucleotide sequence of the subject FAO1 ORF (SEQ ID NO:1) and encodes the signature motif CGFCYLGC (SEQ ID NO:13).

In yet another aspect of the present invention there are provided nucleotide sequences which have a sequence identity of greater than 78% when compared to the nucleotide sequence of the subject FAO2a ORF (SEQ ID NO:3) and which also encode the signature motif IIGSGAGAGVMA (SEQ ID NO:14) and/or CGFCYGC (SEQ ID NO:13) and/or AGSTLGGG (SEQ ID NO:19). Preferably, the nucleotide sequence has a sequence identity of greater than 79% when compared to the nucleotide sequence of the subject FAO2a ORF (SEQ ID NO:3) and encodes the signature motif IIGSGAGAGVMA (SEQ ID NO:14) and/or CGFCYGC (SEQ ID NO:13) and/or AGSTLGGG (SEQ ID NO:19). More preferably, the nucleotide sequence has a sequence identity of greater than 80% when compared to the nucleotide sequence of the subject FAO2 ORF (SEQ ID NO:3) and encodes the signature motif IIGSGAGAGVMA (SEQ ID NO:14) and/or CGFCYGC (SEQ ID NO:13) and/or AGSTLGGG (SEQ ID NO:19).

In yet another aspect of the present invention there are provided nucleotide sequences which have a sequence identity of greater than 78% when compared to the nucleotide sequence of the subject FAO2b ORF (SEQ ID NO:5) and which also encode the signature motif IIGSGAGAGVMA (SEQ ID NO:14) and/or CGFCYGC (SEQ ID NO:13) and/or AGSTLGGG (SEQ ID NO:19). Preferably, the nucleotide sequence has a sequence identity of greater than 79% when compared to the nucleotide sequence of the subject FAO2b ORF (SEQ ID NO:5) and encodes the signature motif IIGSGAGAGVMA (SEQ ID NO:14) and/or CGFCYGC (SEQ ID NO:13) and/or AGSTLGGG (SEQ ID NO:19). More preferably, the nucleotide sequence has a sequence identity of greater than 80% when compared to the nucleotide sequence of the subject FAO2b ORF (SEQ ID NO:5) and encodes the signature motif IIGSGAGAGVMA (SEQ ID NO:14) and/or CGFCYGC (SEQ ID NO:13) and/or AGSTLGGG (SEQ ID NO:19).

Methods of alignment of nucleotide and amino acid sequences for comparison are well known in the art. Thus, the determination of percent identity between any two sequences can be accomplished using a mathematical algorithm. Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (CGC), 575 Science Drive, Madison, Wis., USA). Alignments using these programs can be performed using the default programs. The CLUSTAL program is well described by Higns et al., 1988, Higgins et al., 1989, Corpet et al. 1988, Huang et al. 1992, and Pearson et al., 1994. Softeware for performing BLAST analyses is publicly available through the National Center for Biotechnology Information ( ). For purposes of the present invention, comparison of amino acid and nucleotide sequences for determination of percent sequence identity to the nucleotide and amino acid sequences of FAO1 and FAO2, is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

Another way of describing isolated nucleic acid molecules encoding a subject FAO is in terms of hybridization to the coding sequences (ORFs) of the subject FAO1 (SEQ ID NO:2) and FAO2a and FAO2b genes (SEQ ID NOs: 4 and 6, respectively). Thus in accordance with the present invention, there is provided a nucleic acid molecule which hybridizes under medium to high stringency conditions to the coding sequence of the subject FAO1 gene i.e., nucleotides 1941–4054 of the nucleotide sequence set forth in SEQ ID NO:1 and which also encodes the signature motif CGFCYLGC (SEQ ID NO:13). Preferably, the nucleic acid molecule which hybridizes under medium to high stringency conditions to the coding sequence of the subject FAO1 gene and encodes the signature motif CGFCYLGC (SEQ ID NO:13), comprises the nucleotide sequence:

```
TGY GGN TTY TGY TAY YTN GGN TGY (SEQ ID NO:32)
```

wherein:

R is A or G, Y is C or T, M is A or C, K is G or T, S is G or C, W is A or T, H is A or T or C, B is G or T or C, D is G or A or T, N is A or G, or C or T.

The present invention further provides a nucleic acid molecule which hybridizes under medium to high stringency conditions to the coding sequence of the subject FOA2a gene, i.e., nucleotides 1521–3635 of SEQ ID NO:3, or FAO2b gene, i.e., nucleotides 1099–3213 of SEQ ID NO:5, and which also encodes the signature motif IIGSGAGAGVMA (SEQ ID NO:14) and/or CGFCYLGC (SEQ ID NO:13) and/or AGSTLGGG (SEQ ID NO:19). Preferably, the nucleic acid molecule which hybridizes under medium to high stringency conditions to the coding sequence of a subject FAO2a or FAO2b gene and encodes the signature motif IIGSGAGAGVMA (SEQ ID NO:14) and/or and/or CGFCYLGC (SEQ ID NO:13) and/or AGSTLGGG (SEQ ID NO:19), comprises the nucleotide sequence:

```
                                          (SEQ ID NO:33)
ATH ATH GGN WSN GGN GCN GGN GCN GGN GTN AUG GCN
and/or
                                          (SEQ ID NO:32)
        TGY GGN TTY TGY TAY YTN GGN TGY
and/or
                                          (SEQ ID NO:34)
        GCN GGN WSN ACN YTN GGN GGN GGN
```

wherein:

R is A or G, Y is C or T, M is A or C, K is G or T, S is G or C, W is A or T,H is A or T or C, B is G or T or C, D is G or A or T, N is A or G, or C or T.

As used herein, hybridization under medium or high stringency conditions are as described in Maniatis et al. 1982 *Molecular Cloning*, Cold Spring Harbor Laboratory, N.Y., at pages 387–389, and especially pragraph 11 which is incorporated by reference herein as if fully set forth. A low stringency is defined as being in 4–6 S×SSC/1% (w/v) SDS at 37–45° C. for 2–3 hours. Medium stringency conditions are considered herein to be 1–4×SSC/0.5%–1% (w/v) SDS at greater than or equal to 45° C. for 2–3 hours. High stringency conditions are considered herein to be 0.1–1×SSC/0.1%–1% (w/v) SDS at greater than or equal to 60° C. for 1–3 hours. As used herein, medium to high stringency conditions refer to conditions which are either medium stringency conditions, high stringency conditions, or conditions between medium and high stringency. Preferably, an isolated nucleic acid molecule which hybridizes to the ORF of the subject FAO1 or FAO2 genes, hybridizes under high stringency conditions.

The present invention further provides a vector comprising a nucleotide sequence encoding FAO1 having the amino acid sequence as set forth in SEQ ID NO:2. In a preferred embodiment, the vector comprises an FAO1 gene having a nucleotide sequence as set forth in SEQ ID NO:1. Also provided is a vector comprising a nucleotide sequence encoding FAO2a having the amino acid sequence as set forth in SEQ ID NO:4. Preferably, the vector comprises an FAO2a gene having a nucleotide sequence as set forth in SEQ ID NO:3. Still further provided is a vector comprising a nucleotide sequence encoding FAO2b having the amino acid sequence as set forth in SEQ ID NO:6. Preferably, the vector comprises an FAO2b gene having a nucleotide sequence as set forth in SEQ ID NO:5.

In accordance with the present invention, any of the nucleic acid sequences hereinbefore described may be incorporated into a vector. In addition, it should be understood that a vector may also comprise an open reading frame for both an FAO1 and FAO2 gene, as well as fragments thereof.

A host cell is also provided which is transfected or transformed with a nucleic acid molecule encoding a subject FAO1 and/or FAO2a and/or FAO2b. For example, a host cell may be transfected or transformed with a nucleic acid molecule encoding an amino acid sequence as set forth in any of SEQ ID NOs: 2, 4, or 6. Preferably, the host cell is transformed with a nucleic acid molecule encoding an FAO1 gene comprising the nucleotide sequence depicted in SEQ ID NO:1. In another preferred embodiment, the host cell is transformed with a nucleic acid molecule encoding an FAO2a gene comprising the nucleotide sequence depicted in SEQ ID NO:3. In still another preferred embodiment, the host cell is transformed with a nucleic acid molecule encoding an FAO2b gene comprising the nucleotide sequence depicted in SEQ ID NO:5. It should be understood that the present invention also encompasses host cells transfected or transformed with any of the nucleic acid sequences hereinbefore described.

Depending upon the host cell transformed with a subject FAO2a or FAO2b gene, the CUG codon in mRNA corresponding to nucleotide positions 2049–2051 of SEQ ID NOs: 3 and 5 will be translated differently. For example, while CUG codons are translated as serine in *C. tropicalis* other host organisms follow the universal code and translate CUG codons as leucine. Therefore, in order to ensure that the mRNA codon corresponding to nucleotide positions 2049–2051 of SEQ ID No:3 and nucleotide positions 1627–1629 in SEQ ID No:5 in a subject FAO2 gene is translated to serine in a host cell other than *C. tropicalis*, such codon should be one which is translated to serine following the universal code. Examples of such codons include UCU, UCC, UCA, UCG, AGU, and AGC. Methods of altering DNA sequence (and therefore codons in corresponding transcribed mRNA sequence) are well known in the art and include e.g., various in vitro mutagenesis techniques. There are various commercially available kits particularly suited for this application such as the T7-Gen in vitro mutagenesis Kit (USB, Cleveland, Ohio). Alternatively, PCR technology may be employed to alter nucleotide sequence. If an FAO2 gene is chemically synthesized, nucleotide sequence corresponding to positions 2049–2051 of SEQ ID NOs: 3 and 5 can be synthesized as DNA which transcribes a codon translatable to serine following the universal code, e.g., incorporating DNA sequence corresponding to those codons listed above.

In a preferred embodiment of the invention, an isolated nucleic acid molecule which encodes FAO1 is manipulated so that the native FAO1 gene promoter is removed and a promoter from another gene is operably linked to the FAO1 gene coding sequence. Similarly, an isolated nucleic acid molecule which encodes FAO2 is preferably manipulated so that the native FAO2 gene promoter is removed and a promoter from another gene is operably linked to the FAO2 gene coding sequence. The term "operably linked" refers to the association of nucleic acid sequences so that the function of one is affected by the other. A promoter is operably linked with an open reading frame of a gene, when it is capable of affecting the expression of the open reading frame (ORF) (i.e., the ORF is under the transcriptional control of the promoter.) Notwithstanding the presence of other sequences between the promoter and the ORF, it should be understood that a promoter may still be operably linked to the ORF.

Desirable promoters for substitution into an FAO1 or FAO2 gene include promoters which may be induced at various times during bioconversion in response to certain stimuli (e.g., stress, substrate, cell death) thereby leading to increased aldehyde production and increased dicarboxylic acid production at defined times during the bioprocess. Examples of promoters suitable for operably linking to the FAO1 or FAO2 open reading frames include e.g., CYP52A2A, CYP52A5A, and CYP52A1A (see U.S. Pat. No. 6,331,420, the disclosure of which is incorporated by reference herein as if fully set forth.) With respect to use of the CYP52A2A promoter, see also copending patent application Ser. No. 09/911,781, the disclosure of which is also incorporated by reference herein as if fully set forth. The CYP52A2A gene of *C. tropicalis* 20336 is one gene from a family of genes involved in the metabolism of oleic acid to produce oleic dicarboxylic acid. The level of transcriptional induction of this gene in an oleic acid fermentation is many fold (>25) above other members of the same family. Example 6 herein describes the making of fusions between the CYP52A2A gene promoter and the ORF of FAO1 and FAO2 genes. Promoters from *Candida* β-oxidation genes such as POX 4 or POX 5 may also be operably linked to an ORF frame of an FAO1 or FAO2 gene. Preferably, a CYP52A2A gene promoter is used to drive expression of an FAO1 or FAO2 gene.

Thus, in accordance with the present invention, there is provided a nucleotide sequence for an open reading frame (ORF) of a gene encoding an FAO having the amino acid sequence as set forth in SEQ ID NO:2, wherein the ORF is operably linked to a heterologous promoter. Preferably, a nucleotide sequence for an ORF encoding an FAO operably linked to a heterologous promoter comprises nucleotides 1941–4054 of the nucleotide sequence set forth in SEQ ID NO:1.

Similarly, there is provided a nucleotide sequence for an open reading frame (ORF) of an FAO having the amino acid sequence as set forth in SEQ ID NO:4 (FAO2a) or SEQ ID NO:6 (FAO2b), wherein the ORF is operably linked to a heterologous promoter. Preferably, a nucleotide sequence for an ORF encoding an FAO operably linked to a heterologous promoter comprises either nucleotides 1521–3635 of the nucleotide sequence set forth in SEQ ID NO:3 or nucleotides 1099–3213 of the nucleotide sequence set forth SEQ ID NO:5. As used herein, the term "heterologous promoter" is meant to include a promoter other than the native promoter associated with a particular FAO coding sequence. These nucleotide sequences can therefore also be described as chimeric genes.

In another aspect of the invention, there is provided an expression vector comprising a nucleotide sequence encoding an FAO1 or FAO2 gene operably linked to a heterologous promoter sequence. The term "expression vector" is used broadly herein and is intended to encompass any medium which includes a nucleic acid molecule and which can be used to transform a target cell. Expression vectors thus encompass all the examples of vectors listed herein including integration vectors. Examples of expression vectors include but are not limited to plasmids, phagemids, phage, cosmids, yeast artificial chromosomes or linear DNA vectors. Examples of plasmids include but are not limited to e.g., yeast episomal plasmids or yeast replication plasmids.

A method of producing an FAO1 protein including an amino acid sequence as set forth in SEQ ID NO:2 is also provided. The method comprises the steps of (a) transforming a suitable host cell with a DNA sequence that encodes a protein having the amino acid sequence as set forth in SEQ ID NO:2; and (b) culturing the cell under conditions favoring the expression of the protein.

A method of producing an FAO2a protein including an amino acid sequence as set forth in SEQ ID NO:4 is also provided. The method comprises the steps of (a) transforming a suitable host cell with a DNA sequence that encodes a protein having the amino acid sequence as set forth in SEQ ID NO:4; and (b) culturing the cell under conditions favoring expression of the protein.

A method of producing an FAO2b protein including an amino acid sequence as set forth in SEQ ID NO:6 is also provided. The method comprises the steps of (a) transforming a suitable host cell with a DNA sequence that encodes a protein having the amino acid sequence as set forth in SEQ ID NO:6; and (b) culturing the cell under conditions favoring the expression of the protein In another aspect of the invention, there is provided a method for increasing production of an aldehyde during the second step of the ω-oxidation pathway of fatty acids. The method comprises the steps of: (a) providing a host cell having a naturally occurring number of FAO genes; (b) increasing, in the host cell, the number of FAO1 genes which encode an FAO1 protein having the amino acid sequence as set forth in SEQ ID NO:2; and (c) culturing the host cell in media containing an organic substrate which upregulates the FAO1 gene, to effect increased production of an aldehyde. Preferably, the FAO1 gene comprises nucleotides 1941–4054 of the nucleotide sequence as set forth in SEQ ID NO:1.

A method for increasing production of an aldehyde during the second step of the ω-oxidation pathway of fatty acids may also comprise the steps of: (a) providing a host cell having a naturally occurring number of FAO genes; (b) increasing, in the host cell, the number of FAO2 genes which encode an FAO2a protein having the amino acid sequence as set forth in SEQ ID NO:4; and (c) culturing the host cell in media containing an organic substrate which upregulates the FAO2 gene, to effect increased production of an aldehyde. Preferably, the FAO2a gene comprises nucleotides 1521–3635 of the nucleotide sequence as set forth in SEQ ID NO:3.

Alternatively, a method for increasing production of an aldehyde during the second step of the ω-oxidation pathway of fatty acids comprises the steps of: (a) providing a host cell having a naturally occurring number of FAO genes; (b) increasing, in the host cell, the number of FAO2 genes which encode an FAO2b protein having the amino acid sequence as set forth in SEQ ID NO:6; and (c) culturing the host cell in media containing an organic substrate which upregulates the FAO2b gene, to effect increased production of an aldehyde. Preferably, the FAO2b gene comprises nucleotides 1099–3213 of the nucleotide sequence as set forth in SEQ ID NO:5.

In another aspect of the invention, there is provided a method for increasing production of a dicarboxylic acid. The method comprises the steps of: (a) providing a host cell having a naturally occurring number of FAO genes; (b) increasing, in the host cell, the number of FAO1 genes which encode an FAO1 protein having the amino acid sequence as set forth in SEQ ID NO:2; and (c) culturing the host cell in media containing an organic substrate which upregulates the FAO1 gene, to effect increased production of dicarboxylic acid. Preferably, the FAO1 gene comprises nucleotides 1941–4054 of the nucleotide sequence as set forth in SEQ ID NO:1.

Alternatively, a method for increasing production of a dicarboxylic acid comprises the steps of: (a) providing a host cell having a naturally occurring number of FAO genes; (b) increasing, in the host cell, the number of FAO2a genes which encode an FAO2 protein having the amino acid sequence as set forth in SEQ ID NO:4; and (c) culturing the host cell in media containing an organic substrate which upregulates the FAO2a gene, to effect increased production of dicarboxylic acid. Preferably, the FAO2a gene comprises nucleotides 1521–3635 of the nucleotide sequence as set forth in SEQ ID NO:3.

Alternatively, a method for increasing production of a dicarboxylic acid comprises the steps of: (a) providing a host cell having a naturally occurring number of FAO genes; (b) increasing, in the host cell, the number of FAO2b genes which encode an FAO2 protein having the amino acid sequence as set forth in SEQ ID NO:6; and (c) culturing the host cell in media containing an organic substrate which upregulates the FAO2b gene, to effect increased production of dicarboxylic acid. Preferably, the FAO2b gene comprises nucleotides 1099–3213 of the nucleotide sequence as set forth in SEQ ID NO:5.

A method for increasing the production of an FAO1 protein having an amino acid sequence as set forth in SEQ ID NO:2 is further provided. The method comprises the steps of: (a) transforming a host cell having a naturally occurring level of FAO1 protein with an increased copy number of an FAO1 gene that encodes the FAO1 protein having the amino acid sequence as set forth in SEQ ID NO:2 and (b) culturing the cell and thereby increasing expression of the protein compared with that of a host cell containing a naturally occurring copy number of the FAO1 gene.

A method for increasing the production of an FAO2 protein having an amino acid sequence as set forth in SEQ ID NO:4 or 6 is also provided. The method comprises the steps of: (a) transforming a host cell having a naturally occurring amount of FAO2 protein with an increased copy number of an FAO2 gene that encodes the FAO2 protein having the amino acid sequence as set forth in SEQ ID NO:4 or 6; and (b) culturing the cell and thereby increasing expression of the protein compared with that of a host cell containing a naturally occurring copy number of the FAO2 gene.

In addition to amplifying the FAO genes to improve diacid productivity and decrease ω-hydroxy fatty acid formation, the FAO genes can be used to create knockout constructs to disrupt the native FAO genes in *Candida tropicalis*. Methods for making knockout constructs and use of the same for gene disruption are well known in the art. The disruption of native FAO genes in *C. tropicalis* block the diacid pathway at that step and allow for a build-up of α,ω-dihydroxy compounds when utilizing alkane substrates and ω-hydroxy fatty acids when using fatty acid substrates.

The present invention provides additional methods for increasing production of an aldehyde from an alcohol during the second step of the ω-oxidation pathway of fatty acids and ultimately, for increasing production of dicarboxylic acid. For example, a method for increasing production of an aldehyde during the second step of the ω-oxidation pathway of fatty acids comprises the steps of: (a) isolating a nucleic acid molecule comprising coding sequence for an FAO1 gene; (b) isolating a promoter sequence from a gene which transcribes at a higher rate than the FAO1 gene; (c) operably linking the promoter sequence to the open reading frame (ORF) of the FAO1 gene to create a fusion gene; (d) inserting the fusion gene into an expression vector; (e) transforming a host cell with the expression vector and (f) culturing the transformed host cell in a media containing an organic substrate that is biooxidizable to a mono- or polycarboxylic acid. Preferably, the nucleic acid molecule encodes an FAO1 comprising the amino acid sequence set forth in SEQ ID NO:2. Preferably, the organic substrate is an ω-hydroxy fatty acid.

Production of an aldehyde from an alcohol during the second step of the ω-oxidation pathway of fatty acids may also be increased by: (a) isolating a nucleic acid molecule comprising coding sequence for an FAO2 gene; (b) isolating a promoter sequence from a gene which transcribes at a higher rate than the FAO2 gene, (c) operably linking the promoter sequence to the open reading frame (ORF) of the FAO2 gene to create a fusion gene; (d) inserting the fusion gene into an expression vector; (e) transforming a host cell with the expression vector and (f) culturing the transformed host cell in a media containing an organic substrate that is biooxidizable to a mono- or polycarboxylic acid. Preferably, the FAO2 nucleic acid molecule encodes an FAO2 protein comprising the amino acid sequence as set forth in SEQ ID NOs:4 or 6.

Production of an ketone from an alcohol during the second step of the ω-oxidation pathway of fatty acids may also be increased by: (a) isolating a nucleic acid molecule comprising coding sequence for an FAO2 gene; (b) isolating a promoter sequence from a gene which transcribes at a higher rate than the FAO2 gene, (c) operably linking the promoter sequence to the open reading frame (ORF) of the FAO2 gene to create a fusion gene; (d) inserting the fusion gene into an expression vector; (e) transforming a host cell with the expression vector and (f) culturing the transformed host cell in a media containing an organic substrate that is biooxidizable to a mono- or polycarboxylic acid. Preferably, the organic substrate is a 2-alkanol. Preferably, the nucleic acid molecule encodes an FAO2 protein comprising the amino acid sequence as set forth in SEQ ID NOs:4 or 6.

In accordance with the methods of the present invention, dicarboxylic acid production may be increased by: (a) isolating a nucleic acid molecule comprising coding sequence for an FAO1 gene; (b) isolating a promoter sequence from a gene which transcribes at a higher rate than the FAO1 gene; (c) operably linking the promoter sequence to the open reading frame (ORF) of the FAO1 gene to create a fusion gene; (d) inserting the fusion gene into an expression vector; (e) transforming a host cell with the expression vector and (f) culturing the transformed host cell in a media containing an organic substrate that is biooxidizable to a mono- or polycarboxylic acid. Preferably, the ORF of the FAO1 gene comprises nucleotides 1941–4054 of the nucleotide sequence set forth in SEQ ID NO:1. Preferably, the organic substrate is an ω-hydroxy fatty acid.

Dicarboxylic acid production may also be increased by: (a) isolating a nucleic acid molecule comprising coding sequence for an FAO2 gene; (b) isolating a promoter sequence from a gene which transcribes at a higher rate than the FAO2 gene, (c) operably linking the promoter sequence to the open reading frame (ORF) of the FAO2 gene to create a fusion gene; (d) inserting the fusion gene into an expression vector; (e) transforming a host cell with the expression vector and (f) culturing the transformed host cell in a media containing an organic substrate that is biooxidizable to a mono- or polycarboxylic acid. Preferably, the ORF of the FAO2 gene comprises nucleotides 1521–3635 of the nucleotide sequence as set forth in SEQ ID NO:3 or nucleotides 1099–3213 of the nucleotide sequence set forth in SEQ ID NO:5.

It is to be understood, that in any of the methods disclosed herein, FAO1 and FAO2 may be separately produced in a host cell. Alternatively, both FAO1 and FAO2 may be produced in the same host cell. Thus for example, a host cell may be transformed with: an expression vector comprising an FAO1 gene or fragment thereof, an expression vector comprising an FAO2a gene or fragment thereof, an expression vector comprising an FAO2b gene or fragment thereof, an expression vector comprising both an FAO1 and/or and FAO2a gene or fragment thereof and/ or an FAO2b gene or fragment(s) thereof, or any combination of such vectors.

It should be understood that host cells into which one or more copies of desired FAO1 and/or FAO2 genes (including FAO chimeric genes comprising an FAO1 or FAO2 gene operably linked to a heterologous promoter) have been introduced can be made to include such genes by any technique known to those skilled in the art. For example, suitable host cells include procaryotes such as *Bacillus* sp., *Pseudomous* sp., *Actinomycetes* sp., *Eschericia* sp., *Mycobacterium* sp., and eukaryotes such as yeast, algae, insect cells, plant cells and filamentous fungi. Suitable host cells are preferably yeast cells such as *Yarrowia, Bebaromyces, Saccharomyces, Schizosaccharomyces*, and *Pichia* and more preferably those of the *Candida* genus. Preferred species of *Candida* are *tropicalis, maltosa, apicola, paratropicalis, albicans, cloacae, guillermondii, intermedia, lipolytica, parapsilosis* and *zeylenoides*. Particularly preferred hosts include *C. tropicalis* strains that have been genetically modified so that one or more of the chromosomal POX4A, POX4B and both POX5 genes have been disrupted as described, e.g., in U.S. Pat. Nos. 5,254,466 and 5,620,878, each incorporated herein by reference as if fully set forth. Such disruption blocks the β-oxidation pathway. Examples of β-oxidation blocked strains of *C. tropicalis* include H41, H41B, H51, H45, H43, H53, H534, H534B, H435 and H5343 (ATCC 20962) as described in aforementioned U.S. Pat. No. 5,254,466.

Vectors such as plasmids, phagemids, phages or cosmids can be used to transform or transfect suitable host cells. Host cells may also be transformed by introducing into a cell a linear DNA vector(s) containing the desired gene sequence. Such linear DNA may be advantageous when it is desirable to avoid introduction of non-native (foreign) DNA into the cell. For example, DNA consisting of a desired target gene(s) flanked by DNA sequences which are native to the cell can be introduced into the cell by electroporation, lithium acetate transformation, spheroplasting and the like. Flanking DNA sequences can include selectable markers and/or other tools for genetic engineering.

A suitable organic substrate for use in the methods described herein can be any organic compound that is biooxidizable to a mono- or polycarboxylic acid (or any compound that is biooxidizable to a ketone group for the methods described herein directed to production of a ketone). Such a compound can be any saturated or unsaturated aliphatic compound or any carbocyclic or heterocyclic aromatic compound having at least one terminal methyl group, a terminal carboxyl group and/or a terminal functional group which is oxidizable to a carboxyl group by biooxidation. A terminal functional group which is a derivative of a carboxyl group may be present in the substrate molecule and may be converted to a carboxyl group by a reaction other than biooxidation. For example, if the terminal group is an ester that neither the wild-type *C. tropicalis* nor the genetic modifications described herein will allow hydrolysis of the ester functionality to a carboxyl group, then a lipase can be added during the fermentation step to liberate free fatty acids. Suitable organic substrates include, but are not limited to, saturated fatty acids, unsaturated fatty acids, alkanes, alkenes, alkynes and combinations thereof.

Alkanes are a type of saturated organic substrate which are useful herein. The alkanes can be linear or cyclic, branched or straight chain, substituted or unsubstituted. Particularly preferred alkanes are those having from about 4 to about 25 carbon atoms, examples of which include but are not limited to butane, hexane, octane, nonane, dodecane, tridecane, tetradecane, octadecane and the like.

Examples of unsaturated organic substrates which can be used herein include but are not limited to internal olefins such as 2-pentene, 2-hexene, 3-hexene, 9-octadecene and the like; alpha olefins such as 1-dodecene, 1-octadecene, 1-tetradecene, and the like; unsaturated carboxylic acids such as 2-hexenoic acid and esters thereof, oleic acid and esters thereof including triglyceryl esters having a relatively high oleic acid content, erucic acid and esters thereof including triglyceryl esters having a relatively high erucic acid content, ricinoleic acid and esters thereof including triglyceryl esters having a relatively high ricinoleic acid content, linoleic acid and esters thereof including triglyceryl esters having a relatively high linoleic acid content; unsaturated alcohols such as 3-hexen-1-ol, 9-octadecen-1-ol, saturated alcohols such as 2-decanol, 2-undecanol, 2-dodecanol, 2-hexadecanol, 10-undecen-1-ol; 1,2-octanediol; 1,10--decanediol; 1,2-dodecanediol; 1,16-hexadecanediol; 10-hydroxydecanoic acid; 12-hydroxydodecanoic acid; 16-hydroxydodecanoic acid and the like; unsaturated aldehydes such as 3-hexen-1-al, 9-octadecen-1-al and the like. In addition to the above, an organic substrate which can be used herein include alicyclic compounds having at least one internal carbon-carbon double bond and at least one terminal ethyl group, and/or a terminal functional group which is oxidizable to a carboxyl group by biooxidation.

The organic substrate can also contain other functional groups that are biooxidizable to carboxyl groups such as an aldehyde or alcohol group. The organic substrate can also contain other functional groups that are not biooxidizable to carboxyl groups and do not interfere with the biooxidation such as halogens, ethers, and the like.

Examples of saturated fatty acids which may be applied to cells incorporating the present FAO1 and FAO2 genes include caproic, enanthic, caprylic, pelargonic, capric, undecylic, lauric, myristic, pentadecanoic, palmitic, margaric, stearic, arachidic, behenic acids and combinations thereof. Examples of unsaturated fatty acids which may be applied to cells incorporating the present FAO1 and FAO2 genes include palmitoleic, oleic, erucic, linoleic, linolenic acids and combinations thereof. Alkanes and fractions of alkanes may be applied which include chain links from C12 to C24 in any combination. An example of a preferred fatty acid mixture is High Oleic Sun Flower Fatty Acid (HOSFFA). HOSFFA is a fatty acid mixture containing approximately 80% oleic acid and is commercially available from Cognis Corporation as Edenor®. Emersol® is another HOSFFA commercially available from Cognis Corporation.

The invention is further illustrated by the following specific examples which are not intended in any way to limit the scope of the invention.

EXAMPLE 1

Materials and Methods

Transformation of *C. tropicalis* Using Lithium Acetate

The following protocol was used to transform *C. tropicalis* in accordance with the procedures described in *Current Protocols in Molecular Biology*, Supplement 5, 13.7.1 (1989) Frederick M. Ausubel, Roger Brent, Robert E. Kingston, David D. Moore, J. G. Seidman, John A. Smith, and Kevin Struhl, eds., John Wiley and Sons, Hoboken, N.J. 5 ml of YEPD was inoculated with *C. tropicalis* H5343 ura- and incubated overnight on a New Brunswick shaker at 30° C. and 170 rpm. The next day, the overnight culture was used to inoculate 50 ml YEPD at an $OD_{600}$ of 0.2 and growth was continued at 30° C., 170 rpm. The cells were harvested at an $OD_{600}$ of 1.0. The culture was transferred to a 50 ml polypropylene tube and centrifuged at 1000×g for 10 min. The cell pellet was resuspended in 10 ml sterile TE (10 mM Tris-Cl and 1 mM EDTA, pH 8.0). The cells were again centrifuged at 1000×g for 10 min and the cell pellet was resuspended in 10 ml of a sterile lithium acetate solution (LiAc (0.1 M lithium acetate, 10 mM Tris-Cl, pH 8.0, 1 mM EDTA). Following centrifugation at 1000×g for 10 min., the pellet was resuspended in 0.5 ml LiAc. This solution was incubated for 1 hr at 30° C. while shaking gently at 50 rpm. A 0.1 ml aliquot of this suspension was incubated with 15–20 μg of transforming DNA at 30° C. with no shaking for 30 min. A 0.7 ml PEG solution (40% wt/vol polyethylene glycol 3340, 0.1 M lithium acetate, 10 mM Tris-Cl, pH 8.0, 1 mM EDTA) was added and incubated at 30° C. for 45 min. The tubes were then placed at 42° C. for 10 min. A 0.2 ml aliquot was plated on synthetic complete media minus uracil (SC–uracil) (Kaiser et al. *Methods in Yeast Genetics*, Cold Spring Harbor Laboratory Press, USA, 1994). Growth of transformants was monitored for 5 days. After three days, several transformants were picked and transferred to SC–uracil plates for genomic DNA preparation and screening.

Fermentations

Fermentations were performed using High Oleic Sun Flower Fatty Acid (HOSFFA) as the substrate, with glucose used as the co-substrate. The HOSFFA used was approximately 85% oleic acid (84.45% oleic acid, 5.24% linoleic acid, 4.73% stearic acid, 3.87% palmitic acid, 1.71% other fatty acids). Fermentation runs had both a growth and a bioconversion phase. Cells were grown on glucose at 35° C. to an absorbance at 600 nm of 50 to 60. When the growth phase was completed as determined by a sharp rise in dissolved oxygen, the cells were immediately switched to the bioconversion phase, which was performed at a temperature of 30° C. A slow glucose feed (0.87 g/L/h from 0 to 42 h and 0.7 g/L/h thereafter) was used to supply energy. At the same time a small charge of HOSFFA (0.55% v/v) was added to the fermentation. Feeding of substrate (average feed rate of 1.6 g/L/h) continued during the remainder of the fermentation. H5343 is the base strain derived from *Candida tropicalis* ATCC 20336) blocked for β-oxidation, which has had the POX4 and POX5 genes disrupted by insertional mutagenesis. Strain HDC23-3 is an H5343 base strain that is amplified for a cytochrome P450 monoxygenase gene, CYP52A2, and the cytochrome P450 reductase (NCP) gene, both genes having been cloned from *C. tropicalis* ATCC 20336.

FAO Activity Profile during HOSFFA Fermentations

Washing of Cells

HDC23-3 cells from several fermentation runs, and taken at different time points in the fermentation runs, were prepared and assayed for FAO activity. Due to the high levels of solid diacid in the broth, particularly in samples taken later in the fermentation, the samples had to be washed extensively to remove the diacid prior to making extracts. Since frozen samples were found to lose a lot of enzyme activity (after washing and preparation of extracts), freshly sampled fermentation broth was placed on ice until ready for washing. This sample was thoroughly mixed and a 20 ml sample was removed. This sample was centrifuged (Sorvall RT6000B Refrigerated Centrifuge) at approximately 1,500×g (H1000B rotor at 2500 rpm) for 5 minutes to pellet the cells. The supernatant was decanted, and the cells were resuspended in 40 ml of 50 mM HEPES buffer, pH 7.6. The sample was centrifuged at 1,500×g for only one minute, which pelleted the yeast cells, but allowed the less dense diacid product to "float" in the supernatant. The supernatant was decanted and the cells were washed again in 40 ml of buffer. After the second washing step, the cell pellet was examined for any sign of residual diacid, evidenced by a white precipitate on top of the cell pellet, or patches of white color in the cell pellet itself. Washing was repeated until the pellet was completely clear of all diacid and the cell pellet was a pale tan color throughout. During the course of the fermentation, as the cells produced more diacid, more washing steps were needed to free the cell pellet of diacid.

Preparation of Cell-Free Extracts

After washing away the diacid, the cell pellet was resuspended in 10 ml of 50 mM potassium phosphate buffer with 20% glycerol, pH 7.6 (phosphate-glycerol buffer) for a two-fold concentration of cellular enzymes. 100 µl of a 100 mM solution of the serine-protease inhibitor, phenylmethylsulfonyl fluoride (PMSF) in isopropanol, was added for a final concentration of 1 mM. The cells were then broken by passing the sample three times through a chilled French pressure cell (SLM Instruments, Inc. French Pressure Cell Press) at approximately 20,000 psig. The sample was stored on ice before, during and after breakage of the cells to prevent the loss of enzyme activity. This broken cell suspension was then centrifuged at approximately 37,000×g for 30 minutes to pellet the cellular debris, leaving the cellular enzymes in the supernatant. The supernatant (cell-free extract) was removed and saved to perform enzyme assays. During assays, this cellular extract was always kept on ice, and was stored at −20° C. between sets of assays to preserve enzyme activity.

FAO Enzyme Assay

The assay procedure used is a modification of an assay used by Kemp et al (1). The assay is a two-enzyme coupled reaction. Dodecanol was used as the substrate for the FAO, which oxidizes the dodecanol to dodecanal. At the same time it reduces molecular oxygen to hydrogen peroxide. A second enzyme in the reaction mixture, peroxidase derived from horseradish (HRP), uses electrons obtained by oxidizing hydrogen peroxide to reduce 2,2'-azino-bis(3-ethylbenzthiazoline-6-sulfonic acid) (ABTS) in the reaction mixture. Reduced ABTS absorbs strongly at 405 nm. The quality of HRP is important, since it has been observed that commercially obtained preparations vary in quality. It is necessary, therefore, to obtain preparations of highest purity. The HRP (Sigma #P8415) was made at a concentration of 2 mg/ml (≈250 units/mg) in 50 mM potassium phosphate buffer, pH 7.6. In experiments in which the amount of horseradish peroxidase was varied in the reaction mixture, it was found that 5 µl of this solution in a one ml reaction mixture was sufficient to obtain maximal velocity.

The final reaction mixture (1.0 ml) for the general alcohol oxidase assay consisted of: 500 µl of 200 mM HEPES buffer, pH 7.6; 50 µl of a 10 mg/ml ABTS solution in deionized water; 10 µl of a 5 mM solution of dodecanol in acetone; and 5 µl of a 2 mg/ml horseradish peroxidase solution in 50 mM potassium phosphate buffer, pH 7.6. After adding the extract, the activity was generally read at 405 nm for one minute at room temperature. The amount of extract that was added to the reaction mixture was varied so that the activity fell within the range of 0.2 to 1.0 $\Delta A^{405\ nm}$/min. Alcohol oxidase activity was reported as specific activity units/mg protein (1 unit=µmole substrate oxidized/min). An extinction coefficient at 405 nm of 18.4 was used for ABTS and was equivalent to 0.5 mM oxidized substrate. In certain substrate-specificity experiments, 200 mM HEPES buffer, pH 7.6, containing 0.5% Triton X100 was used in place of the 200 mM HEPES buffer in the reaction mixture described above. The detergent aided in solubilizing some of the more water-insoluble substrates tested.

Preparation of Microsomes

Microsomes were prepared from *Candida tropicalis* cell-free extracts by centrifugation at 100,000×g for one hour at 4° C. The FAO was found within the pelleted microsomes. Catalase, a soluble enzyme, remained in the supernatant, which allowed the separation of these two enzymes. The supernatant was removed and assayed for FAO and catalase activity. The microsomal pellet was resuspended in an equivalent amount of phosphate-glycerol buffer, after which it was also assayed for catalase and FAO activity. Microsomes from Escherichia coli were prepared in the same manner.

Protein Determination

Protein concentration in the extracts was determined. The Lowry method of determining protein concentration gave much higher results than expected, and were inconsistent between protein determinations of the same samples. For this reason, a new procedure was performed using the Bradford Reagent (Sigma, #B6916) and following the protocol provided by the supplier.

EXAMPLE 2

Cloning of Fatty Alcohol Oxidase Genes

Preparation of Genomic DNA 50 ml of YPD broth (Difco) was inoculated with a single colony of *C. tropicalis* 20336 from a YPD agar (Difco) plate and was grown overnight at 30° C. 5 ml of the overnight culture was inoculated into 100 ml of fresh YPD broth and incubated at 30° C. for 4 to 5 hr with shaking. Cells were harvested by centrifugation, washed twice with sterile distilled water and resuspended in 4 ml of spheroplasting buffer (1 M Sorbitol, 50 mM EDTA, 14 mM mercaptoethanol) and incubated for 30 min at 37° C. with gentle shaking. 0.5 ml of 2 mg/ml zymolyase (ICN Pharmaceuticals, Inc., Irvine, Calif.) was added and incubated at 37° C. with gentle shaking for 30 to 60 min. Spheroplast formation was monitored by SDS lysis. Spheroplasts were harvested by brief centrifugation (4,000 rpm, 3 min) and were washed once with the spheroplast buffer without mercaptoethanol. Harvested spheroplasts were then suspended in 4 ml of lysis buffer (0.2 M Tris/pH 8.0, 50 mM EDTA, 1% SDS) containing 100 mg/ml RNase (Qiagen Inc., Chatsworth, Calif.) and incubated at 37° C. for 30 to 60 min.

Proteins were denatured and extracted twice with an equal volume of chloroform/isoamyl alcohol (24:1) by gently mixing the two phases by hand inversions. The two phases were separated by centrifugation at 10,000 rpm for 10 min and the aqueous phase containing the high-molecular weight DNA was recovered. NaCl was added to the aqueous layer to a final concentration of 0.2 M and the DNA was precipitated by adding 2 volumes of ethanol. Precipitated DNA was spooled with a clean glass rod and resuspended in TE buffer (10 mM Tris/pH 8.0, 1 mM EDTA) and allowed to dissolve overnight at 4° C. To the dissolved DNA, RNase free of any DNase activity (Qiagen Inc., Chatsworth, Calif.) was added to a final concentration of 50 mg/ml and incubated at 37° C. for 30 min. Then protease (Qiagen Inc., Chatsworth, Calif.) was added to a final concentration of 100 mg/ml and incubated at 55 to 60° C. for 30 min. The solution was extracted once with an equal volume of phenol/chloroform/isoamyl alcohol (25:24:1) and once with equal volume of chloroform/isoamyl alcohol (24:1). To the aqueous phase 0.1 volumes of 3 M sodium acetate and 2 volumes of ice cold ethanol (absolute) were added and the high molecular weight DNA was spooled with a glass rod and dissolved in 1 to 2 ml of TE buffer.

Library Preparation

A genomic library was constructed using λ ZAP Express™ vector (Stratagene, La Jolla, Calif.). Genomic DNA was partially digested with Sau3A1 and fragments in the range of 6 to 12 kb were purified from an agarose gel after electrophoresis of the digested DNA. These DNA fragments were then ligated to BamHI digested λ ZAP Express™ vector arms according to manufacturer's protocols. Three ligations were set up to obtain approximately $9.8\times10^5$ independent clones. All three libraries were pooled and amplified according to manufacturer instructions to obtain high-titer (>$10^9$ plaque forming units/ml) stock for long-term storage. The titer of packaged phage library was ascertained after infection of *E. coli* XL1Blue-MRF' cells. *E. coli* XL1Blue-MRF' were grown overnight in either in LB medium (Difco) or NZCYM (Difco) containing 10 mM $MgSO_4$ and 0.2% maltose at 37° C. or 30° C., respectively with shaking. Cells were then centrifuged and resuspended in 0.5 to 1 volume of 10 mM $MgSO_4$. 200 µl of this *E. coli* culture was mixed with several dilutions of packaged phage library and incubated at 37° C. for 15 min. To this mixture 2.5 ml of LB top agarose or NZCYM top agarose (maintained at 60° C.) was added and plated on LB agar (Difco) or NCZYM agar (Difco) present in 82 mm petri dishes. Phage were allowed to propagate overnight at 37° C. to obtain discrete plaques and the phage titer was determined.

Screening Genomic Libraries (Plaque Form)

λ Library Plating

*E. coli* XL1Blue-MRF' cells were grown overnight in LB medium (25 ml) containing 10 mM $MgSO_4$ and 0.2% maltose at 37° C., 250 rpm. Cells were then centrifuged (2200×g for 10 min) and resuspended in 0.5 volumes of 10 mM $MgSO_4$. 500 µl of this *E. coli* culture was mixed with a phage suspension containing 25,000 amplified lambda phage particles and incubated at 37° C. for 15 min. To this mixture 6.5 ml of NZCYM top agarose (maintained at 60° C.) was added and plated on 80–100 ml NCZYM agar present in a 150 mm petri dish. Phage were allowed to propagate overnight at 37° C. to obtain discrete plaques. After overnight growth, plates were stored in a refrigerator for 1–2 hrs before plaque lifts were performed.

Plaque Lift

Magna Lift™ nylon membranes (Micron Separations, Inc., Westborough, Mass.) were placed on the agar surface in complete contact with plaques and transfer of plaques to nylon membranes was allowed to proceed for 5 min at room temperature (RT). After plaque transfer the membrane was placed on 2 sheets of Whatman 3M™ (Whatman, Hillsboro, Oreg.) filter paper saturated with a 0.5 N NaOH, 1.0 M NaCl solution and left for 10 min at room temperature (RT) to denature DNA. Excess denaturing solution was removed by blotting briefly on dry Whatman 3M™ paper. Membranes were then transferred to 2 sheets of Whatman 3M™ paper saturated with 0.5 M Tris-HCl (pH 8.0), 1.5 M NaCl and left for 5 min to neutralize. Membranes were then washed for 5 min in 200–500 ml of 2×SSC, dried by air and baked for 30–40 min at 80° C. The membranes were then probed with labeled DNA.

DNA Hybridizations

Membranes were prewashed with a 200–500 ml solution of 5×SSC, 0.5% SDS, 1 mM EDTA (pH 8.0) for 1–2 hr at 42° C. with shaking (60 rpm) to remove bacterial debris from the membranes. The membranes were prehybridized for 1–2 hrs at 42° C. (in a volume equivalent to 0.125–0.25 ml/$cm^2$ of membrane) with ECL Gold™ buffer (Amersham) containing 0.5 M NaCl and 5% blocking reagent. DNA fragments used as probes were purified from agarose gel using a QIAEX II™ gel extraction kit (Qiagen Inc., Chatsworth, Calif.) according to manufacturer's protocol and labeled using an Amersham ECL™ direct nucleic acid labeling kit (Amersham). Labeled DNA (5–10 ng/ml hybridization solution) was added to the prehybridized membranes and the hybridization was allowed to proceed overnight. The following day membranes were washed with shaking (60 rpm) twice at 42° C. for 20 min each time in (in a volume equivalent to 2 ml/$cm^2$ of membrane) a buffer containing either 0.1 (high stringency) or 0.5 (low stringency)×SSC, 0.4% SDS and 360 g/l urea. This was followed by two 5 min washes at room temperature in (in a volume equivalent to 2 ml/$cm^2$ of membrane) 2×SSC. signals were generated using the ECL™ nucleic acid detection reagent and detected using Hyperfilm ECL™ (Amersham).

Agar plugs that contained plaques corresponding to positive signals on the X-ray film were taken from the master plates using the broad-end of a sterile Pasteur pipette. Plaques were selected by aligning the plates with the x-ray film. At this stage, multiple plaques were generally taken. Phage particles were eluted from the agar plugs by soaking in 1 ml SM buffer (Sambrook et al., (1989) (*Molecular Cloning: A Laboratory Manual*, Cold Spring Harbor Laboratory Press, Cold Spring Harbor, N.Y.) overnight. The phage eluate was then diluted and plated with freshly grown *E. coli* XLlBlue-MRF' cells to obtain 100–500 plaques per 85 mm NCZYM agar plate. Plaques were transferred to Magna Lift nylon membranes as before and probed again using the same probe. Single well-isolated plaques corresponding to signals on X-ray film were picked by removing agar plugs and eluting the phage by soaking overnight in 0.5 ml SM buffer.

Conversion of λ Clones to Plamid Form

To convert the λ ZAP Express™ vector to plasmid form, *E. coli* strains XL1Blue-MRF' and XLOR were used. The conversion was performed according to the manufacturer's (Stratagene) protocols for single-plaque excision.

Generation of Probe for Library

Primer Selection

The probe for the library was prepared from a polymerase chain reaction (PCR) fragment of the *C. tropicalis* ATCC 20336 genome known to represent the FAO gene or genes. By comparing regions of homology between two published *C. cloacae* FAO genes and a published *C. tropicalis* (NCYC 470) FAOT gene (4), two non-degenerative primers were developed for the PCR: two forward primers designated as (FAO-F1) and (FAO-F2) and one reverse primer designated as (FAO-R1) (See Table I). These primers were anticipated to amplify a region in the gene in the open-reading frame (ORF) of the FAO gene.

TABLE 1

Comparison of Primer Sequence to Corresponding Sequence in *Candida cloacae*.

| Gene | Sequence Comparison | | Primer |
|---|---|---|---|
| *C. t.* FAOT | 352 5' **TCG TGG CGT GAC TCT CCT** 3' 369 | (SEQ ID NO:35) | FAO-F1 |
| *C. c.* FAO1 | 340 5' **TCA TGG** AGA **GAC TCT CCT** 3' 357 | (SEQ ID NO:36) | |
| *C. c.* FAO2 | 340 5' **TCA TGG** AGA **GAC TCT** CCA 3' 357 | (SEQ ID NO:37) | |
| *C. t.* FAOT | 608 5' **CTG GTG CTG GTG TAG T** 3' 623 | (SEQ ID NO:38) | FAO-F2 |
| *C. c.* FAO1 | 593 5' **CAG GAG CAG GTG TGG T** 3' 608 | (SEQ ID NO:39) | |
| *C. c.* FAO2 | 593 5' **CGG GAG CAG GAG TGG T** 3' 608 | (SEQ ID NO:40) | |
| *C. t.* FAOT | 1780 5' **TTG GTA CCC ATG CTT GTG G** 3' 1762 | (SEQ ID NO:41) | FAO-R1 |
| *C. c.* FAO1 | 1762 5' **TTG GTA CCC AAG CTT GTG G** 3' 1744 | (SEQ ID NO:42) | |
| *C. c.* FAO2 | 1762 5' **TTG GTA CCC AAG CTT GTA G** 3' 1744 | (SEQ ID NO:43) | |

PCR Conditions

The primers selected were used in a PCR reaction with the following conditions: 5 µl 10×PCR buffer, 5 µl either FAO-F1 or FAO-F2 primer stock (20 µM), 5 µl 30R1 primer stock (20 µM), 1 µl nucleotide mix, 0.5 µl Taq polymerase, and 1 µL genomic DNA from *Candida tropicalis* strain ATCC 20336, all in a 50 µl reaction volume. The reaction conditions were: 95° C. for 2 min, followed by 35 cycles of 95° C. for 30 sec, 53° C. for 30 sec and 72° C. for 1 min. The primer pair, FAO-F1 and FAO-R1, which should have yielded an expected 1429 bp fragment, never yielded a PCR product. The primer pair, FAO-F2 and FAO-R1, which should have yielded an expected 1173 bp fragment, generated a fragment approximately 1200 bp in length.

TOPO TA Cloning of PCR Product

The PCR product was cloned using a TOPO TA cloning kit (Invitrogen, Carlsbad, Ca., TOPO TA Cloning Kit, Version K2, #25-0184) into Top10F' strain cells. The PCR product was first purified by electrophoresis in low-melt agarose (1%) followed by excising the appropriate band. The gel slice was placed in a microfuge tube and incubated at 65° C. until the gel melted, after which it was placed at 37° C. In a fresh tube 4 µl of the melted agarose containing the PCR product was combined with 1 µl TOPO TA cloning vector and was incubated at 37° C. for 10 minutes. Transformation was accomplished by mixing 2–4 µl of this reaction mix with one vial (50 µl) of *E. coli* competent cells provided with the kit. These were incubated on ice for 30 min. The cells were heat-shocked at 42° C. for 30 seconds without shaking. The vial was immediately transferred to ice and 250 µl of room temperature SOC medium was added. This tube was then shaken horizontally at 37° C. for 30 min. Aliquots were spread on LB plates+100 µg/ml ampicillin upon which 25 µl isopropylthiogalactoside (IPTG, 100 mM)+40 µl Xgal (5-bromo-4-chloro-3-indolyl β-D-galactopyranoside, 40 mg/ml) had been spread at least 30 minutes prior. Transformants containing inserts were determined by blue/white selection, with blue indicating a successful transformation containing an insert.

White colonies that were positive for the presence of an insert were inoculated in LB media containing 100 µg/ml ampicillin and grown overnight. Plasmid DNA was obtained from these cultures using the Qiaprep kit method (Qiagen, Qiaprep Spin Miniprep Kit #27106), and analyzed for the presence of the insert by restriction with EcoRI. In the PCR 2.1 vector, the insert is flanked on either side by EcoRI sites, so that cutting with EcoRI will release whatever has been inserted into the plasmid. Several clones showed the correct insert size of about 1200 bp. Two of the clones were sequenced and the DNA sequence was compared to the published sequence for FAOT (12). Since the degree of homology for both clones was very high (79% matching bases 608–1199 of the FAOT ORF), one of them was selected to prepare the probe DNA.

Preparation of Probe DNA

Several micrograms of plasmid DNA were obtained from one positive clone and the DNA was digested with EcoRI to release the insert. Electrophoresis of the digest on a 1.2% low-melting agarose gel allowed separation of the FAO fragment from the PCR 2.1 vector. The appropriately sized DNA was extracted from the gel (Qiaprep, QIAquick Gel Extraction Kit, #28706) and was quantified with a fluorometer. The FAO DNA fragment was then labeled using the ECL (Amersham, ECL kit, #RPN 3001) method.

EXAMPLE 3

Cloning of FAO Genes from *Candida tropicalis* ATCC 20336

Plates of the λ phage library of *C. tropicalis* were made and lifts of these plates onto nitrocellulose membrane filters were performed, following the procedure described in Materials and Methods (Example 1). Putative positive clones were identified as outlined in Materials and Methods (Example 1). The XLOLR cells containing these library fragments were grown up and plasmid DNA was obtained using the Qiaprep kit. Restriction digest and PCR analyses confirmed the presence of an FAO gene in these *C. tropicalis* library clones. It was known from the sequence information of the probe DNA that at least some of the clones should cut with PvuII and KpnI. Therefore, the library clones were digested with EcoRI, PvuII, and KpnI in single digests, and with PvuII and KpnI in a double digest. This allowed the direction of the FAO gene to be determined and its placement within the insert of the PBK-CMV vector to be estimated. The initial primers used in preparing the probe DNA, FAO-F2 and FAO-R1, were used to PCR-screen the library clones using purified plasmid DNA of these clones as the template. *C. tropicalis* ATCC 20336 genomic DNA was used as the template for the PCR reaction in the control. Eight FAO library clones, designated A1, A4, A5, A6, A8, A9, B5, and B6, were identified as putative positive clones and were sent to the Sequetech Corporation for sequencing.

When the DNA sequences of the clones were compared to the published FAOT sequence, the clones fell into two groups. Group 1 was composed of clones A4, A8, B5, and B6. Group 2 was composed of A1, A5, A6, and A9.

4297 bp of the gene from clone A8, which was designated FAO1, was double-strand sequenced (SEQ ID No:1). In addition to the open reading frame (ORF), which was 2112 bp in length, there was 1940 bp upstream and 242 bp downstream DNA sequenced. 4158 bp of the gene from clone A9, which was designated FAO2a, was double-strand sequenced (SEQ ID No:3). In addition to the open reading frame (ORF), which was 2112 bp in length, there was 1520 bp upstream and 523 bp downstream DNA sequenced. There is a CTG codon at bp 2049–2051 in the FAO2 sequence presented in SEQ ID NO:3 (bp 529–531 of the ORF). This CTG is designated as leucine in the universal code, but sequence analysis (14) has confirmed that CTG actually codes for serine in *Candida tropicalis* ATCC 20336.

Additional sequencing of clone A6 demonstrated close homology to clone A9. There were a few base pair differences, however, so double strand sequencing of the gene was performed. The results (SEQ ID No:5, Table 2 and Table 3) showed that clone A6 was most likely an allele of clone A9. It was designated FAO2b.

The ORF regions of FAO1, FAO2a and FAO2b were compared to analogous regions of the published (12) FAOT gene from *Candida tropicalis* (NCYC 470), the FAO1 and FAO2 genes from *Candida cloacae* and the FAO gene from *Candida albicans* (Table 2).

TABLE 2

DNA Sequence Comparison Between the Subject *C. tropicalis* FAO1 or FAO2 Genes and Published Sequence Data for *C. tropicalis* NCYC 470, *C. cloacae*, and *C. albicans* FAO Genes

| DNA Sequence #1 | DNA Sequence #2 | % Identity |
|---|---|---|
| *C. tropicalis* FAO1 | *C. tropicalis* FAO2a | 82 |
| *C. tropicalis* FAO1 | *C. tropicalis* FAOT | 77 |
| *C. tropicalis* FAO1 | *C. albicans* FAO | 71 |
| *C. tropicalis* FAO1 | *C. cloacae* FAO1 | 62 |
| *C. tropicalis* FAO2a | *C. tropicalis* FAOT | 78 |
| *C. tropicalis* FAO2a | *C. albicans* FAO | 73 |
| *C. tropicalis* FAO2a | *C. cloacae* FAO1 | 63 |
| *C. tropicalis* FAO2b | *C. tropicalis* FAO1 | 81 |
| *C. tropicalis* FAO2b | *C. tropicalis* FAO2a | 95 |
| *C. tropicalis* FAO2b | *C. tropicalis* FAOT | 77 |
| *C. tropicalis* FAO2b | *C. albicans* FAO | 73 |
| *C. tropicalis* FAO2b | *C. cloacae* FAO1 | 62 |
| *C. tropicalis* FAOT | *C. cloacae* FAO1 | 62 |
| *C. tropicalis* FAOT | *C. albicans* FAO | 73 |
| *C. cloacae* FAO1 | *C. albicans* FAO | 59 |
| *C. cloacae* FAO1 | *C. cloacae* FAO2 | 79 |

The amino acid sequences, which were derived using the universal code, were also compared (Table 3).

TABLE 3

Derived Amino Acid Sequence Comparison Between the Subject *C. tropicalis* FAO1 or FAO2 Genes and Published Sequence Data for *C. tropicalis* NCYC 470, *C. cloacae*, and *C. albicans* FAO Genes

| Protein #1 | Protein #2 | % Identity | % Similarity |
|---|---|---|---|
| Cognis' FAO1 | Cognis' FAO2a | 81 | 92 |
| Cognis' FAO1 | *C. tropicalis* FAO | 82 | 90 |
| Cognis' FAO1 | *C. albicans* FAO | 74 | 88 |
| Cognis' FAO1 | *C. cloacae* FAO1 | 60 | 76 |
| Cognis' FAO2a | *C. tropicalis* FAO | 85 | 93 |
| Cognis' FAO2a | *C. albicans* FAO | 78 | 88 |
| Cognis' FAO2a | *C. cloacae* FAO1 | 59 | 76 |
| Cognis' FAO2b | Cognis' FAO1 | 80 | 91 |
| Cognis' FAO2b | Cognis' FAO2a | 97 | 98 |
| Cognis' FAO2b | *C. tropicalis* FAOT | 85 | 93 |
| Cognis' FAO2b | *C. albicans* FAO | 76 | 88 |
| Cognis' FAO2b | *C. cloacae* FAO1 | 59 | 75 |
| *C. tropicalis* FAO | *C. cloacae* FAO1 | 60 | 77 |
| *C. tropicalis* FAO | *C. albicans* FAO | 76 | 87 |
| *C. cloacae* FAO1 | *C. albicans* FAO | 55 | 72 |
| *C. cloacae* FAO1 | *C. cloacae* FAO2 | 76 | 88 |

The FAO2a and FAO2b genes are 95% identical by DNA sequence and have 97% identity and 98% similarity by amino acid sequence.

The FAO1 and FAO2a genes of the present invention are 82% identical by DNA sequence (81% for FAO2b) and have 81% identity and 92% similarity by amino acid sequence (80% identity and 91% similarity for FAO2b). In comparison, the *C. cloacae* FAO1 and FAO2 genes are 79% identical by DNA sequence and have 76% identity and 88% similarity by amino acid sequence. These results indicate that like *C. cloacae, C. tropicalis* strain 20336 has two different fatty alcohol oxidase genes.

Interestingly, Vanhanen et al. (4) identified only one FAO gene in their *C. tropicalis* NCYC 470 strain. DNA sequence of FAOT was 77% identical to the FAO1 and FAO2b genes of the present invention and 78% identical to the FAO2a gene of the present invention. The amino acid sequence comparison showed that FAOT had 82% identity and 92% similarity to the FAO1 gene of the present invention and had 85% identity and 93% similarity to the FAO2a and FAO2b genes of the present invention. Although the FAOT gene was most similar to the FAO2a gene of the present invention, the dissimilarity was still equivalent to about 49 amino acids out of 704. These data demonstrate that the published FAOT gene is slightly more similar to either of the FAO genes of the present invention than the FAO genes of the present invention are to each other. This data further indicates the likelihood that FAO1, FAO2 and FAOT are different genes, rather than alleles of one another.

Although a 1200 bp PCR fragment from all the clones was obtained using primers 30F2 and 30R1, the band was generally quite weak, even after optimization of the PCR conditions was performed. When the primers, which were designed from the published FAOT sequence, were aligned with the FAO1. FAO2a and FAO2b genes of the present invention (Table 4), significant lack of homology, particularly with FAO-F1 and FAO-F2, was observed. This also indicates that FAO1. FAO2 and FAOT are different genes. Even though published sequence information from *Candida tropicalis* was used to derive the PCR primers, the degree of sequence variation made finding a functioning PCR primer pair uncertain.

TABLE 4

Comparison of Primer Sequence to Corresponding Sequence in *Candida tropicalis* FAO1 and FAO2.

| Gene | Sequence Comparison | Primer |
|---|---|---|
| *C.t.* FAOT | 352 5' **TCG TGG CGT GAC TCT CCT** 3' 369 (SEQ ID NO:35) | FAO-F1 |
| *C.t.* FAO1 | 352 5' **TCG TGG CGT GAC TCC CCT** 3' 369 (SEQ ID NO:44) | |
| *C.t.* FAO2a | 352 5' **TCT TGG CGT GAT TCC CCG** 3' 369 (SEQ ID NO:45) | |
| *C.t.* FAO2b | 352 5' **GCC TGG CGT GAT TCC CCG** 3' 369 (SEQ ID NO:46) | |
| *C.t.* FAOT | 608 5' **CTG GTG CTG GTG TAG T** 3' 623 (SEQ ID NO:38) | FAO-F2 |
| *C.t.* FAO1 | 608 5' **CCG GTG CTG GTG TCG T** 3' 623 (SEQ ID NO:47) | |
| *C.t.* FAO2a | 608 5' **CCG GTG CTG GTG TCA T** 3' 623 (SEQ ID NO:48) | |
| *C.t.* FAO2b | 608 5' **CCG GTG CTG GTG TCA T** 3' 623 (SEQ ID NO:49) | |
| *C.t.* FAOT | 1780 5' **TTG GTA CCC ATG CTT GTG G** 3' 1762 (SEQ ID NO:41) | FAO-R1 |
| *C.t.* FAO1 | 1780 5' **TTG GCA CCC ATG GTT GGG G** 3' 1762 (SEQ ID NO:50) | |
| *C.t.* FAO2a | 1780 5' **TTG GCA CCC ATG GCT GTG G** 3' 1762 (SEQ ID NO:51) | |
| *C.t.* FAO2b | 1780 5' **TTG GCA CCC ATG CCT GTG G** 3' 1762 (SEQ ID NO:52) | |

EXAMPLE 4

Sub-Cloning and Expression of FAO1 and FAO2 in *E. coli*

PCR of FAO1 and FAO2 genes

Since the sequence homology data strongly indicated that FAO1 and FAO2 were different genes, the uniqueness of the two genes was investigated by cloning and expressing FAO1 and FAO2a individually in *E. coli* to determine the substrate specificity of the two gene products.

The open reading frames of these two genes were amplified by PCR and cloned (Argonne National Labs, Argonne, Ill.) into the self-replicating vector pJF118EH (13). This vector, containing either the FAO1 or FAO2 gene, was transformed into *E. coli*. Placing the genes for the FAO1 and FAO2 enzymes into *E. coli* allowed overexpression of the proteins thereby allowing large quantities of enzymes to be generated in a clean background so that their properties could be more clearly defined.

Initially, only the properties of the enzyme derived from the native sequence of FAO2a were determined. It is known, however that FAO2a has a CTG codon, which is translated as a serine in *C. tropicalis* but as a leucine in *E. coli*. Because of that, an FAO2a construct (designated FAO2a') was generated having a TCG codon, which codes for serine in both *C. tropicalis* and *E. coli*, in place of the CTG codon. The properties of both FAO2a and FAO2a' were determined as described in the following examples.

The primers used to amplify the coding regions of the FAO1 and FAO2 genes by PCR are shown below. The restriction sites (underlined) EcoRI and BamHI were added at the 5' and 3' ends, respectively. The ATG initiation codon in the forward primer and the dual termination codons in the reverse primers are shown in itialics.

*FAO1U*
5'-CCGAATTCGAC*ATG*GCTCCATTTTTG-3' (SEQ ID NO:53)

*FAO1L*
5'-CCGGATCC*ATTACTA*CAACTTGGCCTTGGT-3' (SEQ ID NO:54)

*FAO2U*
5'-CCAGTGAATTCAG*ATG*AATACCTTCT-3' (SEQ ID NO:55)

*FAO2L*
5'-CCGGATCCCCGTC*TCACTA*CAACTTG-3' (SEQ ID NO:56)

PCR used Platinum Pfx DNA Polymerase from Life Technologies, Inc. (Rockville, Md. 20849-6482). The reaction conditions for each 50 μl reaction were:

1× buffer (supplied by manufacturer)
1.0, 1.5 or 2.0 mM $MgSO_4$
1 μM each primer
0.2 mM each of the 4 dNTPs
200–400 ng FAO1 or FAO2 plasmid
1 unit Platinmum Pfx Polymerase Reactions were incubated in a Robocycler Gradient 96 thermocycler (Stratagene) for one cycle at 94° C. for 2 minutes, followed by 30 cycles at 94° C. (30 seconds); 55° C., 58° C. or 61° C. (45 seconds); 72° C. (2 minutes). The reactions were completed by incubation at 72° C. (10 minutes) for 1 cycle.

FAO1 gave the expected product (2.1 kb) under all of the conditions tested. The optimum conditions for FAO2 were at 1.0–1.5 mM $MgSO_4$ and 55° C.–58° C.

Agarose Gel Purification of PCR Products

Three of the PCR reactions for each gene were pooled and purified with the QIAquick-spin PCR Purification Kit (Qiagen) following the manufacturer's instructions. The DNA was then fractionated on a 1.0% agarose gel. The 2.1 kb bands were removed and the DNA extracted with the QIAEX II Gel Extraction Kit (Qiagen) following the manufacturer's instructions.

Ligation into pJF118EH

The expression vector pJF118EH (13) was digested with EcoRI and BamHI, and fractionated on a 1.0% agarose gel. The band was excised and purified with the QIAEX II Gel Extraction Kit (Qiagen). The FAO1 and FAO2 PCR products were digested with EcoRI and BamHI, and gel purified in the same manner. The digested bands were visualized on an agarose gel but the exact concentrations were not determined.

Ligation reactions (20 μl) containing 1 μl of FAO1 or FAO 2 and 4 μl pJF118EH in 1× ligation buffer (Promega) with 1 μl (3 units) T4 DNA ligase (Promega) were incubated for 2 hours at 25° C. 100 μl of Library Efficiency DH5 *E. coli* (Life Technologies, Inc.) were transformed with 1.5 μl of each ligation reaction.

Six colonies from each transformation were selected, miniprep DNA was prepared and insert size determined by digestion with EcoRI and BamHI. 5 of the 6 FAO1 clones contained the 2.1 kb insert. All 6 of the FAO2 clones contained the 2.1 kb insert.

Figure 2:
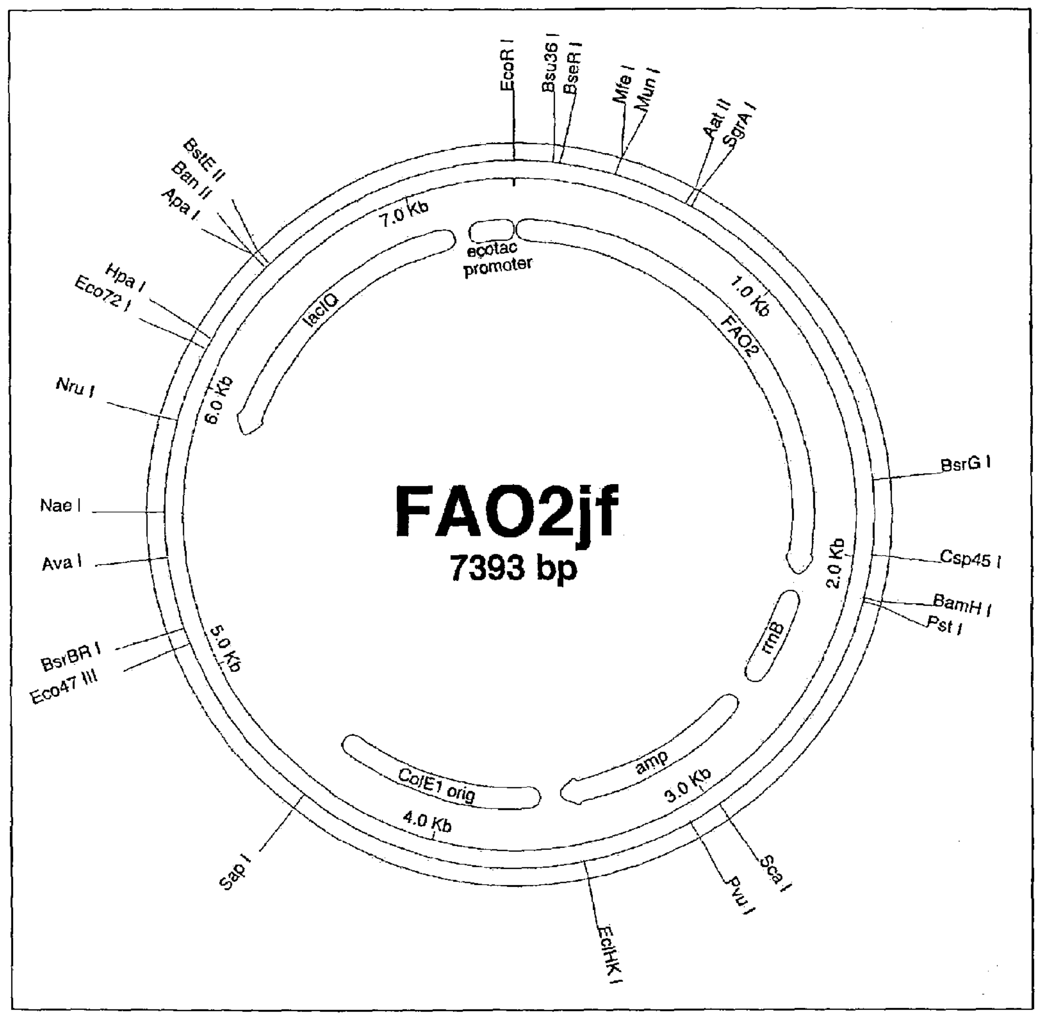
FIG. 2 is a restriction map of FAO2jf which is the coding region of the FAO2 gene ligated into the expression vector pJF118EH.

One clone of each was selected and glycerol stocks were stored at −80° C. Samples of each clone were also used for expression and enzyme activity analysis. The FAO1 clone, designated FAO1-EC, contained plasmid FAO1jf (see FIG. 1), and the FAO2 clone, designated FAO2-EC, contained plasmid FAO2jf (see FIG. 2). Both FAO genes in these plasmids were sequence confirmed by Sequetech Corporation, Mountain View, Calif.

Induction of FAO1 and FAO2

Overnight cultures of FAO1-EC and FAO2-EC were grown at 30° C. in 5 ml of Terrific Broth (TB) (Sigma Chemical Co, St. Louis, Mo.) plus 100 μg/ml ampicillin at 250 rpm. 50 ml of TB plus 100 μg/ml ampicillin was placed in each of two 500 ml baffled flasks. TB plus 100 μg/ml ampicillin was used for both the starter cultures and the cultures that were induced to produce the enzyme. The flasks were inoculated with the overnight cultures to an absorbance at 600 nm of approximately 0.2. The cultures were grown at 30° C., with shaking at 250 rpm. When each culture had reached an absorbance at 600 nm of 5 to 6, it was induced with IPTG to a final concentration in each culture of 1 mM. The cultures were then allowed to incubate another three hours post-induction. The cells were harvested by centrifugation (Sorvall RC5C) at approximately 6,000×g (GS3 rotor at 6,000 rpm) for 10 minutes. The supernatant spent broth (SB) was removed and saved, and the cell pellets were frozen at −20° C. for later use.

Preparation of *E. coli* Cell Extracts

Microsomes were prepared for alcohol oxidase assays by resuspending the induced cell pellets in 50 ml $PO_4$/glycerol buffer. 500 μl of a 100 mM PMSF solution was added for a final concentration of 1 mM of PMSF in the suspension. The cells were broken by passage twice through a chilled French pressure cell, and were examined by phase contrast microscope to assure that 95% or greater of the cells had been broken. The broken cell suspension (BCS) was centrifuged at approximately 37,000×g for 30 minutes to pellet the cellular debris. The supernatant (cell free extract, CFE) was removed and saved for assays. The pellet of cellular debris (CD) was resuspended in 50 ml of phosphate-glycerol buffer so that it was equal to the original concentration of the cells in the culture.

Preparation of *E. coli* Microsomal Suspensions

The cell-free extracts were warmed to room temperature and thoroughly mixed before a 3 ml sample of each was removed for the microsomal preparation. These samples were centrifuged in an ultracentrifuge at 100,000×g for one hour at 4° C. to pellet the microsomes. The supernatant was then removed and saved, and each microsomal pellet was resuspended in 0.5 ml $PO_4$/glycerol buffer for a 6× concentration of the FAO enzyme.

EXAMPLE 5

Construction of a CTG-Codon-Altered FAO2a Gene

A codon alteration of FAO2a was performed by overlap-extension PCR. The following primer sets were used to generate the initial constructs:

```
A9.1N        5' ATC AAC GCC ACC CCA ACC 3'                          (SEQ ID NO:57)
FAO2-CTG-R   5' GGT TTC TCC ATA AAC GAG TAC CTG AAAGGG TCA ACC 3'   (SEQ ID NO:58)
```

These primers were designed to cover the region 208 bp 3' to 545 bp 3' of the start of the ORF yielding a fragment of 338 bp in length. The CTG codon alteration to CGA (TCG in reversed complement) is indicated in bold. A former KpnI restriction site (GGTACC), underlined above, has been eliminated by this codon alteration.

PCR used Platinum Pfx DNA Polymerase from Life Technologies, Inc. The reaction conditions for each 50 μl reaction were:

1× buffer (supplied by manufacturer)
1.0 mM $MgSO_4$
1 μM each primer
0.3 mM each of the 4 dNTPs
200–400 ng FAO2a plasmid
1 unit Platinmum Pfx Polymerase

```
A9.1E        5' ATC TGT CTA GCA AAG GTC 3'                          (SEQ ID NO:59)
FAO2-CTG-F   5' GGT TGA CCC TTT CAG GTA CTC GTT TAT GGA GAA ACC 3'  (SEQ ID NO:60)
```

These primers were designed to cover the region 510 bp 3' to 2069 bp 3' of the start of the ORF yielding a fragment of 1560 bp in length. The FAO2-CTG-F and FAO2-CTG-R are overlapping primers.

This PCR also used Platinum Pfx DNA Polymerase from Life Technologies, Inc. The reaction conditions for each 50 μl reaction were:

1× buffer (supplied by manufacturer)
5.0 mM $MgSO_4$
1 μM each primer
0.3 mM each of the 4 dNTPs
200–400 ng FAO2a plasmid
1 unit Platinmum Pfx Polymerase Reactions were incubated in a PTC200 thermal cycler (MJ Research) for one cycle at 94° C. for 2 minutes, followed by 30 cycles at 94° C. (15 seconds); 55° C. (30 seconds); 68° C. (4 minutes). The reactions were completed by incubation at 72° C. (7 minutes) for 1 cycle.

The appropriate-sized PCR fragments were separated on 1% low-melting agarose gel, and were then excised into separate microfuge tubes. A third PCR was performed using primers A9.1N and A9.1E. This PCR also used Platinum Pfx DNA Polymerase from Life Technologies, Inc. The reaction conditions for each 50 μl reaction were:

- 1× buffer (supplied by manufacturer)
- 2.0 mM $MgSO_4$
- 1 μM each primer
- 0.3 mM each of the 4 dNTPs
- 1 μl each PCR fragment (338 bp and 1560 bp, low melt agarose melted at 65° C.)
- 1 unit Platinum Pfx Polymerase The reaction was incubated in a PTC200 thermal cycler (MJ Research) for one cycle at 94° C. for 2 minutes, followed by 30 cycles at 94° C. (15 seconds); 60° C. (30 seconds); 68° C. (2 minutes). The reactions were completed by incubation at 72° C. (7 minutes) for 1 cycle. This resulted in a PCR fragment that was 1862 bp in length and covered from 208 bp to 2069 bp from the start of the ORF. This fragment was TOPO-TA cloned and the resulting plasmid was prepared as described in Materials and Methods (Example 1).

In order to replace the CTG codon in plasmid FAO2jf with the modified sequence, the plasmid, FAO2jf, was cut with KpnI and MfeI to remove a fragment 470 bp in length, leaving the major portion of the plasmid, 6924 bp intact. The 1862 bp fragment was also cut with KpnI and MfeI to remove a fragment 470 bp in length. The appropriate fragments, the 6924 bp fragment from plasmid FAO2jf and the 470 bp fragment cut from the 1862 bp fragment containing the modified CTG codon, were purified on 1% agarose gel, and then were extracted from the gel using Qiagen's Qiaquick kit.

After obtaining the appropriate DNA fragments, a ligation was set up using the Quick Ligation product and protocol from New England Biolabs. This ligation was transformed back into DH5α cells. Plasmid preparations from putative clones were screened by cutting with KpnI and Mfe I. One of the positive clones was selected for further study and was designated FAO2a'EC. Since all of the CTG-modified FAO2a gene (designated FAO2a') except for the 469 bp fragment containing the codon modification had been previously sequence verified, only this 469 bp portion of the gene was sequence-verified. The gene did have the appropriate codon changed from a CTG to a TCG (bp 2049–2051 in SEQ ID NO:9. It also had a second mutation, presumably generated by PCR. The mutation was at bp 2117 and resulted in a codon change from ATT to ATC, both of which code for isoleucine.

Amplification Cassette Preparation for FAO1 and FAO2

The initial step in creation of the amplification cassette of FAO1 and FAO2 was to use primers with PacI restriction sites on the ends to amplify the ORF and upstream regions of each gene. For FAO1 the primers used were: (PacI restriction site underlined)

```
FAO1-F3-PacI 5' CCT TAA TTA ATG CAT ACT CGG AGC ATA TCG C 3'  (SEQ ID NO:61)
FAO1-R3-PacI 5' CCT TAA TTA ATG GGC GGA ATC AAG TGC C 3'      (SEQ ID NO:62)
```

The region covered is 1939 bp 5' and 245 bp 3' of the ORF

For FAO2 the Primers were:

```
FAO2-F1-Pac I5' CCT TAA TTA ATC TCA CCA AGT ACG AGA ACG 3'  (SEQ ID NO:63)
FAO2-R1-Pac I5' CCT TAA TTA AGA CGC AAG CAC AGG TGC C 3'    (SEQ ID NO:64)
```

The region covered is 1520 bp 5' and 526 bp 3' of the ORF

The Accutaq LA Core Kit (Sigma, #ACCUCORE) was used to create the PCR fragments. This kit contains both a Taq DNA polymerase with a small amount of a proofreading enzyme. The reaction mixture was prepared following the recommendations in the kit. The PCR conditions followed were: 98° C. for 30 see followed by 35 cycles of: 94° C. for 5 sec, 65° C. for 20 see and 68° C. for 5 min. Following this there was a final extension of 72° C. for 5 min. These PCR fragments were TA-TOPO cloned into PCR 2.1 vector, which was transformed into *E. coli* strain Top10F' cells, creating the strains FAO1:PacI and FAO2:PacI.

In order to replace most of the ORF sequence obtained by PCR with genomic DNA, FAO1:PacI was cut with AatII and NheI to release a fragment approximately 1.9 kb in length. Its complementary library clone, A8.1, was also cut with AatII and NheI. FAO2:PacI and its complementary library clone, A9.1, were cut with NheI and BstBI to release a 3.2 kb fragment. The appropriate fragments were purified on 1% low-melting agarose gel, and then were extracted from the gel using Qiagen's Qiaquick kit.

After obtaining the appropriate DNA fragments, a ligation was set up for both FAO1 and FAO2 in which the ORF from the library clones was ligated into the PCR 2.1 vector with the upstream and downstream regions of the gene. These ligations were transformed back into Top10F' cells. Plasmid preparations from putative clones were screened by cutting with AatII and NheI for the FAO1 clones, or cutting with NheI and BstBI for the FAO2 clones, and cutting with PacI for all clones.

Because the beginning and end of each ORF was obtained from the original PCR amplification of each gene, these areas needed to be sequenced to make sure that no mutations had been introduced into the ORF. Three FAO1:PacI ORF replacement clones were sent to Sequetech Corp. (Mountain View Calif.) for sequencing. Five FAO2:PacI ORF replacement clones were also sent to Sequetech Corp. for sequencing. The FAO1: PacI ORF replacement clones 1 and 2, and FAO2:PacI ORF replacement clones 1–5 were all mutation free, and could be used for making amplification cassettes.

EXAMPLE 6

Preparation of a Promoter Fusion Construct

Fusions between the promoter of the cytochrome p450 monooxygenase gene CYP52A2, and the ORF of either FAO1 or FAO2 were prepared by overlap extension PCR. PCR reactions for both the CYP52A2 promoter and FAO ORF were set up using the Accutaq PCR kit. The primers used to obtain the CYP52A2 promoter for the fusion with FAO1 were (PacI restriction site):

```
00218-179A  5' CCT TAA TTA AAG TCT CCA AGT TGA CCG AC 3' (SEQ ID NO:65)
FAO1-A2-R   5' AAA TGG AGC CAT GGT CGT GAT GTG TG 3'     (SEQ ID NO:66)
```

FAO-A2-R was designed to sit at the 3' end of the CYP52A2 promoter, but the last half of the 5' to 3' end of the primer was derived from the complementary sequence of the beginning of the FAO1 ORF. Conversely, the primers used to amplify the FAO1 ORF were:

```
FAO1-A2-F     5' CAC ATC ACG ACC ATG GCT CCA TTT TTG CC 3' (SEQ ID NO:67)
FAO1-R3-Pac I 5' CCT TAA TTA ATG GGC GGA ATC AAG TGC C 3'  (SEQ ID NO:68)
```

FAO1-A2-F was designed to sit at the 5' end of the FAO1 ORF, with the first half of the 5' to 3' end of the primer derived from the complementary sequence of the end of the CYP52A2 promoter. In this way, the CYP52A2 promoter and FAO ORF regions produced had complementary sequences to one another.

The primers used to obtain the CYP52A2 promoter were:

```
00218-179A  5' CCT TAA TTA AAG TCT CCA AGT TGA CCG AC 3' (SEQ ID NO:69)
FAO2-A2-R   5' GAA GGT ATT CAT GGT CGT GAT GTG TG 3'     (SEQ ID NO:70)
```

The primers used for the FAO2 ORF regions were:

```
FAO2-A2-F     5' CAC ATC ACG ACC ATG AAT ACC TTC TTG CC 3' (SEQ ID NO:71)
FAO2-R1-Pac I 5' CCT TAA TTA AGA CGC AAG CAC AGG TGC C 3'  (SEQ ID NO:72)
```

Once the appropriate PCR bands had been obtained, each PCR fragment was purified on a 1% low-melt agarose gel, which was then cut from the gel, and the PCR product extracted. The CYP52A2 promoter band was approximately 1.1 kb for both fusion reactions. The ORF band for FAO1 was approximately 2.4 kb and the ORF band for FAO2 was approximately 2.7 kb. The fusion PCR was set up using a small portion of the CYP52A2 promoter and FAO ORF gel-purified bands as template DNA. The Accutaq kit was used, and the primers were the forward primer for the CYP52A2 promoter and the reverse primer for each FAO ORF. During the PCR reaction, the CYP52A2 promoter and FAO ORF annealed together at their complementary ends, and the PCR reaction continued over the junction to form the fusion construct. The $_{pCYP52A2}$FAO1 fusion band was 3.5 kb and the $_{pCYP52A2}$FAO2$^a$ fusion band was 3.8 kb.

These fusion bands were then TA-TOPO cloned and transformed into Top10F' *E. coli* cells. Once again, the majority of the ORF frame of each fusion clone was replaced with corresponding genomic DNA because of the possibility of the PCR reaction introducing mutations into the ORF. The $_{pCYP52A2}$FAO1 clones were cut with the restriction enzymes AatII and NheI to remove most of the FAO1 ORF. The $_{pCYP52A2}$FAO2$^a$ clones were cut with the restriction enzymes AatII and BstBI. A corresponding genomic fragment for each FAO ORF was obtained in a similar manner. After digesting, the appropriate fragments of each gene were purified and ligated together. The resulting plasmid contained the $_{pCYP52A2}$FAO fragment with the replaced FAO genomic DNA in the PCR 2.1 vector. This was transformed into Top10F' cells and three of the $_{pCYP52A2}$FAO1 and five of the $_{pCYP52A2}$FAO2$^a$ clones were sent to Sequetech Corporation for sequencing.

After sequencing, all three of the $_{pCYP52A2}$FAO1 ORF replacement clones were shown to have no mutations and were suitable for making amplification cassettes. Sequencing showed that all five of the $_{pCYP52A2}$FAO2$^a$ ORF replacement clones had apparent mutations introduced by the PCR in various places in the ORF.

Creation of amplification cassettes for $_{pCYP52A2}$FAO1 fusion clone was accomplished by removing the fragment from the PCR 2.1 vector and cloning it into the pURA3in vector. This vector consisted of pNEB193 with inverted fragments of the URA3 gene from *C. tropicalis* flanking either region of the insertion site. The insertion site is a single PacI restriction enzyme site, into which the $_{pCYP52A2}$FAO1 fusion clone can be inserted after restriction digest with PacI and gel purification. The URA3 gene fragments are flanked by AscI and PmeI restriction digest sites so the entire fragment of the FAO clone insertion flanked by the URA3 inverted gene sequences can be removed and used to transform a *Candida tropicalis* ura⁻ base strain. This was successfully performed using $_{pCYP52A2}$FAO1.

EXAMPLE 7

Results

Alcohol Oxidase Activity in Fermentation Samples

Figure 3:
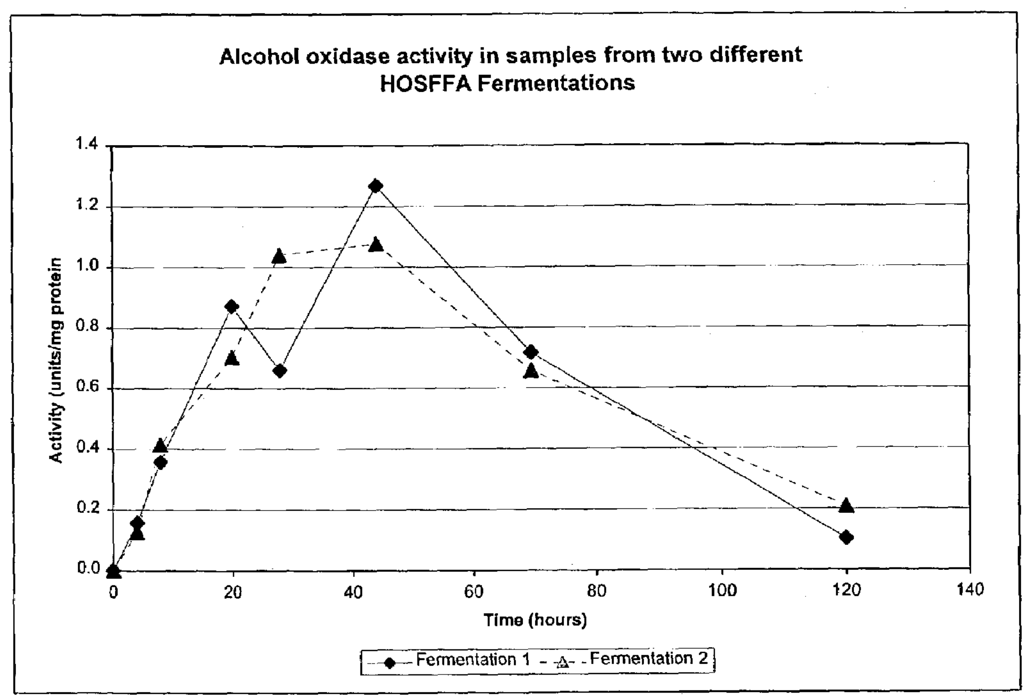
FIG. 3 graphically depicts typical alcohol oxidase activity in lab-scale fermentations with oleic acid as substrate.

During the course of a diacid fermentation with strain HDC23-3 using HOSFFA as substrate, FAO activity generally did not appear until approximately 2–4 hours post-induction with HOSFFA (see FIG. 3). Activity rose rapidly to peak at approximately 30–40 hours post-induction, and then dropped approximately 5 to 10 fold by 100–120 hours post-induction. Although this trend remained consistent among most of the fermentation runs, the time and height of the peak of activity did vary somewhat.

One of the difficulties encountered in measuring FAO activity in the extracts was the presence of catalase in the cells. Catalase converts hydrogen peroxide in the cell into water and molecular oxygen. Catalase in the extracts could compete with the horseradish peroxidase for the hydrogen peroxide produced by the oxidation of the alcohol to the aldehyde by the FAO, which could result in activity measurements that were lower than the actual activity. No FAO activity was found in the microsomal supernatant, but there was activity in the resuspended microsomal pellet, and this activity was approximately the same as that in the original extract. Catalase activity was present in the microsomal pellet, but at approximately 1/100 the level found in the original extract. This data indicates that, under the assay conditions used, the catalase was not significantly competing with the horseradish peroxidase for hydrogen peroxide in the reaction mixture.

EXAMPLE 8

Fractionation of Alcohol Oxidase Activity

*E. coli* cells containing the plasmids, FAO1jf or FAO2jf, were induced to express FAO1 or FAO2 as described in Materials and Methods (Example 1). The spent broth, cell free extract, and the resuspension of the cellular debris (see Materials and Methods, Example 1) were all assayed for FAO activity in an effort to determine the location of the FAO activity. If deposited extracellularly, FAO activity would be seen in the spent broth. If deposited internally, FAO activity would be detected in the cell free extract or in the resuspended cellular debris. Soluble enzyme or membrane-bound microsomal enzyme would be found in the cell free extract. To determine the cellular location of the alcohol oxidase, activity assays were performed with the various fractions. No FAO activity was seen in the spent broth, and the activity found in the resuspension of the cellular debris pellet (FAO1=0.002 U/ml; FAO2=0.002 U/ml) was one-fifth to one-tenth the activity determined for cell free extract (FAO1=0.026 U/ml; FAO2=0.044 U/ml).

Microsomal preparations were made from the cell-free extracts of these FAO1 and FAO2 *E. coli* cultures. Activity in each resuspended microsomal pellet and supernatant was tested for FAO activity. No activity was seen in the supernatant from the FAO1 microsomal pellet, and the activity in the supernatant from the FAO2 microsomal pellet (0.010 U/ml) was approximately one-fifth of the activity in the resuspended FAO2 microsomal pellet (0.050 U/ml). The activity in the FAO2 microsomal preparation was almost twice the activity that was seen in the FAO1 microsomal preparation (0.031 U/ml). These data indicate that the majority of the enzymatic activity was contained in the microsomes isolated from the *E. coli* cultures.

Optimization of Induction

In order to determine the optimal temperature for synthesis of the FAO1 and FAO2a enzymes in *E. coli* cultures, seed cultures were grown up overnight at 37° C. and 250 rpm in Terrific broth. 50 ml of Terrific broth was added to each of four 500 ml baffled flasks; one each for FAO1 and FAO2a to be incubated at either 30° C. or 37° C. Each flask was innoculated with the overnight cultures to an absorbance at 600 nm of between 0.7 and 0.8, and was then incubated with shaking at 250 rpm. When each culture had reached an absorbance at 600 nm of approximately 4.5, it was induced with IPTG to a final concentration of 1 mM. The cells were harvested at 3 hours post-induction by centrifugation at 6000×g for 10 minutes. The supernatant was removed and the cells were stored at −20° C. The FAO1 and FAO2a *E. coli* cultures grown at 30° C. and 37° C. were prepared for enzyme assays as described in Materials and Methods. The cell free extract prepared from each of these cultures was assayed for FAO activity. It was found that growth at 30° C. resulted in a greater production of FAO1 (14.7 U/ml) and FAO2 (2.44 U/ml) than growth at 37° C. (8.8 U/ml for FAO1 and 1.33 U/ml for FAO2a).

In a second set of experiments, the optimal concentration of the inducer, IPTG, was determined for *E. coli* containing either FAO1 or FAO2a. The growth experiment was set up in the same way as the previous experiment, with overnight seed cultures of FAO1 and FAO2a grown up at 37° C. in Terrific Broth plus 100 μg/ml ampicillin. 50 ml Terrific broth was added to each of six flasks; three flasks each for FAO1 and FAO2a. One flask from each set was induced with either 0.5 mM IPTG, 1.0 mM IPTG, or 2.0 mM IPTG. The cultures were grown at 30° C. with shaking at 250 rpm. When each culture had reached an absorbance at 600 nm of approximately 5.0, it was induced with the appropriate concentration of IPTG. The cultures were allowed to grow another 2.5 hours post-induction before harvesting the cells by spinning at 6000×g for 10 minutes. The cell pellets were stored at −20° C. Cell free extracts were prepared and after assaying for alcohol oxidase activity, it was found that there was little dependence of the FAO1 activity on IPTG concentration (0.5 mM=13.24 U/ml; 1 mM=13.89 U/ml; 2 mM=14.3 U/ml). A similar response to IPTG concentration was observed for FAO2a (0.5 mM=4.74 U/ml; 1 mM=5.68 U/ml; 2 mM=4.65 U/ml). A standard concentration of 1 mM IPTG was chosen for induction of FAO1, FAO2a and FAO2a'.

TABLE 5

Alcohols Used for Substrate Specificity Testing

| Activity Detected* | Compound Tested | Activity Detected | Compound Tested |
|---|---|---|---|
| | 2-Pentanol | | 1-Phenylpropan-1-ol |
| | 2-Hexanol | | 3-Phenylpropan-1-ol |
| X | 2-Decanol | | 2-Phenylbutan-1-ol |
| X | 2-Undecanol | | Methanol |
| X | 2-Dodecanol | | Ethanol |
| X | 2-Hexadecanol | | Propanol |
| | 3-Octanol | | Butanol |
| X | 10-Undecen-1-ol | X | Hexanol |
| | 1,8-Octanediol | X | Octanol |
| X | 1,2-Octanediol | X | Decanol |

TABLE 5-continued

Alcohols Used for Substrate Specificity Testing

| Activity Detected* | Compound Tested | Activity Detected | Compound Tested |
|---|---|---|---|
| X | 1,10-Decanediol | X | Dodecanol |
| X | 1,2-Dodecanediol | X | Tetradecanol |
| X | 1,16-Hexadecanediol | X | Hexadecanol |
| X | 10-Hydroxydecanoic acid | | 4-cyclohexyl-1-butanol |
| X | 12-Hydroxydodecanoic acid | | 3-cyclohexyl-1-propanol |
| X | 16-Hydroxydodecanoic acid | | 2-cyclohexylethanol |
| | Citronellol | | Cyclohexylmethanol |
| | Geraniol | | |
| | Linalool | | |

*"X"= Activity detected using this substrate with either FAO1 or FAO2

Substrate Specificity of FAO1, FAO2a and FAO2a'

Figure 4:
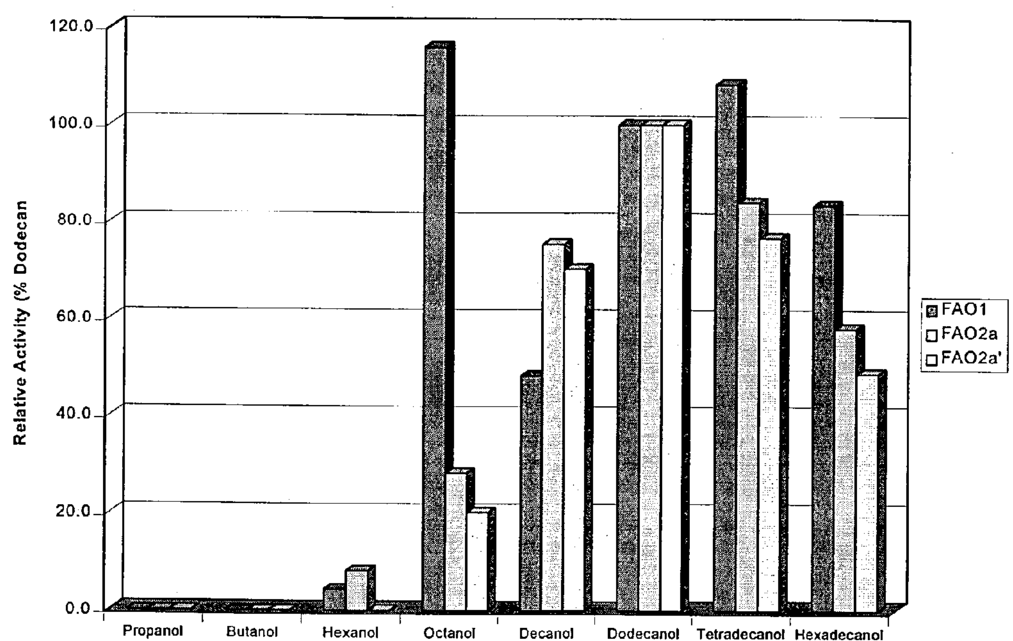
FIG. 4 graphically depicts activity of FAO1, FAO2a, and FAO2a' on 1-alkanols.
Figure 5:
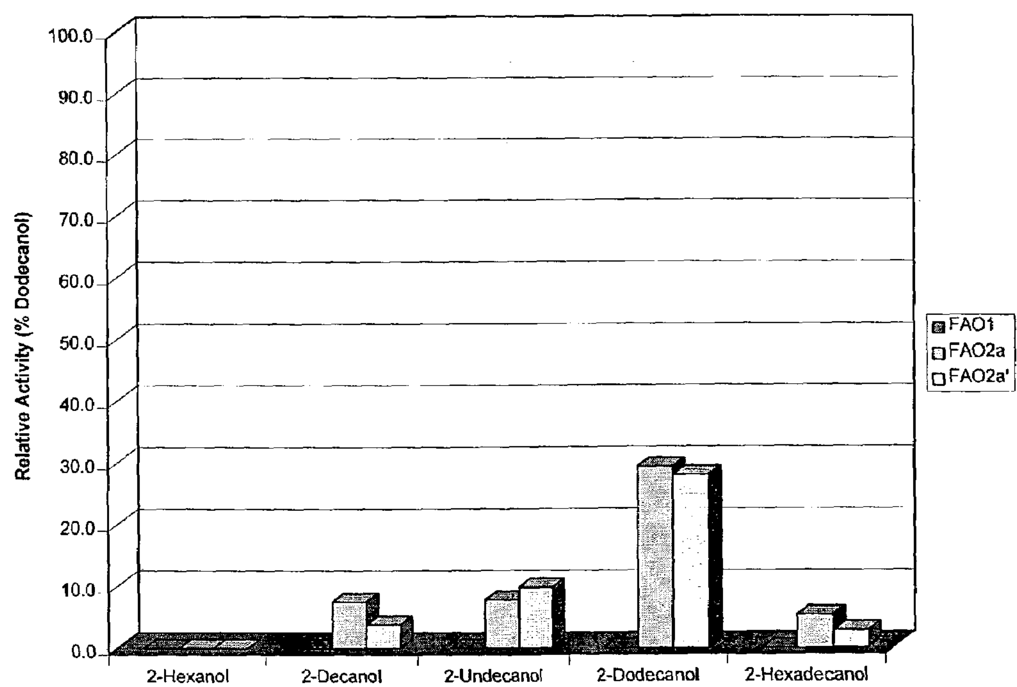
FIG. 5 graphically depicts activity of FAO1, FAO2a and FAO2a' on 2-alkanols.
Figure 6:
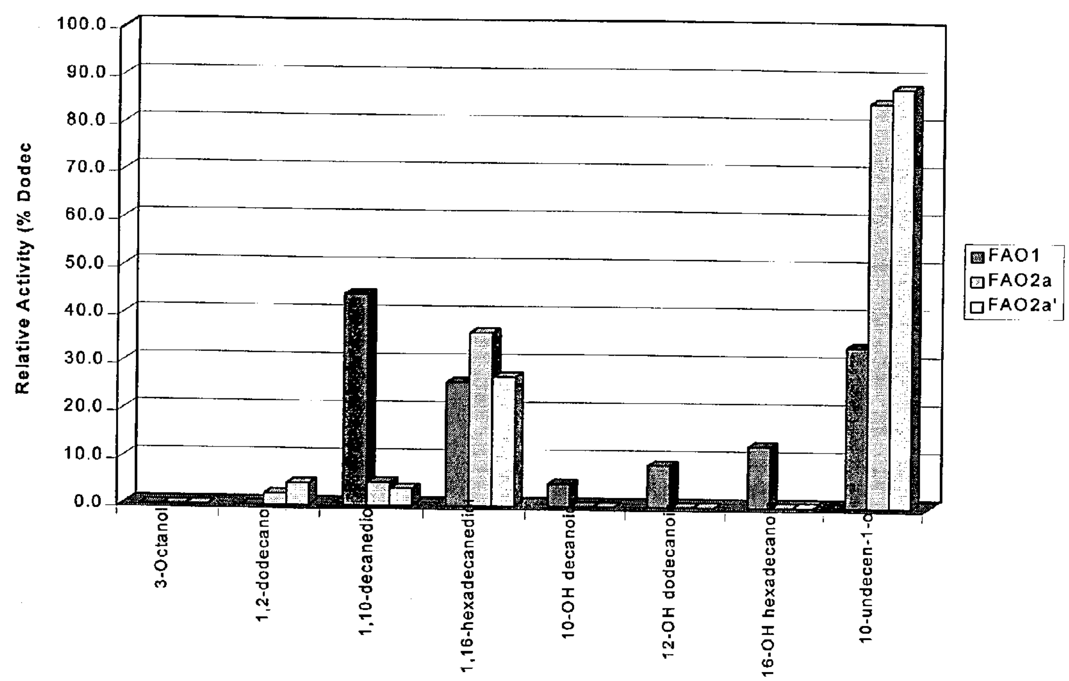
FIG. 6 graphically depicts activity of FAO1, FAO2, and FAO2a' on other alkanols.

FAO1, FAO2a and FAO2a' were tested for their activity with various alcohols. The alcohols shown in Table 5 were prepared in 20 mM stock solutions in acetone. Alcohols showing activity with either FAO1 or FAO2a are indicated. The final concentration of the alcohol used in the substrate specificity experiment was 200 μM. These same alcohols were used to determine the Km and Vmax of FAO1, FAO2a, and FAO2a'. The substrate specificity profiles FAO1, FAO2a, and FAO2a' were reported as percentages of activity for dodecanol, with dodecanol arbitrarily set at 100% activity. The activity of FAO1, FAO2a, and FAO2a' with 1-alkanols is shown in FIG. 4. Interestingly, FAO1 preferred 1-octanol as substrate, with 1-tetradecanol being the preferred longer-chain alcohol. In contrast, FAO2a and FAO2a' preferred 1-dodecanol above all other 1-alkanols. There was a big drop in activity in going from a C8 alcohol to a C6 alcohol with FAO1, FAO2a, and FAO2a'. The activity of the three enzymes on 2-alkanols is shown in FIG. 5. FAO2a and FAO2a' oxidize 2-octanols fairly well; however no activity was detected with FAO1. In contrast, FAO1 oxidizes ω-hydroxy fatty acids well, but no activity for ω-hydroxy fatty acids was measured with FAO2a and FAO2a' (FIG. 6). These results indicate that FAO1 and FAO2a appear to be very different enzymes, with significant differences in substrate specificity. Interestingly FAO2a and FAO2a' oxidize 10-undecen-1-ol much better than FAO1. Within experimental error, the substrate specificity of FAO2a and FAO2a' are essentially the same, indicating that having a serine or a leucine at amino acid position 177 has little if any effect on the substrate specificity of the enzyme. Although the substrate specificity of FAO2b was not performed, due to the close homology with FAO2a, it is likely to be very similar.

Extracts made from fermentor samples induced with HOSFFA show good activity with 16-hydroxyhexadecanoic acid, but no activity with 2-dodecanol (data not shown). Hence, it appears that FAO1 is induced to a much greater extent than FAO2a and, at least in HOSFFA fermentations, FAO1 appears to be the predominant fatty alcohol oxidase.

Km Determinations $K_m$ values indicate the affinity of an enzyme for the substrate being investigated. $K_m$ values for most of the alcohols that demonstrated activity with FAO1, FAO2a, and FAO2a' were determined by measuring enzyme activity while keeping the concentration of enzyme constant and varying the concentration of alcohol added to the reaction mixture.

Most of the $K_m$ values were determined at pH 7.6 using the HEPES/Triton X-100 buffer and stock solutions of alcohols, which were prepared at concentrations of 5 mM and or 1 mM, were dissolved in this same buffer. For FAO2a', the Km values were determined in 0.1 M HEPES, pH 7.6, and the stock solutions of substrate were dissolved in acetone. In this case, all reactions contained the same amount of acetone (20 μl/ml). The results are shown in Table 6.

TABLE 6

Km Values for FAO1, FAO2a, and FAO2a[1].

| | FAO1 | | | | FAO2a | | | | FAO2a[1] | | | |
|---|---|---|---|---|---|---|---|---|---|---|---|---|
| | | Corr. | Range of Values | | | Corr. | Range of Values | | | Corr. | Range of Values | |
| Substrate | Km | Coeff. | Low | High | Km | Coeff. | Low | High | Km | Coeff. | Low | High |
| Octanol | 41.0 μM | 0.9996 | 35.0 | 49.3 | 503 μM | 0.9977 | 329.3 | 1069.2 | 654 μM | 0.9976 | 323.5 | 30607.9 |
| Decanol | 15.1 μM | 0.9912 | 11.8 | 21.3 | 74 μM | 0.9990 | 64.3 | 85.9 | 69.6 μM | 0.9978 | 65.1 | 74.8 |
| Dodecanol | 14.9 μM | 0.9938 | 11.9 | 19.9 | 2.5 μM | 0.9907 | 2.4 | 2.5 | 4.4 μM | 0.9928 | 3.9 | 4.4 |
| Tetradecanol | 28.1 μM | 0.9976 | 20.8 | 43.3 | 4.6 μM | 0.9968 | 4.5 | 4.8 | 2.4 μM | 0.9751 | 2.2 | 2.5 |
| Hexadecanol | 11.9 μM | 0.9998 | 11.1 | 11.8 | 56 μM | 0.9977 | 51.2 | 61.7 | 85 μM | 0.9987 | 78.4 | 93.5 |
| 2-Decanol | NR | | | | 934 μM | 0.9991 | 823.2 | 1078.5 | 1090 μM | 0.9834 | 567.3 | 13696.9 |
| 2-Undecanol | NR | | | | 141 μM | 0.9970 | 125.9 | 159.0 | 162 μM | 0.9913 | 150.9 | 174.5 |
| 2-Dodecanol | NR | | | | 41.3 μM | 0.9990 | 39.60 | 43.06 | 75.3 μM | 0.9980 | 67.9 | 84.5 |
| 2-Hexadecanol | NR | | | | 350 μM | 0.9992 | 332.5 | 370.0 | 720 μM | 0.9982 | 628.1 | 844.2 |
| 1,2-dodecanediol | NR | | | | 998 μM | 0.9935 | 720.2 | 1622.7 | 928 μM | 0.9969 | 742.6 | 1237.3 |
| 1,10-decanediol | 67.0 μM | 0.9997 | 58.9 | 77.6 | 425 μM | 0.9985 | 394.4 | 462.3 | 1607 μM | 0.9975 | 1377.2 | 1927.5 |
| 1,16-hexadecanediol | 10.3 μM | 0.9995 | 9.3 | 11.6 | 37.3 μM | 0.9969 | 33.9 | 41.5 | 16.3 μM | 0.9978 | 15.7 | 16.9 |
| 10-undecene-1-ol | 9.9 μM | 0.9963 | 8.8 | 11.3 | 45 μM | 0.9986 | 40.7 | 50.1 | 36.1 μM | 0.9916 | 32.7 | 40.4 |
| 12-hydroxy-decanoic | 99.0 μM | 0.9930 | 78.2 | 134.4 | NR | | | | NR | | | |
| 16-hydroxy-hexadecanoic | 7.4 μM | 0.9912 | 5.9 | 9.9 | NR | | | | NR | | | |

For most alcohols tested, FAO1 yielded $K_m$ values between 10–20 μM. The lowest Km value was found with 16-hydroxy-hexadecanoic acid. Using either FAO2a and FAO2a' as enzyme, the Km values for the various alcohols were very similar, again demonstrating that having a serine or leucine at amino acid position 177 does not have much effect on the affinity of the enzyme for a particular substrate. For FAO2, the Km values were generally much more variable and yielded values ranging from 2 μM to greater than 1 mM. The substrates with the lowest Km values were 1-dodecanol and 1-tetradecanol. Based on these results, it is logical that FAO1 appears to be the predominant fatty alcohol oxidase produced in HOSFFA fermentations, since ω-hydroxy fatty acids are intermediates in the oxidation of fatty acids to diacids.

EXAMPLE 9

Amplification of FAO1 in *Candida tropicalis*

In fermentations with HOSFFA as substrate, ω-hydroxy fatty acids are produced at levels between 0.1% to 0.5% (w/w) in fermentation broth. This indicates that there is a minor bottleneck at the second step in diacid production, i.e. the conversion of the alcohol to the aldehyde. This ω-hydroxy fatty acid has been found to interfere with purification of the diacid and causes a significant loss in recovery. Therefore, it is important to reduce the level of ω-hydroxy fatty acids produced in the fermentation. Since the substrate specificity tests and $K_m$ determinations performed with FAO1 and FAO2 indicated that FAO1 was the predominant fatty alcohol oxidase produced during the HOSFFA fermentation, amplification of the FAO1 gene was initially pursued.

Amplification cassettes with PacI restriction sites at the ends of the FAO1 and FAO2 genes were prepared as described in Materials and Methods (Example 1). Neither of these constructs has been tested in *Candida tropicalis*, however. A construct in which the promoter from the CYP52A2 gene replaced the native promoter in FAO1 was successfully prepared (SEQ ID NO:7) and transformed into *Candida tropicalis*. The CYP52A2 gene encodes a cytochrome P450 monooxygenase that is part of the hydroxylase complex responsible for catalyzing the first step in diacid production, i.e. the conversion of the fatty acid to the alcohol. By fusing the promoter region of this gene to the ORF of the FAO1 gene, it was hypothesized that the alcohol oxidase gene and corresponding enzyme would be induced earlier and more strongly than it might otherwise be. This would make the conversion to the diacid faster and help to reduce the bottleneck at this point in the reaction. Three clones, named HDC40-1, HDC40-5 and HDC40-7 were selected for testing in fermentors. By comparing band intensities in a Southern blot analysis and estimating copy numbers, HDC40-1 appears to have a low (one additional copy of FAO1) copy number; HDC40-5 has a higher copy number (two additional copies); and HDC40-7 has multiple additional copies per cell.

Figure 7:
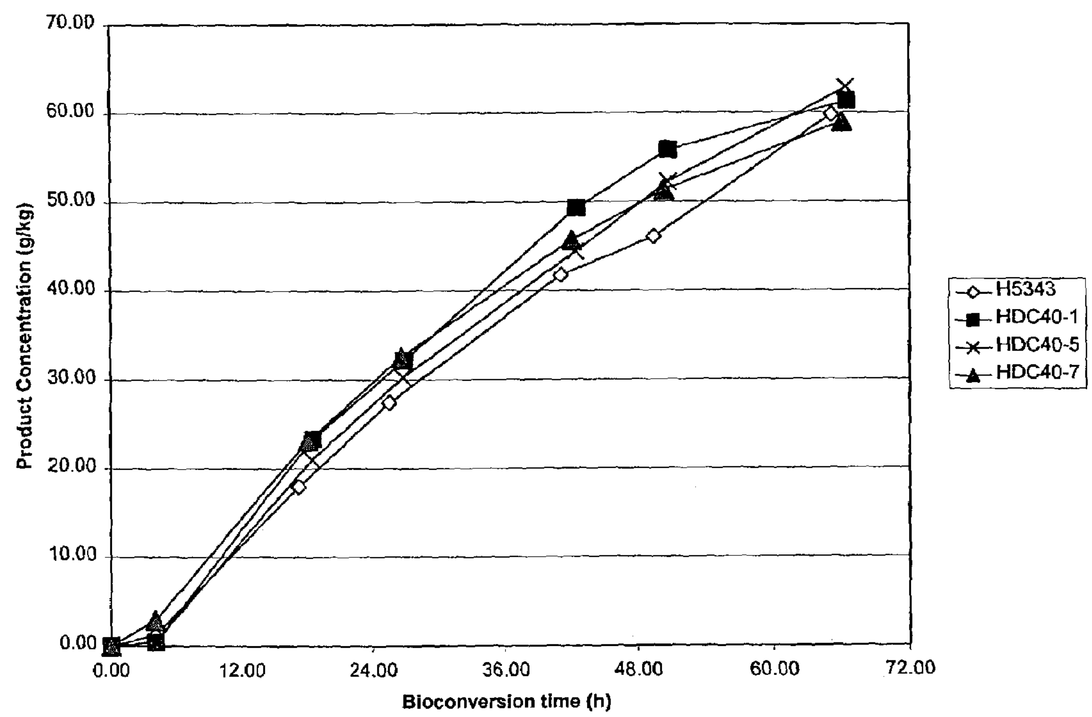
FIG. 7 graphically depicts a comparison of productivity in fermentations with FAO-amplified strains or base strain, H5343.
Figure 8:
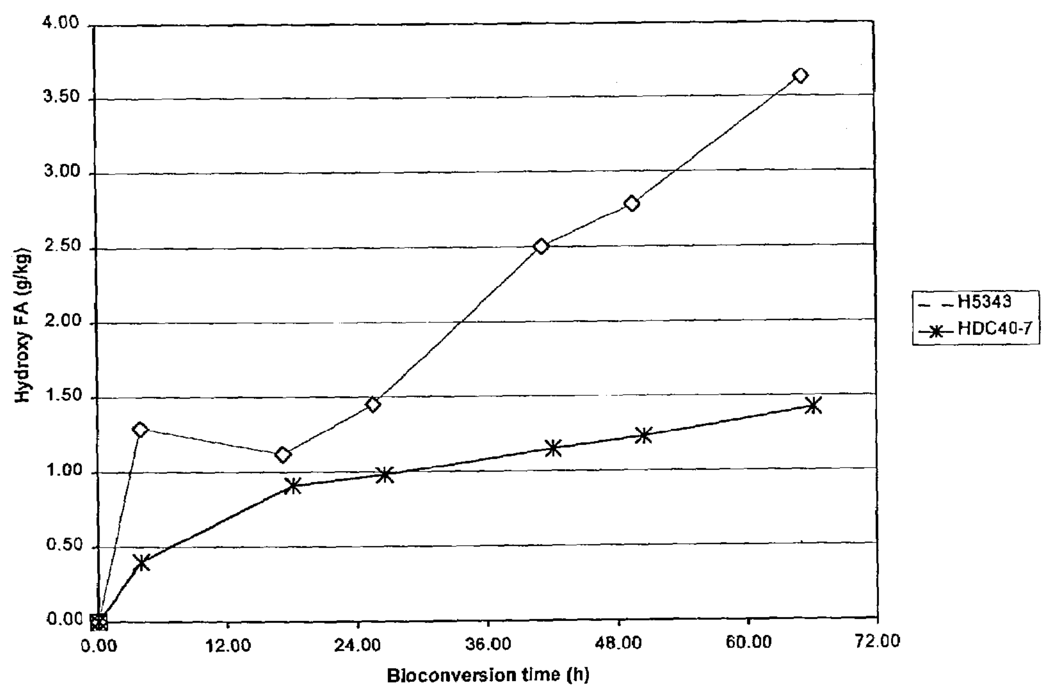
FIG. 8 graphically depicts a comparison of ω-hydroxy-fatty acid concentration in fermentations with FAO-amplified strain, HDC40-7, or base strain, H5343.
Figure 9:
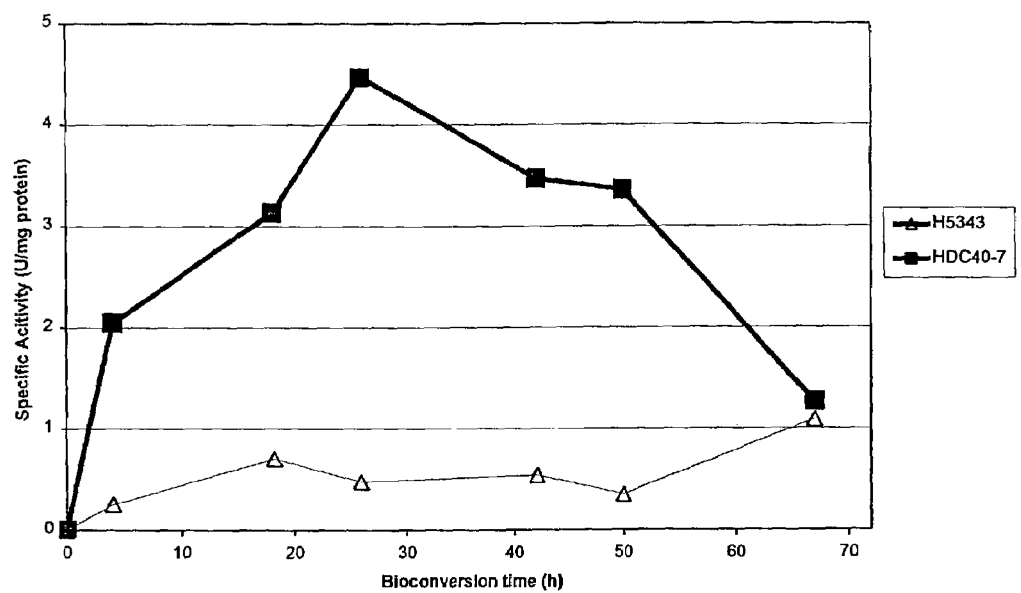
FIG. 9 graphically depicts a comparison of alcohol oxidase activity between the FAO1-amplified strain, HDC40-7, and the base strain, H5343.
Figure 10:
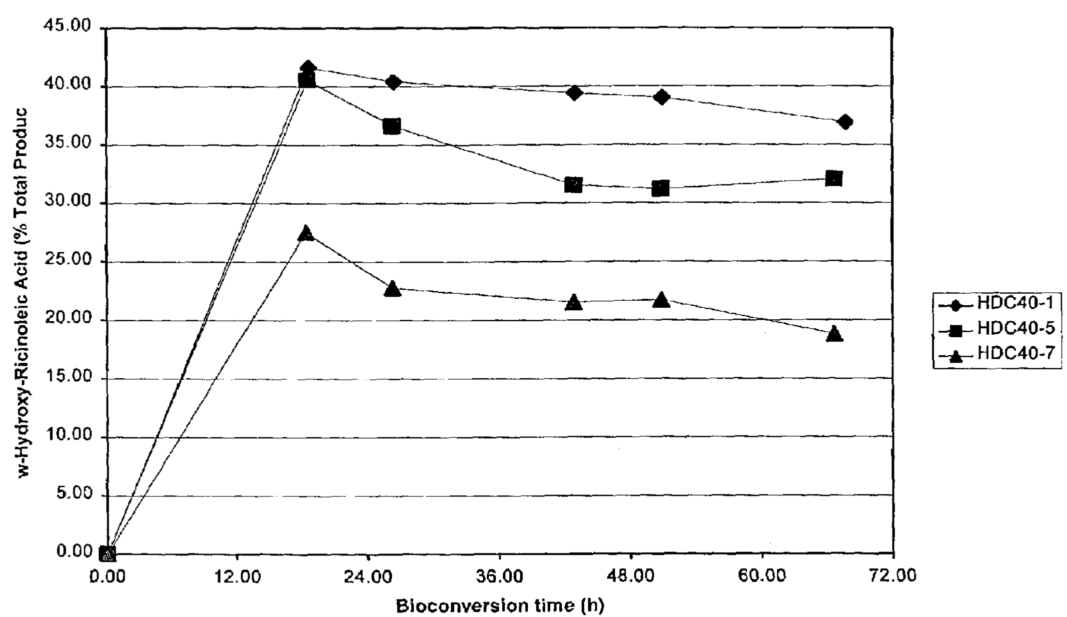
FIG. 10 graphically depicts a comparison of ω-hydroxy-fatty acid concentration in fermentations with FAO-amplified strains, HDC40-1, HDC40-5, or HDC40-7, using ricinoleic acid as substrate.

These strains were tested in fermentations with HOSFFA as substrate. FIG. 7 shows that, under similar fermentation conditions, all strains produced more diacid than the base strain, H5343. Both HDC40-1 and HDC40-7 had similar initial productivity values up to about 24 h of bioconversion time. HDC40-1, however, maintained a higher level of productivity than HDC40-7 over the next 48 h. FIG. 8 shows the level of ω-hydroxy fatty acids produced in HDC40 strains, relative to the base strain, H5343, which has no amplified genes. Note that, although there is still some ω-hydroxy fatty acids produced, the levels are considerably reduced, compared to H5343. An alcohol oxidase activity profile (FIG. 9) determined over the course of the fermentation demonstrates that the alcohol oxidase, as expected, has been considerably amplified and is very active during the early hours of the fermentation. When ricinoleic acid is used as a fermentation substrate in place of HOSFFA, high levels of ω-hydroxy fatty acids (relative to the amount of diacid produced) are detected during the fermentation. For this reason, ricinoleic acid fermentations are a more definitive test of the effectiveness of the FAO1 amplification. When HDC40-1, HDC40-5 and HDC40-7 fermentations were compared, it was discovered that the FAO1 gene copy number inversely correlated with the reduced level of ω-hydroxy fatty acids, i.e. the percent of ω-hydroxy fatty acids produced relative to the total level of oxidized product (FIG. 10).

EXAMPLE 10

Identification of Signature Motifs Unique to FAO1 and FAO2

The amino acid sequences corresponding to the subject FAO1 and FAO2 genes were examined for the presence of one or more of the seven peptide sequences identified by Slabas et al. (12) as indicative of an FAO gene. Table 7 shows a comparison of the signature peptides identified by Slabas et al. among the FOA1 and FAO2 genes of the present invention, and the FAOT gene of *C. tropicalis*. Also compared are similar sequences from the *Candida albicans* FAO enzyme (FAOCA). As reflected in Table 7, all seven FAOT peptides agree with the signature peptides identified by Slabas et al. Six out of the seven FAO1 peptides but only four of the seven FAO2 peptides agree with the signature peptides. Interestingly, although FAO2 is closest to FAOT in amino acid sequence identity and similarity (Table 3), FAO1 is most similar to FAOT when the seven signature peptides are compared.

Peptide 4 of FAO1 and FAO2 (CGFCYLGC) is a unique peptide, not found in previously characterized FAOs. Peptide 1 of FAO2a and FAO2b (IIGSGAGAGVMA) as well as peptide 4 of both FAO1 [and] FAO2a and FAO2b (CGFCYLGC) is also a unique peptide, not found in previously characterized FAOs.

TABLE 7

Comparison of Signature Peptides of Cognis' FAO1 and FAO2 with *C. tropicalis* FAOT and *C. albicans* FAOCA

| | Peptide 1 | Peptide 2 | Peptide 3 | Peptide 4 | Peptide 5 | Peptide 6 | Peptide 7 |
|---|---|---|---|---|---|---|---|
| Signature Peptide[1,2] | IIGSG(X)GAGVVA (SEQ ID NO:15) | AGSTFGGG (SEQ ID NO:18) | NWSACLKTP (SEQ ID NO:20) | CG(X)CHLGC (SEQ ID NO:22) | IG(X)NL(X)LHPVS (SEQ ID NO:24) | SAHQMS(X)CRMSG (SEQ ID NO:27) | PTASG(X)NPM (SEQ ID NO:30) |
| FAOT | IIGSGAGAGVVA (SEQ ID NO:16) | AGSTFGGG (SEQ ID NO:18) | NWSACLKTP (SEQ ID NO:20) | CGFCHLGC (SEQ ID NO:23) | IGKNLTLHPVS (SEQ ID NO:25) | SAHQMSTCRMSG (SEQ ID NO:28) | PTASGANPM (SEQ ID NO:31) |

TABLE 7-continued

Comparison of Signature Peptides of Cognis' FAO1 and FAO2 with *C. tropicalis* FAOT and *C. albicans* FAOCA

| | Peptide 1 | Peptide 2 | Peptide 3 | Peptide 4 | Peptide 5 | Peptide 6 | Peptide 7 |
|---|---|---|---|---|---|---|---|
| FAO1 | IIGSGAGAGVVA (SEQ ID NO:16) | AGSTFGGG (SEQ ID NO:18) | NWSACLKTP (SEQ ID NO:20) | CGFCYLGC (SEQ ID NO:13) | IGKNLTLHPVS (SEQ ID NO:25) | SAHQMSSCRMSG (SEQ ID NO:29) | PTASGANPM (SEQ ID NO:31) |
| FAO2a | IIGSGAGAGV**MA** (SEQ ID NO:14) | AGSTLGGG (SEQ ID NO:19) | NWSACLKTP (SEQ ID NO:20) | CGFCYLGC (SEQ ID NO:13) | IGKNLTLHPVS (SEQ ID NO:25) | SAHQMSTCRMSG (SEQ ID NO:28) | PTASGANPM (SEQ ID NO:31) |
| FAO2b | IIGSGAGAGV**MA** (SEQ ID NO:14) | AGSTLGGG (SEQ ID NO:19) | NWSACLKTP (SEQ ID NO:20) | CGFCYLGC (SEQ ID NO:13) | IGKNLTLHPVS (SEQ ID NO:25) | SAHQMSTCRMSG (SEQ ID NO:28) | PTASGANPM (SEQ ID NO:31) |
| FAOCA | IIGSGAG**S**GVVA (SEQ ID NO:17) | AGSTFGGG (SEQ ID NO:18) | NWSACIKTP (SEQ ID NO:21) | CGFCHLGC (SEQ ID NO:23) | IGANLTLHPVT (SEQ ID NO:26) | SAHQMSSCRMSG (SEQ ID NO:29) | PTASGANPM (SEQ ID NO:31) |

[1]Amino acids in bold indicate amino acid differences from signature peptide
[2](X) indicates that any amino acid may be at this position

REFERENCES

1. Kemp G D, Dickinson M, Ratledge C (1988) "Inducible long chain alcohol oxidase from alkane-grown *Candida tropicalis*." Appl. Microbiol. Biotechnol. 29:370–374.
2. Kemp G D, Dickinson F M, Ratledge C (1991) "Activity and substrate specificity of the fatty alcohol oxidase of *Candida tropicalis* in organic solvents." Appl. Microbiol. Biotechnol. 34:441–445.
3. Dickinson F M, Wadforth C (1992) "Purification and some properties of alcohol oxidase from alkane-grown *Candida tropicalis*." Bichem. J. 282:325–331.
4. Vanhanen S, West M, Kroon J T M, Lindner N, Casey J, Cheng Q, Elborough K M, Slabas A R (2000) "A consensus sequence for long-chain fatty-acid alcohol oxidases from *Candida* identifies a family of genes involved in lipid-oxidation in yeast with homologues in plants and bacteria." J. Biol. Chem. 275:4445–4452.
5. Blasig R, Mauersberger S, Riege R, Schunck W H, Jockisch W, Franke P (1988) "Degradation of long-chain n-alkanes by the yeast *Candida maltosa*. II. Oxidation of n-alkanes and intermediates using microsomal membrane fractions." Appl. Microbiol. Biotechnol. 28:589–597.
6. Mauersberger S, Drechsler H, Oehme G, Müller H G (1992) "Substrate specificity and stereoselectivity of fatty alcohol oxidase from the yeast *Candida maltosa*." Appl. Microbiol. Biotechnol. 37:66–73.
7. Ilchenko A P, Tsfasman I M (1988) "Isolation and characterization of alcohol oxidase from higher alcohols of the yeast *Torulopsis candida* grown on hexadecane." Biokhimiya 53:263–271.
8. Hommel R, Ratledge C (1990) "Evidence for two fatty alcohol oxidases in the biosurfactant-producing yeast *Candida* (Torulopsis) *bombicola*." FEMS Microbiol. Lett. 70:183–186.
9. Hommel R, Lassner D, Weiss J, Kleber H P (1994) "The inducible microsomal fatty alcohol oxidase of *Candida* (Torulopsis) *apicola*." Appl. Microbiol. Biotechnol. 40:729–734.
10. Kemp G D, Dickinson F M, Ratledge C (1990) "Light sensitivity of the n-alkane-induced fatty alcohol oxidase from *Candida tropicalis* and *Yarrowia lipolytica*." Appl. Microbiol. Biotechnol. 32:461–464.
11. Eirich L D (1989) "Partial characterization of 12-hydroxylauric acid oxidase in *Candida tropicalis*" Topical Report Ei2/89.
12. Slabas A R, Elborough K, Vanhanen S, West M, Cheng Q, Lindner N, Casey J, Sanglard D (1999) "Improvements in or relating to fatty acid metabolism" International Patent Application WO 99/47685.
13. Fürste J P, Pansegrau W, Frank R, Blöcker H, Scholz P, Bagdasarian M, Lanka E. (1986) "Molecular cloning of the plasmid RP4 primase region in a multi-host-range tacP expression vector." Gene 48:119–131.
14. Ueda T, Suzuki T, Yokogawa T, Nishikawa K, Watanabe K (1994) "Unique structure of new serine tRNAs responsible for decoding leucine codon CUG in various Candida species and their putative ancestral tRNA genes." Biochimie 76:1217–1222.

What is claimed is:

1. An isolated nucleic acid molecule that encodes a fatty alcohol oxidase having the amino acid sequence of SEQ ID NO:2.

2. The isolated nucleic acid molecule of claim 1 comprising the nucleotide sequence of SEQ ID NO:1.

3. A vector comprising the isolated nucleic acid molecule of claim 1.

4. A vector comprising the isolated nucleic acid molecule of claim 2.

5. The vector of claim 3 wherein the vector is a plasmid, phagemid, phage, cosmid, or linear DNA vector.

6. The vector of claim 4 wherein the vector is a plasmid, phagemid, phage, cosmid, of linear DNA vector.

7. A host cell transformed with the vector of claim 3.

8. A host cell transformed with the vector of claim 4.

9. The host cell of claim 7 wherein the cell is a bacterial cell, fungal cell, insect cell; animal cell or plant cell.

10. The host cell of claim 8 wherein the cell is a bacterial cell, fungal cell, insect cell, animal cell or plant cell.

11. The fungal cell of claim 9 wherein the fungal cell is a yeast cell selected from the group consisting of *Yarrowia* sp., *Bebaromyces* sp., *Saccharomyces* sp., *Schizosaccharomyces* sp., *Pichia* sp. and *Candida* sp.

12. The fungal cell of claim 10 wherein the fungal cell is a yeast cell selected from the: group consisting of *Yarrowia* sp., *Bebaromyces* sp., *Saccharomyces* sp., *Schizosaccharomyces* sp., *Pichia* sp. and *Candida* sp.

13. The isolated nucleic acid molecule of claim 1 further comprising an isolated nucleic acid molecule encoding the signature motif of SEQ ID NO:13, where the encoded fatty alcohol oxidase continues to have fatty alcohol oxidase activity.

14. The isolated molecule of claim 13, wherein SEQ ID NO: 13 is encoded by the nucleotide sequence:

TGY GGN TTY TGY TAY YTN GGN TGY of SEQ liD NO. 32, wherein:

Y is C or T, and N is A or G, or C or T.

15. An isolated nucleic acid molecule comprising a nucleotide sequence which encodes the signature motif of SEQ ID NO:13 and which hybridizes under high stringency conditions to nucleotides 1941–4054 of the nucleotide sequence of SEQ ID NO:1, wherein the nucleic acid molecule encodes a fatty alcohol oxidase and said high stringency condition is 0.1–1×SSC/0.1% (w/v) SDS at greater than or equal to 60° C. for 1–3 hours.

16. An isolated nucleic acid molecule comprising an open reading frame (ORF) for a fatty alcohol oxidase (FAO) polynucleotide from *Candida tropicalis* wherein the ORF is operably linked to a promoter which regulates the expression of the ORF and said ORF encodes the amino acid sequence of SEQ. ID NO:2.

17. The isolated nucleic acid molecule of claim 16 wherein the ORF comprises nucleotides 1941–4054 of the nucleotide sequence SEQ ID NO:1.

18. The isolated nucleic acid molecule of claim 16 wherein the promoter is a cytochrome p450 monooxygenase promoter.

19. The isolated nucleic acid molecule of claim 18, wherein the promoter comprises the nucleotide sequence of SEQ ID NO:7.

20. A vector comprising the isolated nucleic acid molecule of claim 16.

21. A vector comprising the isolated nucleic acid molecule of claim 17.

22. A vector comprising the isolated nucleic acid molecule of claim 18.

23. A vector comprising the isolated nucleic acid molecule of claim 19.

24. The vector of claim 20 wherein the vector is a plasmid, phagemid, phage, cosmid, or linear DNA vector.

25. The vector of claim 21 wherein the vector is a plasmid, phagemid, phage, cosmid, or linear DNA vector.

26. The vector of claim 22 wherein the vector is a plasmid, phagemid, phage, cosmid, or linear DNA vector.

27. The vector of claim 23 wherein the vector is a plasmid, phagemid, phage, cosmid, or linear DNA vector.

28. An isolated host cell transformed with the isolated nucleic acid molecule of claim 16.

29. An isolated host cell transformed with the isolated nucleic acid molecule of claim 17.

30. An isolated host cell transformed with the isolated nucleic acid molecule of claim 18.

31. An isolated host cell transformed with the isolated nucleic acid molecule of claim 19.

32. An isolated host cell transformed with the vector of claim 20.

33. An isolated host cell transformed with the vector of claim 21.

34. An isolated host cell transformed with the vector of claim 22.

35. An isolated host cell transformed with the vector of claim 23.

36. A method of producing a fatty alcohol oxidase (FAO1) protein, said method comprising: transforming a suitable isolated host cell with a DNA sequence encoding a protein having the amino acid sequence of SEQ ID NO:2; and culturing the transformed cell and expressing the fatty alcohol oxidase (FAO1) protein.

* * * * *

SEQUENCE LISTING

```
<160> NUMBER OF SEQ ID NOS: 72

<210> SEQ ID NO 1
<211> LENGTH: 4296
<212> TYPE: DNA
<213> ORGANISM: Candida tropicalis
<220> FEATURE:
```

```
<221> NAME/KEY: CDS
<222> LOCATION: (1940)..(4051)

<400> SEQUENCE: 1

tgcatactcg gagcatatcg ccatcgtcca tatcgttggc actccatcca ctgagtcagc     60

caagaagcaa ttgttgttgc accacacctt aggtaatggt gactttactg ttttccacaa    120

gatctcgtca ttcatcagtg ccactactgc tgggttgacc gacccagaca ccgccgctga    180

tgaaattgat agagtgattg agtcagccta catcaaccag cgtccaacgt acttgggatt    240

cccttccaac atggttgacg ttcaagtgcc agtcagcaag ttggacaagc cattgaactt    300

aaccccacct gcaaacaatc caaagatcca gtctgaggtc ttgagcgaca ttattgcctt    360

gattgaaacc gccaaggatc cagttatcat cattgatgct tgttgtggaa ggcacaatgc    420

taccccagag gcacagaagt tgattgagtt gacaaagttc aagtttgctg tcaccccaat    480

ggctaaaggg tctaaggaca ttgatgaaag tgatccgaag ttcattggtt gctacgttgg    540

tgacttgtct tatccaagag tcaaagagtt ggttgaaagc tcggacttgg tcttgtcctt    600

gggtgctgtc ttgtctgatt tcaacactgg ttcgttctca tactctttgg acaatgccaa    660

ggttgttgaa ttccactccg actacactca aatcaagagc gctcagtacc caggtatcag    720

aatgaaggaa ttgttgggca agttggttga ggagccagaa ttggtcaaga cgtgttccaa    780

gatcccagca aagaagttgg tcactgacaa ctttgaacca ttggtcttgc caccggacca    840

caagctcacc caatcctggt tgtggagtaa cttgggtaat tggttgaaag aaggtgatgt    900

gattgttacc gaaaccggta cttccaattt cggtattgtc cagaccaaat tcccaaagaa    960

tgctgtcggt atctcgcaag tcttgtgggg ttccattggc tactcggtcg gttctgccgc   1020

tggtgccgtt atcgccgccg aggagcttga tcccagccgt agagtcatct tgtttgttgg   1080

tgacggttct ttgcagttga ccgtgcagga aatctccacc atggccagac acaagaacaa   1140

catctacatc tttgtcttga acaacaacgg tttcaccatt gaaagattga ttcacggtcc   1200

agaagctggt tacaacagta ttcaagaatg ggagaacgct gagttattga agactttcaa   1260

ggctaccaac tacgagagtt tcaccgtcaa gactgtcggc gaacttgaca aggtgttcaa   1320

ggatgaaaag tttgccgtca acgacaagat tagattggtt gagatcatgt tagacacttt   1380

cgatgctcca gagaacttgg ttaagcaagc tgagagatct gccaacacca acaagtagag   1440

tttgtctatg ttttccgttt gccttttctt tctagtacga gacgttattg aacgaagttt   1500

ttatatatct agatctaata catattccat gtctgttcat ttttgacgga gtttcataag   1560

gtggcagttt ctaatcaaag gtccgtcatt ggcgtcgtgg cattggcggc tcgcatcaac   1620

tcgtatgtca atattttctg ttaactccgc cagacatacg atcaaaacct acaagcaaaa   1680

aaattccaca tgctttgttt gagatctcca caaacaacaa cggggtaaga aaatcatggg   1740

gcgattaatc atgccatctt tgtaaatttc tttgtttcaa catcaccctc tttagtcaaa   1800

ccttcacagg actgtctgct ctactttgcc acccagttca tatataaatt accaacttcc   1860

accgagcacc accaacacct caccccactc tctccccccc ccttttttt ccagcttaga   1920

cacacacttc aaactcgac atg gct cca ttt ttg ccc gac cag gtc gac tac    1972
                     Met Ala Pro Phe Leu Pro Asp Gln Val Asp Tyr
                     1               5                   10

aaa cac gtc gac acc ctt atg tta tta tgt gac ggg atc atc cac gaa     2020
Lys His Val Asp Thr Leu Met Leu Leu Cys Asp Gly Ile Ile His Glu
            15                  20                  25

acc acc gtg gac gaa atc aaa gac gtc att gcc cct gac ttc ccc gcc     2068
Thr Thr Val Asp Glu Ile Lys Asp Val Ile Ala Pro Asp Phe Pro Ala
```

-continued

```
        30                  35                  40

gac aaa tac gag gag tac gtc agg aca ttc acc aaa ccc tcc gaa acc     2116
Asp Lys Tyr Glu Glu Tyr Val Arg Thr Phe Thr Lys Pro Ser Glu Thr
    45                  50                  55

cca ggg ttc agg gaa acc gtc tac aac acc gtc aac gca aac acc atg     2164
Pro Gly Phe Arg Glu Thr Val Tyr Asn Thr Val Asn Ala Asn Thr Met
60                  65                  70                  75

gat gca atc cac cag ttc att atc ttg acc aat gtt ttg gga tca agg     2212
Asp Ala Ile His Gln Phe Ile Ile Leu Thr Asn Val Leu Gly Ser Arg
                80                  85                  90

gtc ttg gca cca gct ttg acc aac tcg ttg act cct atc aag gac atg     2260
Val Leu Ala Pro Ala Leu Thr Asn Ser Leu Thr Pro Ile Lys Asp Met
            95                  100                 105

agc ttg gaa gac cgt gaa aag ttg tta gcc tcg tgg cgt gac tcc cct     2308
Ser Leu Glu Asp Arg Glu Lys Leu Leu Ala Ser Trp Arg Asp Ser Pro
        110                 115                 120

att gct gct aaa agg aag ttg ttc agg ttg gtt tct acg ctt acc ttg     2356
Ile Ala Ala Lys Arg Lys Leu Phe Arg Leu Val Ser Thr Leu Thr Leu
    125                 130                 135

gtc acg ttc acg aga ttg gcc aat gag ttg cat ttg aaa gcc att cat     2404
Val Thr Phe Thr Arg Leu Ala Asn Glu Leu His Leu Lys Ala Ile His
140                 145                 150                 155

tat cca gga aga gaa gac cgt gaa aag gct tat gaa acc cag gag att     2452
Tyr Pro Gly Arg Glu Asp Arg Glu Lys Ala Tyr Glu Thr Gln Glu Ile
                160                 165                 170

gac cct ttt aag tac cag ttt ttg gaa aaa ccg aag ttt tac ggc gct     2500
Asp Pro Phe Lys Tyr Gln Phe Leu Glu Lys Pro Lys Phe Tyr Gly Ala
            175                 180                 185

gag ttg tac ttg cca gat att gat gtg atc att att gga tct ggg gcc     2548
Glu Leu Tyr Leu Pro Asp Ile Asp Val Ile Ile Ile Gly Ser Gly Ala
        190                 195                 200

ggt gct ggt gtc gtg gcc cac act ttg acc aac gac ggc ttc aag agt     2596
Gly Ala Gly Val Val Ala His Thr Leu Thr Asn Asp Gly Phe Lys Ser
    205                 210                 215

ttg gtt ttg gaa aag ggc aga tac ttt agc aac tcc gag ttg aac ttt     2644
Leu Val Leu Glu Lys Gly Arg Tyr Phe Ser Asn Ser Glu Leu Asn Phe
220                 225                 230                 235

gat gac aag gac ggg gtt caa gaa tta tac caa agt gga ggt act ttg     2692
Asp Asp Lys Asp Gly Val Gln Glu Leu Tyr Gln Ser Gly Gly Thr Leu
                240                 245                 250

acc acc gtc aac cag cag ttg ttt gtt ctt gct ggt tcc act ttt ggt     2740
Thr Thr Val Asn Gln Gln Leu Phe Val Leu Ala Gly Ser Thr Phe Gly
            255                 260                 265

ggt ggt acc act gtc aat tgg tcg gcc tgt ctt aaa acg cca ttc aag     2788
Gly Gly Thr Thr Val Asn Trp Ser Ala Cys Leu Lys Thr Pro Phe Lys
        270                 275                 280

gtg cgt aag gaa tgg tat gat gag ttt ggc gtt gac ttt gct gcc gat     2836
Val Arg Lys Glu Trp Tyr Asp Glu Phe Gly Val Asp Phe Ala Ala Asp
    285                 290                 295

gaa gcc tac gac aaa gca cag gat tat gtt tgg cag caa atg gga gct     2884
Glu Ala Tyr Asp Lys Ala Gln Asp Tyr Val Trp Gln Gln Met Gly Ala
300                 305                 310                 315

tct acc gaa ggc atc acc cac tct ttg gct aac gag att att att gaa     2932
Ser Thr Glu Gly Ile Thr His Ser Leu Ala Asn Glu Ile Ile Ile Glu
                320                 325                 330

ggt ggc aag aaa tta ggt tac aag gcc aag gta tta gac caa aac agc     2980
Gly Gly Lys Lys Leu Gly Tyr Lys Ala Lys Val Leu Asp Gln Asn Ser
            335                 340                 345

ggt ggt cat cct cat cac aga tgc ggt ttc tgt tat ttg ggt tgt aag     3028
```

-continued

```
Gly Gly His Pro His His Arg Cys Gly Phe Cys Tyr Leu Gly Cys Lys
        350                 355                 360

cac ggt atc aag cag ggc tct gtt aat aac tgg ttt aga gac gca gct      3076
His Gly Ile Lys Gln Gly Ser Val Asn Asn Trp Phe Arg Asp Ala Ala
    365                 370                 375

gcc cac ggt tct cag ttc atg caa cag gtt aga gtt ttg caa atc ctt      3124
Ala His Gly Ser Gln Phe Met Gln Gln Val Arg Val Leu Gln Ile Leu
380                 385                 390                 395

aac aag aag ggc atc gct tat ggt atc ttg tgt gag gat gtt gta acc      3172
Asn Lys Lys Gly Ile Ala Tyr Gly Ile Leu Cys Glu Asp Val Val Thr
                400                 405                 410

ggt gcc aag ttc acc att act ggc ccc aaa aag ttt gtt gtt gcc gcc      3220
Gly Ala Lys Phe Thr Ile Thr Gly Pro Lys Lys Phe Val Val Ala Ala
            415                 420                 425

ggc gcc tta aac act cca tct gtg ttg gtc aac tcc gga ttc aag aac      3268
Gly Ala Leu Asn Thr Pro Ser Val Leu Val Asn Ser Gly Phe Lys Asn
        430                 435                 440

aag aac atc ggt aag aac tta act ttg cat cca gtt tct gtc gtg ttt      3316
Lys Asn Ile Gly Lys Asn Leu Thr Leu His Pro Val Ser Val Val Phe
    445                 450                 455

ggt gat ttt ggc aaa gac gtt caa gca gat cac ttc cac aac tcc atc      3364
Gly Asp Phe Gly Lys Asp Val Gln Ala Asp His Phe His Asn Ser Ile
460                 465                 470                 475

atg act gct ctt tgt tca gaa gcc gct gat tta gac ggc aag ggt cat      3412
Met Thr Ala Leu Cys Ser Glu Ala Ala Asp Leu Asp Gly Lys Gly His
                480                 485                 490

gga tgc aga att gaa acc atc ttg aac gct cca ttc atc cag gct tca      3460
Gly Cys Arg Ile Glu Thr Ile Leu Asn Ala Pro Phe Ile Gln Ala Ser
            495                 500                 505

ttc tta cca tgg aga ggt agt aac gag gct aga cga gac ttg ttg cgt      3508
Phe Leu Pro Trp Arg Gly Ser Asn Glu Ala Arg Arg Asp Leu Leu Arg
        510                 515                 520

tac aac aac atg gtg gcc atg tta ctt ctt agt cgt gat acc acc agt      3556
Tyr Asn Asn Met Val Ala Met Leu Leu Leu Ser Arg Asp Thr Thr Ser
    525                 530                 535

ggt tcc gtt tcg tcc cat cca act aaa cct gaa gca tta gtt gtc gag      3604
Gly Ser Val Ser Ser His Pro Thr Lys Pro Glu Ala Leu Val Val Glu
540                 545                 550                 555

tac gac gtg aac aag ttt gac aga aac tcc atc ttg cag gca ttg ttg      3652
Tyr Asp Val Asn Lys Phe Asp Arg Asn Ser Ile Leu Gln Ala Leu Leu
                560                 565                 570

gtc act gct gac ttg ttg tac att caa ggt gcc aag aga atc ctt agt      3700
Val Thr Ala Asp Leu Leu Tyr Ile Gln Gly Ala Lys Arg Ile Leu Ser
            575                 580                 585

ccc caa cca tgg gtg cca att ttt gaa tcc gac aag cca aag gat aag      3748
Pro Gln Pro Trp Val Pro Ile Phe Glu Ser Asp Lys Pro Lys Asp Lys
        590                 595                 600

aga tca atc aag gac gag gac tat gtc gaa tgg aga gcc aag gtt gcc      3796
Arg Ser Ile Lys Asp Glu Asp Tyr Val Glu Trp Arg Ala Lys Val Ala
    605                 610                 615

aag att cct ttt gac acc tac ggc tcg cct tat ggt tcg gcg cat caa      3844
Lys Ile Pro Phe Asp Thr Tyr Gly Ser Pro Tyr Gly Ser Ala His Gln
620                 625                 630                 635

atg tct tct tgt cgt atg tca ggt aag ggt cct aaa tac ggt gct gtt      3892
Met Ser Ser Cys Arg Met Ser Gly Lys Gly Pro Lys Tyr Gly Ala Val
                640                 645                 650

gat acc gat ggt aga ttg ttt gaa tgt tcg aat gtt tat gtt gct gac      3940
Asp Thr Asp Gly Arg Leu Phe Glu Cys Ser Asn Val Tyr Val Ala Asp
            655                 660                 665
```

-continued

```
gct agt ctt ttg cca act gct agc ggt gct aat cct atg gtc acc acc      3988
Ala Ser Leu Leu Pro Thr Ala Ser Gly Ala Asn Pro Met Val Thr Thr
        670                 675                 680

atg act ctt gca aga cat gtt gcg tta ggt ttg gca gac tcc ttg aag      4036
Met Thr Leu Ala Arg His Val Ala Leu Gly Leu Ala Asp Ser Leu Lys
    685                 690                 695

acc aag gcc aag ttg tagttctgta tacgtatctt ataatttaga tttcctttta      4091
Thr Lys Ala Lys Leu
700

ttgacggtaa acattcagga taggtactac ccttgctgca aaagcccagc acgccccaat   4151

cgcgatgact tgagcgaagc aaacacgcac acaaaagggg tacacaaaaa ataacgagat   4211

gcccttgaag cacacaccca aacacgatgg aacacaagat ggccctagaa agtacaaaaa   4271

aagtaaagcc acttgattcc gccca                                         4296


<210> SEQ ID NO 2
<211> LENGTH: 704
<212> TYPE: PRT
<213> ORGANISM: Candida tropicalis

<400> SEQUENCE: 2

Met Ala Pro Phe Leu Pro Asp Gln Val Asp Tyr Lys His Val Asp Thr
1               5                   10                  15

Leu Met Leu Leu Cys Asp Gly Ile Ile His Glu Thr Thr Val Asp Glu
            20                  25                  30

Ile Lys Asp Val Ile Ala Pro Asp Phe Pro Ala Asp Lys Tyr Glu Glu
        35                  40                  45

Tyr Val Arg Thr Phe Thr Lys Pro Ser Glu Thr Pro Gly Phe Arg Glu
    50                  55                  60

Thr Val Tyr Asn Thr Val Asn Ala Asn Thr Met Asp Ala Ile His Gln
65                  70                  75                  80

Phe Ile Ile Leu Thr Asn Val Leu Gly Ser Arg Val Leu Ala Pro Ala
                85                  90                  95

Leu Thr Asn Ser Leu Thr Pro Ile Lys Asp Met Ser Leu Glu Asp Arg
            100                 105                 110

Glu Lys Leu Leu Ala Ser Trp Arg Asp Ser Pro Ile Ala Ala Lys Arg
        115                 120                 125

Lys Leu Phe Arg Leu Val Ser Thr Leu Thr Leu Val Thr Phe Thr Arg
    130                 135                 140

Leu Ala Asn Glu Leu His Leu Lys Ala Ile His Tyr Pro Gly Arg Glu
145                 150                 155                 160

Asp Arg Glu Lys Ala Tyr Glu Thr Gln Glu Ile Asp Pro Phe Lys Tyr
                165                 170                 175

Gln Phe Leu Glu Lys Pro Lys Phe Tyr Gly Ala Glu Leu Tyr Leu Pro
            180                 185                 190

Asp Ile Asp Val Ile Ile Ile Gly Ser Gly Ala Gly Ala Gly Val Val
        195                 200                 205

Ala His Thr Leu Thr Asn Asp Gly Phe Lys Ser Leu Val Leu Glu Lys
    210                 215                 220

Gly Arg Tyr Phe Ser Asn Ser Glu Leu Asn Phe Asp Asp Lys Asp Gly
225                 230                 235                 240

Val Gln Glu Leu Tyr Gln Ser Gly Gly Thr Leu Thr Thr Val Asn Gln
                245                 250                 255

Gln Leu Phe Val Leu Ala Gly Ser Thr Phe Gly Gly Gly Thr Thr Val
            260                 265                 270
```

-continued

```
Asn Trp Ser Ala Cys Leu Lys Thr Pro Phe Lys Val Arg Lys Glu Trp
        275                 280                 285

Tyr Asp Glu Phe Gly Val Asp Phe Ala Ala Asp Glu Ala Tyr Asp Lys
    290                 295                 300

Ala Gln Asp Tyr Val Trp Gln Gln Met Gly Ala Ser Thr Glu Gly Ile
305                 310                 315                 320

Thr His Ser Leu Ala Asn Glu Ile Ile Ile Glu Gly Gly Lys Lys Leu
                325                 330                 335

Gly Tyr Lys Ala Lys Val Leu Asp Gln Asn Ser Gly Gly His Pro His
            340                 345                 350

His Arg Cys Gly Phe Cys Tyr Leu Gly Cys Lys His Gly Ile Lys Gln
        355                 360                 365

Gly Ser Val Asn Asn Trp Phe Arg Asp Ala Ala Ala His Gly Ser Gln
    370                 375                 380

Phe Met Gln Gln Val Arg Val Leu Gln Ile Leu Asn Lys Lys Gly Ile
385                 390                 395                 400

Ala Tyr Gly Ile Leu Cys Glu Asp Val Val Thr Gly Ala Lys Phe Thr
                405                 410                 415

Ile Thr Gly Pro Lys Lys Phe Val Val Ala Ala Gly Ala Leu Asn Thr
            420                 425                 430

Pro Ser Val Leu Val Asn Ser Gly Phe Lys Asn Lys Asn Ile Gly Lys
        435                 440                 445

Asn Leu Thr Leu His Pro Val Ser Val Val Phe Gly Asp Phe Gly Lys
    450                 455                 460

Asp Val Gln Ala Asp His Phe His Asn Ser Ile Met Thr Ala Leu Cys
465                 470                 475                 480

Ser Glu Ala Ala Asp Leu Asp Gly Lys Gly His Gly Cys Arg Ile Glu
                485                 490                 495

Thr Ile Leu Asn Ala Pro Phe Ile Gln Ala Ser Phe Leu Pro Trp Arg
            500                 505                 510

Gly Ser Asn Glu Ala Arg Arg Asp Leu Leu Arg Tyr Asn Asn Met Val
        515                 520                 525

Ala Met Leu Leu Leu Ser Arg Asp Thr Thr Ser Gly Ser Val Ser Ser
    530                 535                 540

His Pro Thr Lys Pro Glu Ala Leu Val Val Glu Tyr Asp Val Asn Lys
545                 550                 555                 560

Phe Asp Arg Asn Ser Ile Leu Gln Ala Leu Leu Val Thr Ala Asp Leu
                565                 570                 575

Leu Tyr Ile Gln Gly Ala Lys Arg Ile Leu Ser Pro Gln Pro Trp Val
            580                 585                 590

Pro Ile Phe Glu Ser Asp Lys Pro Lys Asp Lys Arg Ser Ile Lys Asp
        595                 600                 605

Glu Asp Tyr Val Glu Trp Arg Ala Lys Val Ala Lys Ile Pro Phe Asp
    610                 615                 620

Thr Tyr Gly Ser Pro Tyr Gly Ser Ala His Gln Met Ser Ser Cys Arg
625                 630                 635                 640

Met Ser Gly Lys Gly Pro Lys Tyr Gly Ala Val Asp Thr Asp Gly Arg
                645                 650                 655

Leu Phe Glu Cys Ser Asn Val Tyr Val Ala Asp Ala Ser Leu Leu Pro
            660                 665                 670

Thr Ala Ser Gly Ala Asn Pro Met Val Thr Thr Met Thr Leu Ala Arg
        675                 680                 685

His Val Ala Leu Gly Leu Ala Asp Ser Leu Lys Thr Lys Ala Lys Leu
```

-continued 690 695 700

<210> SEQ ID NO 3
<211> LENGTH: 4158
<212> TYPE: DNA
<213> ORGANISM: Candida tropicalis
<220> FEATURE:
<221> NAME/KEY: CDS
<222> LOCATION: (1521)..(3632)

<400> SEQUENCE: 3
tctcaccaag tacgagaacg agcttgttga tagagcttag acttgtcttt tgtatttgta 60
atctgacgtt gaccgtttga gtttttcctg tgatatcacg taaatctggc aaccagcttt 120
ctattttttt tgcaacactt tttctcttca ccactctcag aaccaatgcc accgaagaag 180
ggtctcaacc aggaggaaaa gctctcgtca atcctcgcct ggttccaaag cagccactgc 240
ttctatacgc tcaaagaggt tgaacagaag gctagcaaag cgtgcaagat ctcgtctatg 300
cagatcaagg acttggttgc aaccttagtc aacgaaggtt tagtggaaca ggaaaaatgt 360
gggaccacca acttgtactg gtcgttcccg tactcggaac acaaacgcaa gctacagaga 420
tacgagcagc taagacaatc cgttgccaaa cttcaagcga ataaaggcaa gttggcggaa 480
gagttgcgaa acgcgtgtgg tgagcgtgac atggacagca ataggctaaa ccggatgcaa 540
cagtgcgatc agcttgttca cgaggcggca cgcctccagg aggaactaaa actgtcgagg 600
cagagagata ccattgacga gttggttcag gccattgact tcttcaacga gctgatagag 660
accgtcctca gctacatcag ccatcagtcg gggaccagcg tgtcggtatt gaaaacggag 720
tttgagatac ccgcagaact agaagaggct ccccagataa acaatgccgg agttagtgcg 780
taaatcgagc atgcatacgt tggagagaaa tagagaaaca gatttccggt gaaacgctac 840
aacacagacg aggaatacag aatggaacat gacggaaata taatatccga ggaaagacga 900
aagtacgaca tggaactccg ttactgcaac atcgatcgtg ctagatacga catagaacaa 960
tgttgctatt acatggaaag ctgttgctac aatccagaat acggttgtac tcaagggaga 1020
tgaggctggg agccgagtgg tacataaata ggcatatagg accgtcactt ggtctaggat 1080
cgtgtagagg gtggaagagg taggcaagat ccattctaat ctactgagtg acggctaata 1140
tacgatcagc gttctcaggc gagcacagtc attcctcatt tctgtacata cgttgcccct 1200
ttatgttttt tttcacagga tgctcacgcc caacatttcc ccccacattt tattacccac 1260
attgagccgt caaatgcatt ttttttatcc gtcgcttgct aagacaaaat tccacatgct 1320
ttgtctcaga gtatataaac aacggggcaa aaaaacatgg ggttaatagc ttattcgtgg 1380
attgatattt ttatatttta gttcgcccct ttcgccacca agctcaattg gactatttgt 1440
cagtggtgta taagctagag attactagac tgcttttctg attcttgatt ttcccttttc 1500
attagttcca gtacctagag atg aat acc ttc ttg cca gac gtg ctc gaa tac 1553
Met Asn Thr Phe Leu Pro Asp Val Leu Glu Tyr
1 5 10 aaa cac gtc gac acc ctt ttg tta ttg tgt gac ggg atc atc cac gaa 1601
Lys His Val Asp Thr Leu Leu Leu Leu Cys Asp Gly Ile Ile His Glu
15 20 25 acc aca gtc gat cag atc aag gac gcc att gct ccc gac ttc cct gag 1649
Thr Thr Val Asp Gln Ile Lys Asp Ala Ile Ala Pro Asp Phe Pro Glu
30 35 40 gac cag tac gag gag tat ctc aag acc ttc acc aag cca tct gag acc 1697
Asp Gln Tyr Glu Glu Tyr Leu Lys Thr Phe Thr Lys Pro Ser Glu Thr
45 50 55

-continued

```
cct ggg ttc aga gaa gcc gtc tac gac acg atc aac gcc acc cca acc      1745
Pro Gly Phe Arg Glu Ala Val Tyr Asp Thr Ile Asn Ala Thr Pro Thr
60                  65                  70                  75

gat gcc gtg cac atg tgt att gtc ttg acc acc gca ttg gac tcc aga      1793
Asp Ala Val His Met Cys Ile Val Leu Thr Thr Ala Leu Asp Ser Arg
                80                  85                  90

atc ttg gcc ccc acg ttg acc aac tcg ttg acg cct atc aag gat atg      1841
Ile Leu Ala Pro Thr Leu Thr Asn Ser Leu Thr Pro Ile Lys Asp Met
            95                  100                 105

acc ttg aag gag cgt gaa caa ttg ttg gcc tct tgg cgt gat tcc ccg      1889
Thr Leu Lys Glu Arg Glu Gln Leu Leu Ala Ser Trp Arg Asp Ser Pro
        110                 115                 120

att gcg gca aag aga aga ttg ttc aga ttg att tcc tcg ctt acc ttg      1937
Ile Ala Ala Lys Arg Arg Leu Phe Arg Leu Ile Ser Ser Leu Thr Leu
    125                 130                 135

acg acg ttt acg aga ttg gcc agc gaa ttg cac ttg aaa gcc atc cac      1985
Thr Thr Phe Thr Arg Leu Ala Ser Glu Leu His Leu Lys Ala Ile His
140                 145                 150                 155

tac cct ggc aga gac ttg cgt gaa aag gcg tat gaa acc cag gtg gtt      2033
Tyr Pro Gly Arg Asp Leu Arg Glu Lys Ala Tyr Glu Thr Gln Val Val
                160                 165                 170

gac cct ttc agg tac ctg ttt atg gag aaa cca aag ttt gac ggc gcc      2081
Asp Pro Phe Arg Tyr Leu Phe Met Glu Lys Pro Lys Phe Asp Gly Ala
            175                 180                 185

gaa ttg tac ttg cca gat atc gac gtc atc atc att gga tca ggc gcc      2129
Glu Leu Tyr Leu Pro Asp Ile Asp Val Ile Ile Ile Gly Ser Gly Ala
        190                 195                 200

ggt gct ggt gtc atg gcc cac act ctc gcc aac gac ggg ttc aag acc      2177
Gly Ala Gly Val Met Ala His Thr Leu Ala Asn Asp Gly Phe Lys Thr
    205                 210                 215

ttg gtt ttg gaa aag gga aag tat ttc agc aac tcc gag ttg aac ttt      2225
Leu Val Leu Glu Lys Gly Lys Tyr Phe Ser Asn Ser Glu Leu Asn Phe
220                 225                 230                 235

aat gac gct gat ggc gtg aaa gag ttg tac caa ggt aaa ggt gct ttg      2273
Asn Asp Ala Asp Gly Val Lys Glu Leu Tyr Gln Gly Lys Gly Ala Leu
                240                 245                 250

gcc acc acc aat cag cag atg ttt att ctt gcc ggt tcc act ttg ggc      2321
Ala Thr Thr Asn Gln Gln Met Phe Ile Leu Ala Gly Ser Thr Leu Gly
            255                 260                 265

ggt ggt acc act gtc aac tgg tct gct tgc ctt aaa aca cca ttt aaa      2369
Gly Gly Thr Thr Val Asn Trp Ser Ala Cys Leu Lys Thr Pro Phe Lys
        270                 275                 280

gtg cgt aag gag tgg tac gac gag ttt ggt ctt gaa ttt gct gcc gat      2417
Val Arg Lys Glu Trp Tyr Asp Glu Phe Gly Leu Glu Phe Ala Ala Asp
    285                 290                 295

gaa gcc tac gac aaa gcg cag gat tat gtt tgg aaa caa atg ggt gct      2465
Glu Ala Tyr Asp Lys Ala Gln Asp Tyr Val Trp Lys Gln Met Gly Ala
300                 305                 310                 315

tca aca gat gga atc act cac tcc ttg gcc aac gaa gtt gtg gtt gaa      2513
Ser Thr Asp Gly Ile Thr His Ser Leu Ala Asn Glu Val Val Val Glu
                320                 325                 330

gga ggt aag aag ttg ggc tac aag agc aag gaa att gag cag aac aac      2561
Gly Gly Lys Lys Leu Gly Tyr Lys Ser Lys Glu Ile Glu Gln Asn Asn
            335                 340                 345

ggt ggc cac cct gac cac cca tgt ggt ttc tgt tac ttg ggc tgt aag      2609
Gly Gly His Pro Asp His Pro Cys Gly Phe Cys Tyr Leu Gly Cys Lys
        350                 355                 360

tac ggt att aaa cag ggt tct gtg aat aac tgg ttt aga gac gca gct      2657
Tyr Gly Ile Lys Gln Gly Ser Val Asn Asn Trp Phe Arg Asp Ala Ala
    365                 370                 375
```

-continued

```
gcc cac ggg tcc aag ttc atg caa caa gtc aga gtt gtg caa atc ctc     2705
Ala His Gly Ser Lys Phe Met Gln Gln Val Arg Val Val Gln Ile Leu
380                 385                 390                 395

aac aag aat ggc gtc gct tat ggt atc ttg tgt gag gat gtc gaa acc     2753
Asn Lys Asn Gly Val Ala Tyr Gly Ile Leu Cys Glu Asp Val Glu Thr
                400                 405                 410

gga gtc agg ttc act att agt ggc ccc aaa aag ttt gtt gtt tct gct     2801
Gly Val Arg Phe Thr Ile Ser Gly Pro Lys Lys Phe Val Val Ser Ala
            415                 420                 425

ggt tct ttg aac acg cca act gtg ttg acc aac tcc gga ttc aag aac     2849
Gly Ser Leu Asn Thr Pro Thr Val Leu Thr Asn Ser Gly Phe Lys Asn
        430                 435                 440

aag cac att ggt aag aac ttg acg ttg cac cca gtt tcc acc gtg ttt     2897
Lys His Ile Gly Lys Asn Leu Thr Leu His Pro Val Ser Thr Val Phe
    445                 450                 455

ggt gac ttt ggc aga gac gtg caa gcc gac cat ttc cac aaa tct att     2945
Gly Asp Phe Gly Arg Asp Val Gln Ala Asp His Phe His Lys Ser Ile
460                 465                 470                 475

atg act tcg ctt tgt tac gag gtt gct gac ttg gac ggc aag ggc cac     2993
Met Thr Ser Leu Cys Tyr Glu Val Ala Asp Leu Asp Gly Lys Gly His
                480                 485                 490

gga tgc aga atc gaa acc atc ttg aac gct cca ttc atc caa gct tct     3041
Gly Cys Arg Ile Glu Thr Ile Leu Asn Ala Pro Phe Ile Gln Ala Ser
            495                 500                 505

ttg ttg cca tgg aga gga agt gac gag gtc aga aga gac ttg ttg cgt     3089
Leu Leu Pro Trp Arg Gly Ser Asp Glu Val Arg Arg Asp Leu Leu Arg
        510                 515                 520

tac aac aac atg gtg gcc atg ttg ctt atc acg cgt gat acc acc agt     3137
Tyr Asn Asn Met Val Ala Met Leu Leu Ile Thr Arg Asp Thr Thr Ser
    525                 530                 535

ggt tca gtt tct gct gac cca aag aag ccc gac gct ttg att gtc gac     3185
Gly Ser Val Ser Ala Asp Pro Lys Lys Pro Asp Ala Leu Ile Val Asp
540                 545                 550                 555

tat gag att aac aag ttt gac aag aat gcc atc ttg caa gct ttc ttg     3233
Tyr Glu Ile Asn Lys Phe Asp Lys Asn Ala Ile Leu Gln Ala Phe Leu
                560                 565                 570

atc act tcc gac atg ttg tac att gaa ggt gcc aag aga atc ctc agt     3281
Ile Thr Ser Asp Met Leu Tyr Ile Glu Gly Ala Lys Arg Ile Leu Ser
            575                 580                 585

cca cag cca tgg gtg cca atc ttt gag tcg aac aag cca aag gag caa     3329
Pro Gln Pro Trp Val Pro Ile Phe Glu Ser Asn Lys Pro Lys Glu Gln
        590                 595                 600

aga acg atc aag gac aag gac tat gtt gag tgg aga gcc aag gct gct     3377
Arg Thr Ile Lys Asp Lys Asp Tyr Val Glu Trp Arg Ala Lys Ala Ala
    605                 610                 615

aag ata cct ttc gac acc tac ggt tct gca tat ggg tcc gca cat caa     3425
Lys Ile Pro Phe Asp Thr Tyr Gly Ser Ala Tyr Gly Ser Ala His Gln
620                 625                 630                 635

atg tcc acc tgt cgt atg tcc gga aag ggt cct aaa tac ggt gct gtt     3473
Met Ser Thr Cys Arg Met Ser Gly Lys Gly Pro Lys Tyr Gly Ala Val
                640                 645                 650

gat act gat ggt aga ttg ttt gaa tgt tcg aat gtc tat gtt gct gat     3521
Asp Thr Asp Gly Arg Leu Phe Glu Cys Ser Asn Val Tyr Val Ala Asp
            655                 660                 665

gct agt gtt ttg cct act gcc agc ggt gcc aac cca atg ata tcc acc     3569
Ala Ser Val Leu Pro Thr Ala Ser Gly Ala Asn Pro Met Ile Ser Thr
        670                 675                 680

atg acc ttt gct aga cag att gcg tta ggt ttg gct gac tcc ttg aag     3617
Met Thr Phe Ala Arg Gln Ile Ala Leu Gly Leu Ala Asp Ser Leu Lys
```

-continued

```
    685                 690                 695

acc aaa ccc aag ttg tagagagacg gaaatacgac acttatatac tagatgtatc     3672
Thr Lys Pro Lys Leu
700

ttacaattta tattctcgat gatggctttt actatctcct atgttacact ataatgacat   3732

caccacaacc tctactactg tctccagtat cctccttgct gttgaccgta cccaccagcc   3792

tgttgattga accctgtgaa ctgtggttgc tgttgagcgt accccacgtt agtgaactgc   3852

ggttgttggg caaactgctg tacgggctgt tgctgctgct gctgttgttg ttgttgttgt   3912

tgtcccgtgg gctggttgta caacgacatg atgttctgct tgtttgtctg ttgggcaacc   3972

aactgtgggt tattcatctg catcaactgc tgctggtgtt gagggttgtt tggatccaag   4032

tactcttgcc cgttggcgtc gatataagaa atctgccccg tgactgggtc agtgtactgg   4092

tatatctgtg gcatgccacc agcttgtgca ggcatgccgg ttgccaatgg cacctgtgct   4152

tgcgtc                                                              4158


<210> SEQ ID NO 4
<211> LENGTH: 704
<212> TYPE: PRT
<213> ORGANISM: Candida tropicalis

<400> SEQUENCE: 4

Met Asn Thr Phe Leu Pro Asp Val Leu Glu Tyr Lys His Val Asp Thr
1               5                   10                  15

Leu Leu Leu Leu Cys Asp Gly Ile Ile His Glu Thr Thr Val Asp Gln
            20                  25                  30

Ile Lys Asp Ala Ile Ala Pro Asp Phe Pro Glu Asp Gln Tyr Glu Glu
        35                  40                  45

Tyr Leu Lys Thr Phe Thr Lys Pro Ser Glu Thr Pro Gly Phe Arg Glu
    50                  55                  60

Ala Val Tyr Asp Thr Ile Asn Ala Thr Pro Thr Asp Ala Val His Met
65                  70                  75                  80

Cys Ile Val Leu Thr Thr Ala Leu Asp Ser Arg Ile Leu Ala Pro Thr
                85                  90                  95

Leu Thr Asn Ser Leu Thr Pro Ile Lys Asp Met Thr Leu Lys Glu Arg
            100                 105                 110

Glu Gln Leu Leu Ala Ser Trp Arg Asp Ser Pro Ile Ala Ala Lys Arg
        115                 120                 125

Arg Leu Phe Arg Leu Ile Ser Ser Leu Thr Leu Thr Thr Phe Thr Arg
    130                 135                 140

Leu Ala Ser Glu Leu His Leu Lys Ala Ile His Tyr Pro Gly Arg Asp
145                 150                 155                 160

Leu Arg Glu Lys Ala Tyr Glu Thr Gln Val Val Asp Pro Phe Arg Tyr
                165                 170                 175

Leu Phe Met Glu Lys Pro Lys Phe Asp Gly Ala Glu Leu Tyr Leu Pro
            180                 185                 190

Asp Ile Asp Val Ile Ile Ile Gly Ser Gly Ala Gly Ala Gly Val Met
        195                 200                 205

Ala His Thr Leu Ala Asn Asp Gly Phe Lys Thr Leu Val Leu Glu Lys
    210                 215                 220

Gly Lys Tyr Phe Ser Asn Ser Glu Leu Asn Phe Asn Asp Ala Asp Gly
225                 230                 235                 240

Val Lys Glu Leu Tyr Gln Gly Lys Gly Ala Leu Ala Thr Thr Asn Gln
                245                 250                 255
```

-continued

```
Gln Met Phe Ile Leu Ala Gly Ser Thr Leu Gly Gly Gly Thr Thr Val
            260                 265                 270

Asn Trp Ser Ala Cys Leu Lys Thr Pro Phe Lys Val Arg Lys Glu Trp
        275                 280                 285

Tyr Asp Glu Phe Gly Leu Glu Phe Ala Ala Asp Glu Ala Tyr Asp Lys
    290                 295                 300

Ala Gln Asp Tyr Val Trp Lys Gln Met Gly Ala Ser Thr Asp Gly Ile
305                 310                 315                 320

Thr His Ser Leu Ala Asn Glu Val Val Val Glu Gly Gly Lys Lys Leu
                325                 330                 335

Gly Tyr Lys Ser Lys Glu Ile Glu Gln Asn Asn Gly Gly His Pro Asp
            340                 345                 350

His Pro Cys Gly Phe Cys Tyr Leu Gly Cys Lys Tyr Gly Ile Lys Gln
        355                 360                 365

Gly Ser Val Asn Asn Trp Phe Arg Asp Ala Ala Ala His Gly Ser Lys
    370                 375                 380

Phe Met Gln Gln Val Arg Val Val Gln Ile Leu Asn Lys Asn Gly Val
385                 390                 395                 400

Ala Tyr Gly Ile Leu Cys Glu Asp Val Glu Thr Gly Val Arg Phe Thr
                405                 410                 415

Ile Ser Gly Pro Lys Lys Phe Val Val Ser Ala Gly Ser Leu Asn Thr
            420                 425                 430

Pro Thr Val Leu Thr Asn Ser Gly Phe Lys Asn Lys His Ile Gly Lys
        435                 440                 445

Asn Leu Thr Leu His Pro Val Ser Thr Val Phe Gly Asp Phe Gly Arg
    450                 455                 460

Asp Val Gln Ala Asp His Phe His Lys Ser Ile Met Thr Ser Leu Cys
465                 470                 475                 480

Tyr Glu Val Ala Asp Leu Asp Gly Lys Gly His Gly Cys Arg Ile Glu
                485                 490                 495

Thr Ile Leu Asn Ala Pro Phe Ile Gln Ala Ser Leu Leu Pro Trp Arg
            500                 505                 510

Gly Ser Asp Glu Val Arg Arg Asp Leu Leu Arg Tyr Asn Asn Met Val
        515                 520                 525

Ala Met Leu Leu Ile Thr Arg Asp Thr Thr Ser Gly Ser Val Ser Ala
    530                 535                 540

Asp Pro Lys Lys Pro Asp Ala Leu Ile Val Asp Tyr Glu Ile Asn Lys
545                 550                 555                 560

Phe Asp Lys Asn Ala Ile Leu Gln Ala Phe Leu Ile Thr Ser Asp Met
                565                 570                 575

Leu Tyr Ile Glu Gly Ala Lys Arg Ile Leu Ser Pro Gln Pro Trp Val
            580                 585                 590

Pro Ile Phe Glu Ser Asn Lys Pro Lys Glu Gln Arg Thr Ile Lys Asp
        595                 600                 605

Lys Asp Tyr Val Glu Trp Arg Ala Lys Ala Ala Lys Ile Pro Phe Asp
    610                 615                 620

Thr Tyr Gly Ser Ala Tyr Gly Ser Ala His Gln Met Ser Thr Cys Arg
625                 630                 635                 640

Met Ser Gly Lys Gly Pro Lys Tyr Gly Ala Val Asp Thr Asp Gly Arg
                645                 650                 655

Leu Phe Glu Cys Ser Asn Val Tyr Val Ala Asp Ala Ser Val Leu Pro
            660                 665                 670
```

-continued

Thr Ala Ser Gly Ala Asn Pro Met Ile Ser Thr Met Thr Phe Ala Arg
        675                 680                 685

Gln Ile Ala Leu Gly Leu Ala Asp Ser Leu Lys Thr Lys Pro Lys Leu
    690                 695                 700

<210> SEQ ID NO 5
<211> LENGTH: 3753
<212> TYPE: DNA
<213> ORGANISM: Candida tropicalis
<220> FEATURE:
<221> NAME/KEY: CDS
<222> LOCATION: (1099)..(3213)

<400> SEQUENCE: 5
tgttgataga gcttagactt gtgttttgta tttgtaatct gacgttgatc gtttgatatt      60
ttcctgtgat atcacgtaaa ttcggcaacc aactttttac tttttgcaac actttctctt     120
caccactctc agaaccaatg ccaccgaaga agggtctcag ccaggaggaa aagctctcgg     180
cactcctcac ctggttccaa gccagtcatt gcttctacac actcaaggag gttgaacaga     240
aggcgagcaa agcgtgcaag atctcgtcta tgcagatcaa ggacttggtt gcaagcttag     300
tcaacgaagg tttggtagaa caggaaaagt gtgggaccac aaacttgtac tggtcgttcc     360
agtactcgga attcaaacgg aagctacaga gatacgggca gctaagacaa tcagccgcca     420
aacttcaagc ggataaaggc aagttggcgg aagagttgcg aaacgcatgt ggtgaacggg     480
acatggacaa caataggcaa gaccggatgc aacaatacga tcaccttgtt aacgaggcgg     540
cacgtctcca ggaggaacta aaactgtcaa ggcagataga taccattgac gagttagttc     600
aggccattga tttcttcaac gagctgatag agaccgtcct cagctacatc agccatcagt     660
cagggaccag cgtgtcgata ttgaaaacgg agtttgagat acccgcagaa ctagaagagg     720
ccccccagat aagcaatgcc ggagttagtg cgtaaatcga gcaggcatac attgcccctt     780
tgtatttttt cacaggatgc tcaccccacc acgcccaaca tttcccccca cattttatta     840
cccacattga gccgtcaaat gcattttttt atccgtcgct agctaaacca aaattccaca     900
tgcgttgcct cagagtatat aaacaacggg gcaaaaaaca tgggattaat agcttatttg     960
tggattgata tttttatatt ttagttcgcc ccttctacga ccaagctcaa ttggactatt    1020
tgtcagtggt gtataagcta gagattacta gactgctttt ctgattcttg atcatcccct    1080
tagttccagt gcctagag atg aat acc ttc ttg cca gac gtg ctc gaa tac      1131
                    Met Asn Thr Phe Leu Pro Asp Val Leu Glu Tyr
                    1               5                   10 aaa cac gtc gat acc ctt ttg tta tta tgt gac ggg atc atc cac gaa      1179
Lys His Val Asp Thr Leu Leu Leu Leu Cys Asp Gly Ile Ile His Glu
            15                  20                  25 acc aca gtc gac cag atc agg gac gcc att gct ccc gac ttc cct gaa      1227
Thr Thr Val Asp Gln Ile Arg Asp Ala Ile Ala Pro Asp Phe Pro Glu
        30                  35                  40 gac cag tac gag gag tat ctc aag acc ttc acc aag cca tct gag acc      1275
Asp Gln Tyr Glu Glu Tyr Leu Lys Thr Phe Thr Lys Pro Ser Glu Thr
    45                  50                  55 cct ggg ttc aga gaa gcc gtc tac gac acg atc aac agc acc cca acc      1323
Pro Gly Phe Arg Glu Ala Val Tyr Asp Thr Ile Asn Ser Thr Pro Thr
60                  65                  70                  75 gag gct gtg cac atg tgt att gta ttg acc acc gca ttg gac tcg aga      1371
Glu Ala Val His Met Cys Ile Val Leu Thr Thr Ala Leu Asp Ser Arg
                80                  85                  90 atc ttg gcc ccc acg ttg acc aac tcg ttg acg cct atc aag gat atg      1419
Ile Leu Ala Pro Thr Leu Thr Asn Ser Leu Thr Pro Ile Lys Asp Met -continued

```
            95                  100                 105

acc ttg aaa gag cgt gaa caa ttg ttg gct gcc tgg cgt gat tcc ccg     1467
Thr Leu Lys Glu Arg Glu Gln Leu Leu Ala Ala Trp Arg Asp Ser Pro
        110                 115                 120

atc gcg gcc aag aga aga ttg ttc aga ttg att tcc tca ctt acc ttg     1515
Ile Ala Ala Lys Arg Arg Leu Phe Arg Leu Ile Ser Ser Leu Thr Leu
    125                 130                 135

acg acc ttt acg aga ttg gcc agc gac ttg cac ttg aga gcc atc cac     1563
Thr Thr Phe Thr Arg Leu Ala Ser Asp Leu His Leu Arg Ala Ile His
140                 145                 150                 155

tac cct ggc aga gac ttg cgt gaa aag gca tat gaa acc cag gtg gtt     1611
Tyr Pro Gly Arg Asp Leu Arg Glu Lys Ala Tyr Glu Thr Gln Val Val
                160                 165                 170

gac cct ttc agg tac ctg ttt atg gaa aaa cca aag ttt gac ggc acc     1659
Asp Pro Phe Arg Tyr Leu Phe Met Glu Lys Pro Lys Phe Asp Gly Thr
            175                 180                 185

gag ttg tac ttg cca gat atc gac gtc atc atc att gga tcc ggt gcc     1707
Glu Leu Tyr Leu Pro Asp Ile Asp Val Ile Ile Ile Gly Ser Gly Ala
        190                 195                 200

ggt gct ggt gtc atg gcc cac act tta gcc aac gac ggg tac aag acc     1755
Gly Ala Gly Val Met Ala His Thr Leu Ala Asn Asp Gly Tyr Lys Thr
    205                 210                 215

ttg gtt ttg gaa aag gga aag tat ttc agc aac tcc gag ttg aac ttt     1803
Leu Val Leu Glu Lys Gly Lys Tyr Phe Ser Asn Ser Glu Leu Asn Phe
220                 225                 230                 235

aat gat gcc gat ggt atg aaa gag ttg tac caa ggt aaa tgt gcg ttg     1851
Asn Asp Ala Asp Gly Met Lys Glu Leu Tyr Gln Gly Lys Cys Ala Leu
                240                 245                 250

acc acc acg aac cag cag atg ttt att ctt gcc ggt tcc act ttg ggc     1899
Thr Thr Thr Asn Gln Gln Met Phe Ile Leu Ala Gly Ser Thr Leu Gly
            255                 260                 265

ggt ggt acc act gtt aac tgg tct gct tgt ctt aaa aca cca ttt aaa     1947
Gly Gly Thr Thr Val Asn Trp Ser Ala Cys Leu Lys Thr Pro Phe Lys
        270                 275                 280

gtg cgt aag gag tgg tac gac gag ttt ggt ctt gaa ttt gct gcc gac     1995
Val Arg Lys Glu Trp Tyr Asp Glu Phe Gly Leu Glu Phe Ala Ala Asp
    285                 290                 295

gaa gcc tac gac aaa gca caa gac tat gtt tgg aaa caa atg ggc gct     2043
Glu Ala Tyr Asp Lys Ala Gln Asp Tyr Val Trp Lys Gln Met Gly Ala
300                 305                 310                 315

tct acc gaa gga atc act cac tct ttg gcg aac gcg gtt gtg gtt gaa     2091
Ser Thr Glu Gly Ile Thr His Ser Leu Ala Asn Ala Val Val Val Glu
                320                 325                 330

gga ggt aag aag ttg ggt tac aag agc aag gaa atc gag cag aac aat     2139
Gly Gly Lys Lys Leu Gly Tyr Lys Ser Lys Glu Ile Glu Gln Asn Asn
            335                 340                 345

ggt ggc cat cct gac cac ccc tgt ggt ttc tgt tac ttg ggc tgt aag     2187
Gly Gly His Pro Asp His Pro Cys Gly Phe Cys Tyr Leu Gly Cys Lys
        350                 355                 360

tac ggt att aag cag ggt tct gtg aat aac tgg ttt aga gac gca gct     2235
Tyr Gly Ile Lys Gln Gly Ser Val Asn Asn Trp Phe Arg Asp Ala Ala
    365                 370                 375

gcc cac ggg tcc aag ttc atg caa caa gtc aga gtt gtg caa atc ctc     2283
Ala His Gly Ser Lys Phe Met Gln Gln Val Arg Val Val Gln Ile Leu
380                 385                 390                 395

cac aat aaa ggc gtc gct tat ggc atc ttg tgt gag gat gtc gag acc     2331
His Asn Lys Gly Val Ala Tyr Gly Ile Leu Cys Glu Asp Val Glu Thr
                400                 405                 410

gga gtc aaa ttc act atc agt ggc ccc aaa aag ttt gtt gtt tct gca     2379
```

-continued

```
Gly Val Lys Phe Thr Ile Ser Gly Pro Lys Lys Phe Val Val Ser Ala
            415                 420                 425

ggt tct ttg aac acg cca acg gtg ttg acc aac tcc gga ttc aag aac     2427
Gly Ser Leu Asn Thr Pro Thr Val Leu Thr Asn Ser Gly Phe Lys Asn
        430                 435                 440

aaa cac atc ggt aag aac ttg acg ttg cac cca gtt tcg acc gtg ttt     2475
Lys His Ile Gly Lys Asn Leu Thr Leu His Pro Val Ser Thr Val Phe
    445                 450                 455

ggt gac ttt ggc aga gac gtg caa gcc gac cat ttc cac aaa tct att     2523
Gly Asp Phe Gly Arg Asp Val Gln Ala Asp His Phe His Lys Ser Ile
460                 465                 470                 475

atg act tcg ctc tgt tac gaa gtc gct gac ttg gac ggc aag ggc cac     2571
Met Thr Ser Leu Cys Tyr Glu Val Ala Asp Leu Asp Gly Lys Gly His
                480                 485                 490

gga tgc aga atc gag acc atc ttg aac gct cca ttc atc caa gct tct     2619
Gly Cys Arg Ile Glu Thr Ile Leu Asn Ala Pro Phe Ile Gln Ala Ser
            495                 500                 505

ttg ttg cca tgg aga gga agc gac gag gtc aga aga gac ttg ttg cgt     2667
Leu Leu Pro Trp Arg Gly Ser Asp Glu Val Arg Arg Asp Leu Leu Arg
        510                 515                 520

tac aac aac atg gtg gcc atg ttg ctt atc acc cgt gac acc acc agt     2715
Tyr Asn Asn Met Val Ala Met Leu Leu Ile Thr Arg Asp Thr Thr Ser
    525                 530                 535

ggt tca gtt tct gct gac cca aag aag ccc gac gct ttg att gtc gac     2763
Gly Ser Val Ser Ala Asp Pro Lys Lys Pro Asp Ala Leu Ile Val Asp
540                 545                 550                 555

tat gac atc aac aag ttt gac aag aat gcc atc ttg caa gct ttc ttg     2811
Tyr Asp Ile Asn Lys Phe Asp Lys Asn Ala Ile Leu Gln Ala Phe Leu
                560                 565                 570

atc acc tcc gac atg ttg tac atc gaa ggt gcc aag aga atc ctc agt     2859
Ile Thr Ser Asp Met Leu Tyr Ile Glu Gly Ala Lys Arg Ile Leu Ser
            575                 580                 585

cca cag gca tgg gtg cca atc ttt gag tcg aac aag cca aag gag caa     2907
Pro Gln Ala Trp Val Pro Ile Phe Glu Ser Asn Lys Pro Lys Glu Gln
        590                 595                 600

aga aca atc aag gac aag gac tat gtc gaa tgg aga gcc aag gct gcc     2955
Arg Thr Ile Lys Asp Lys Asp Tyr Val Glu Trp Arg Ala Lys Ala Ala
    605                 610                 615

aag ata cct ttc gac acc tac ggt tct gcc tat ggg tcc gca cat caa     3003
Lys Ile Pro Phe Asp Thr Tyr Gly Ser Ala Tyr Gly Ser Ala His Gln
620                 625                 630                 635

atg tcc acc tgt cgt atg tcc gga aag ggt cct aaa tac ggc gcc gtt     3051
Met Ser Thr Cys Arg Met Ser Gly Lys Gly Pro Lys Tyr Gly Ala Val
                640                 645                 650

gat acc gat ggt aga ttg ttt gaa tgt tcg aat gtc tat gtt gct gat     3099
Asp Thr Asp Gly Arg Leu Phe Glu Cys Ser Asn Val Tyr Val Ala Asp
            655                 660                 665

gct agt gtt ttg cct act gcc agc ggt gcc aac cca atg atc tcc acc     3147
Ala Ser Val Leu Pro Thr Ala Ser Gly Ala Asn Pro Met Ile Ser Thr
        670                 675                 680

atg acg ttt gct aga cag att gcg tta ggt ttg gct gac tct ttg aag     3195
Met Thr Phe Ala Arg Gln Ile Ala Leu Gly Leu Ala Asp Ser Leu Lys
    685                 690                 695

acc aaa ccc aag ttg tag agagagacag aaatacgaca cttatatact            3243
Thr Lys Pro Lys Leu
700

agatgtatct tacaatttat attttcgatg atggctttta ctatctccta tgttacacta   3303

taatgacatc accacatctt ctactactgt ctccagtatc ctccttgctg ttgaccgtat   3363
```

-continued

```
ccaccagcct gttggttgaa ccccgtgaac tgtggttgct gttgagcgta ccccacgtta   3423

gtgaactgcg gttgttgggt aaactgctgt acgggctgtt gttgctgttg ctgttgttgc   3483

tgttgttgct gttgttgctg ttgttgctgt tgttgttgtt gtcccgttgg ctggttgtac   3543

aacgacatga tgttctgctt gtttgtctgc tgggcaacca actgtgggtt attcatctgc   3603

atcaactgct gctggtgctg agggttgttt ggatccaagt actcctgccc gttggcgtcg   3663

atataagaaa tctgccccgt gactgggtca gtgtactggt atatctgtgg catgccaccc   3723

gcttgtgcag gcatgccggt tgccaatggc                                     3753
```

<210> SEQ ID NO 6
<211> LENGTH: 704
<212> TYPE: PRT
<213> ORGANISM: Candida tropicalis

<400> SEQUENCE: 6

```
Met Asn Thr Phe Leu Pro Asp Val Leu Glu Tyr Lys His Val Asp Thr
1               5                   10                  15

Leu Leu Leu Leu Cys Asp Gly Ile Ile His Glu Thr Thr Val Asp Gln
            20                  25                  30

Ile Arg Asp Ala Ile Ala Pro Asp Phe Pro Glu Asp Gln Tyr Glu Glu
        35                  40                  45

Tyr Leu Lys Thr Phe Thr Lys Pro Ser Glu Thr Pro Gly Phe Arg Glu
    50                  55                  60

Ala Val Tyr Asp Thr Ile Asn Ser Thr Pro Thr Glu Ala Val His Met
65                  70                  75                  80

Cys Ile Val Leu Thr Thr Ala Leu Asp Ser Arg Ile Leu Ala Pro Thr
                85                  90                  95

Leu Thr Asn Ser Leu Thr Pro Ile Lys Asp Met Thr Leu Lys Glu Arg
            100                 105                 110

Glu Gln Leu Leu Ala Ala Trp Arg Asp Ser Pro Ile Ala Ala Lys Arg
        115                 120                 125

Arg Leu Phe Arg Leu Ile Ser Ser Leu Thr Leu Thr Thr Phe Thr Arg
    130                 135                 140

Leu Ala Ser Asp Leu His Leu Arg Ala Ile His Tyr Pro Gly Arg Asp
145                 150                 155                 160

Leu Arg Glu Lys Ala Tyr Glu Thr Gln Val Val Asp Pro Phe Arg Tyr
                165                 170                 175

Leu Phe Met Glu Lys Pro Lys Phe Asp Gly Thr Glu Leu Tyr Leu Pro
            180                 185                 190

Asp Ile Asp Val Ile Ile Ile Gly Ser Gly Ala Gly Ala Gly Val Met
        195                 200                 205

Ala His Thr Leu Ala Asn Asp Gly Tyr Lys Thr Leu Val Leu Glu Lys
    210                 215                 220

Gly Lys Tyr Phe Ser Asn Ser Glu Leu Asn Phe Asn Asp Ala Asp Gly
225                 230                 235                 240

Met Lys Glu Leu Tyr Gln Gly Lys Cys Ala Leu Thr Thr Thr Asn Gln
                245                 250                 255

Gln Met Phe Ile Leu Ala Gly Ser Thr Leu Gly Gly Gly Thr Thr Val
            260                 265                 270

Asn Trp Ser Ala Cys Leu Lys Thr Pro Phe Lys Val Arg Lys Glu Trp
        275                 280                 285

Tyr Asp Glu Phe Gly Leu Glu Phe Ala Ala Asp Glu Ala Tyr Asp Lys
    290                 295                 300
```

-continued

```
Ala Gln Asp Tyr Val Trp Lys Gln Met Gly Ala Ser Thr Glu Gly Ile
305                 310                 315                 320

Thr His Ser Leu Ala Asn Ala Val Val Val Glu Gly Gly Lys Lys Leu
                325                 330                 335

Gly Tyr Lys Ser Lys Glu Ile Glu Gln Asn Asn Gly Gly His Pro Asp
            340                 345                 350

His Pro Cys Gly Phe Cys Tyr Leu Gly Cys Lys Tyr Gly Ile Lys Gln
        355                 360                 365

Gly Ser Val Asn Asn Trp Phe Arg Asp Ala Ala Ala His Gly Ser Lys
    370                 375                 380

Phe Met Gln Gln Val Arg Val Val Gln Ile Leu His Asn Lys Gly Val
385                 390                 395                 400

Ala Tyr Gly Ile Leu Cys Glu Asp Val Glu Thr Gly Val Lys Phe Thr
                405                 410                 415

Ile Ser Gly Pro Lys Lys Phe Val Val Ser Ala Gly Ser Leu Asn Thr
            420                 425                 430

Pro Thr Val Leu Thr Asn Ser Gly Phe Lys Asn Lys His Ile Gly Lys
        435                 440                 445

Asn Leu Thr Leu His Pro Val Ser Thr Val Phe Gly Asp Phe Gly Arg
    450                 455                 460

Asp Val Gln Ala Asp His Phe His Lys Ser Ile Met Thr Ser Leu Cys
465                 470                 475                 480

Tyr Glu Val Ala Asp Leu Asp Gly Lys Gly His Gly Cys Arg Ile Glu
                485                 490                 495

Thr Ile Leu Asn Ala Pro Phe Ile Gln Ala Ser Leu Leu Pro Trp Arg
            500                 505                 510

Gly Ser Asp Glu Val Arg Arg Asp Leu Leu Arg Tyr Asn Asn Met Val
        515                 520                 525

Ala Met Leu Leu Ile Thr Arg Asp Thr Thr Ser Gly Ser Val Ser Ala
    530                 535                 540

Asp Pro Lys Lys Pro Asp Ala Leu Ile Val Asp Tyr Asp Ile Asn Lys
545                 550                 555                 560

Phe Asp Lys Asn Ala Ile Leu Gln Ala Phe Leu Ile Thr Ser Asp Met
                565                 570                 575

Leu Tyr Ile Glu Gly Ala Lys Arg Ile Leu Ser Pro Gln Ala Trp Val
            580                 585                 590

Pro Ile Phe Glu Ser Asn Lys Pro Lys Glu Gln Arg Thr Ile Lys Asp
        595                 600                 605

Lys Asp Tyr Val Glu Trp Arg Ala Lys Ala Ala Lys Ile Pro Phe Asp
    610                 615                 620

Thr Tyr Gly Ser Ala Tyr Gly Ser Ala His Gln Met Ser Thr Cys Arg
625                 630                 635                 640

Met Ser Gly Lys Gly Pro Lys Tyr Gly Ala Val Asp Thr Asp Gly Arg
                645                 650                 655

Leu Phe Glu Cys Ser Asn Val Tyr Val Ala Asp Ala Ser Val Leu Pro
            660                 665                 670

Thr Ala Ser Gly Ala Asn Pro Met Ile Ser Thr Met Thr Phe Ala Arg
        675                 680                 685

Gln Ile Ala Leu Gly Leu Ala Asp Ser Leu Lys Thr Lys Pro Lys Leu
    690                 695                 700
```

<210> SEQ ID NO 7
<211> LENGTH: 3545
<212> TYPE: DNA

-continued

```
<213> ORGANISM: Candida tropicalis
<220> FEATURE:
<221> NAME/KEY: CDS
<222> LOCATION: (1179)..(3290)

<400> SEQUENCE: 7

ccttaattaa agtctccaag ttgaccgacg cccaagtcat gtaccacttt atttccggtt     60

acacttccaa gatggctggt actgaagaag gtgtcacgga accacaagct actttctccg    120

cttgtttcgg tcaaccattc ttggtgttgc acccaatgaa gtacgctcaa caattgtctg    180

acaagatctc gcaacacaag gctaacgcct ggttgttgaa caccggttgg gttggttctt    240

ctgctgctag aggtggtaag agatgctcat tgaagtacac cagagccatt ttggacgcta    300

tccactctgg tgaattgtcc aaggttgaat acgaaacttt cccagtcttc aacttgaatg    360

tcccaacctc ctgtccaggt gtcccaagtg aaatcttgaa cccaaccaag gcctggaccg    420

gaaggtgttg actccttcaa caaggaaatc aagtctttgg ctggtaagtt tgctgaaaac    480

ttcaagacct atgctgacca agctaccgct gaagtgagag ctgcaggtcc agaagcttaa    540

agatatttat tcattattta gtttgcctat ttatttctca ttacccatca tcattcaaca    600

ctatatataa agttacttcg gatatcattg taatcgtgcg tgtcgcaatt ggatgatttg    660

gaactgcgct tgaaacggat tcatgcacga agcggagata aaagattacg taatttatct    720

cctgagacaa ttttagccgt gttcacacgc ccttctttgt tctgagcgaa ggataaataa    780

ttagacttcc acagctcatt ctaatttccg tcacgcgaat attgaagggg ggtacatgtg    840

gccgctgaat gtgggggcag taaacgcagt ctctcctctc ccaggaatag tgcaacggag    900

gaaggataac ggatagaaag cggaatgcga ggaaaatttt gaacgcgcaa gaaaagcaat    960

atccgggcta ccaggttttg agccagggaa cacactccta tttctgctca atgactgaac   1020

atagaaaaaa caccaagacg caatgaaacg cacatggaca tttagacctc cccacatgtg   1080

atagtttgtc ttaacagaaa agtataataa gaacccatgc cgtccctttt ctttcgccgc   1140

ttcaactttt ttttttttat cttacacaca tcacgacc atg gct cca ttt ttg ccc   1196
                                          Met Ala Pro Phe Leu Pro
                                          1               5

gac cag gtc gac tac aaa cac gtc gac acc ctt atg tta tta tgt gac     1244
Asp Gln Val Asp Tyr Lys His Val Asp Thr Leu Met Leu Leu Cys Asp
            10                  15                  20

ggg atc atc cac gaa acc acc gtg gac gaa atc aaa gac gtc att gcc     1292
Gly Ile Ile His Glu Thr Thr Val Asp Glu Ile Lys Asp Val Ile Ala
        25                  30                  35

cct gac ttc ccc gcc gac aaa tac gag gag tac gtc agg aca ttc acc     1340
Pro Asp Phe Pro Ala Asp Lys Tyr Glu Glu Tyr Val Arg Thr Phe Thr
    40                  45                  50

aaa ccc tcc gaa acc cca ggg ttc agg gaa acc gtc tac aac acc gtc     1388
Lys Pro Ser Glu Thr Pro Gly Phe Arg Glu Thr Val Tyr Asn Thr Val
55                  60                  65                  70

aac gca aac acc atg gat gca atc cac cag ttc att atc ttg acc aat     1436
Asn Ala Asn Thr Met Asp Ala Ile His Gln Phe Ile Ile Leu Thr Asn
                75                  80                  85

gtt ttg gga tca agg gtc ttg gca cca gct ttg acc aac tcg ttg act     1484
Val Leu Gly Ser Arg Val Leu Ala Pro Ala Leu Thr Asn Ser Leu Thr
            90                  95                  100

cct atc aag gac atg agc ttg gaa gac cgt gaa aag ttg tta gcc tcg     1532
Pro Ile Lys Asp Met Ser Leu Glu Asp Arg Glu Lys Leu Leu Ala Ser
        105                 110                 115

tgg cgt gac tcc cct att gct gct aaa agg aag ttg ttc agg ttg gtt     1580
Trp Arg Asp Ser Pro Ile Ala Ala Lys Arg Lys Leu Phe Arg Leu Val
```

-continued

```
    120                 125                 130

tct acg ctt acc ttg gtc acg ttc acg aga ttg gcc aat gag ttg cat      1628
Ser Thr Leu Thr Leu Val Thr Phe Thr Arg Leu Ala Asn Glu Leu His
135                 140                 145                 150

ttg aaa gcc att cat tat cca gga aga gaa gac cgt gaa aag gct tat      1676
Leu Lys Ala Ile His Tyr Pro Gly Arg Glu Asp Arg Glu Lys Ala Tyr
                155                 160                 165

gaa acc cag gag att gac cct ttt aag tac cag ttt ttg gaa aaa ccg      1724
Glu Thr Gln Glu Ile Asp Pro Phe Lys Tyr Gln Phe Leu Glu Lys Pro
            170                 175                 180

aag ttt tac ggc gct gag ttg tac ttg cca gat att gat gtg atc att      1772
Lys Phe Tyr Gly Ala Glu Leu Tyr Leu Pro Asp Ile Asp Val Ile Ile
        185                 190                 195

att gga tct ggg gcc ggt gct ggt gtc gtg gcc cac act ttg acc aac      1820
Ile Gly Ser Gly Ala Gly Ala Gly Val Val Ala His Thr Leu Thr Asn
    200                 205                 210

gac ggc ttc aag agt ttg gtt ttg gaa aag ggc aga tac ttt agc aac      1868
Asp Gly Phe Lys Ser Leu Val Leu Glu Lys Gly Arg Tyr Phe Ser Asn
215                 220                 225                 230

tcc gag ttg aac ttt gat gac aag gac ggg gtt caa gaa tta tac caa      1916
Ser Glu Leu Asn Phe Asp Asp Lys Asp Gly Val Gln Glu Leu Tyr Gln
                235                 240                 245

agt gga ggt act ttg acc acc gtc aac cag cag ttg ttt gtt ctt gct      1964
Ser Gly Gly Thr Leu Thr Thr Val Asn Gln Gln Leu Phe Val Leu Ala
            250                 255                 260

ggt tcc act ttt ggt ggt ggt acc act gtc aat tgg tcg gcc tgt ctt      2012
Gly Ser Thr Phe Gly Gly Gly Thr Thr Val Asn Trp Ser Ala Cys Leu
        265                 270                 275

aaa acg cca ttc aag gtg cgt aag gaa tgg tat gat gag ttt ggc gtt      2060
Lys Thr Pro Phe Lys Val Arg Lys Glu Trp Tyr Asp Glu Phe Gly Val
    280                 285                 290

gac ttt gct gcc gat gaa gcc tac gac aaa gca cag gat tat gtt tgg      2108
Asp Phe Ala Ala Asp Glu Ala Tyr Asp Lys Ala Gln Asp Tyr Val Trp
295                 300                 305                 310

cag caa atg gga gct tct acc gaa ggc atc acc cac tct ttg gct aac      2156
Gln Gln Met Gly Ala Ser Thr Glu Gly Ile Thr His Ser Leu Ala Asn
                315                 320                 325

gag att att att gaa ggt ggc aag aaa tta ggt tac aag gcc aag gta      2204
Glu Ile Ile Ile Glu Gly Gly Lys Lys Leu Gly Tyr Lys Ala Lys Val
            330                 335                 340

tta gac caa aac agc ggt ggt cat cct cat cac aga tgc ggt ttc tgt      2252
Leu Asp Gln Asn Ser Gly Gly His Pro His His Arg Cys Gly Phe Cys
        345                 350                 355

tat ttg ggt tgt aag cac ggt atc aag cag ggc tct gtt aat aac tgg      2300
Tyr Leu Gly Cys Lys His Gly Ile Lys Gln Gly Ser Val Asn Asn Trp
    360                 365                 370

ttt aga gac gca gct gcc cac ggt tct cag ttc atg caa cag gtt aga      2348
Phe Arg Asp Ala Ala Ala His Gly Ser Gln Phe Met Gln Gln Val Arg
375                 380                 385                 390

gtt ttg caa atc ctt aac aag aag ggc atc gct tat ggt atc ttg tgt      2396
Val Leu Gln Ile Leu Asn Lys Lys Gly Ile Ala Tyr Gly Ile Leu Cys
                395                 400                 405

gag gat gtt gta acc ggt gcc aag ttc acc att act ggc ccc aaa aag      2444
Glu Asp Val Val Thr Gly Ala Lys Phe Thr Ile Thr Gly Pro Lys Lys
            410                 415                 420

ttt gtt gtt gcc gcc ggc gcc tta aac act cca tct gtg ttg gtc aac      2492
Phe Val Val Ala Ala Gly Ala Leu Asn Thr Pro Ser Val Leu Val Asn
        425                 430                 435

tcc gga ttc aag aac aag aac atc ggt aag aac tta act ttg cat cca      2540
```

-continued

```
Ser Gly Phe Lys Asn Lys Asn Ile Gly Lys Asn Leu Thr Leu His Pro
    440                 445                 450

gtt tct gtc gtg ttt ggt gat ttt ggc aaa gac gtt caa gca gat cac      2588
Val Ser Val Val Phe Gly Asp Phe Gly Lys Asp Val Gln Ala Asp His
455                 460                 465                 470

ttc cac aac tcc atc atg act gct ctt tgt tca gaa gcc gct gat tta      2636
Phe His Asn Ser Ile Met Thr Ala Leu Cys Ser Glu Ala Ala Asp Leu
                475                 480                 485

gac ggc aag ggt cat gga tgc aga att gaa acc atc ttg aac gct cca      2684
Asp Gly Lys Gly His Gly Cys Arg Ile Glu Thr Ile Leu Asn Ala Pro
            490                 495                 500

ttc atc cag gct tca ttc tta cca tgg aga ggt agt aac gag gct aga      2732
Phe Ile Gln Ala Ser Phe Leu Pro Trp Arg Gly Ser Asn Glu Ala Arg
        505                 510                 515

cga gac ttg ttg cgt tac aac aac atg gtg gcc atg tta ctt ctt agt      2780
Arg Asp Leu Leu Arg Tyr Asn Asn Met Val Ala Met Leu Leu Leu Ser
    520                 525                 530

cgt gat acc acc agt ggt tcc gtt tcg tcc cat cca act aaa cct gaa      2828
Arg Asp Thr Thr Ser Gly Ser Val Ser Ser His Pro Thr Lys Pro Glu
535                 540                 545                 550

gca tta gtt gtc gag tac gac gtg aac aag ttt gac aga aac tcc atc      2876
Ala Leu Val Val Glu Tyr Asp Val Asn Lys Phe Asp Arg Asn Ser Ile
                555                 560                 565

ttg cag gca ttg ttg gtc act gct gac ttg ttg tac att caa ggt gcc      2924
Leu Gln Ala Leu Leu Val Thr Ala Asp Leu Leu Tyr Ile Gln Gly Ala
            570                 575                 580

aag aga atc ctt agt ccc caa cca tgg gtg cca att ttt gaa tcc gac      2972
Lys Arg Ile Leu Ser Pro Gln Pro Trp Val Pro Ile Phe Glu Ser Asp
        585                 590                 595

aag cca aag gat aag aga tca atc aag gac gag gac tat gtc gaa tgg      3020
Lys Pro Lys Asp Lys Arg Ser Ile Lys Asp Glu Asp Tyr Val Glu Trp
    600                 605                 610

aga gcc aag gtt gcc aag att cct ttt gac acc tac ggc tcg cct tat      3068
Arg Ala Lys Val Ala Lys Ile Pro Phe Asp Thr Tyr Gly Ser Pro Tyr
615                 620                 625                 630

ggt tcg gcg cat caa atg tct tct tgt cgt atg tca ggt aag ggt cct      3116
Gly Ser Ala His Gln Met Ser Ser Cys Arg Met Ser Gly Lys Gly Pro
                635                 640                 645

aaa tac ggt gct gtt gat acc gat ggt aga ttg ttt gaa tgt tcg aat      3164
Lys Tyr Gly Ala Val Asp Thr Asp Gly Arg Leu Phe Glu Cys Ser Asn
            650                 655                 660

gtt tat gtt gct gac gct agt ctt ttg cca act gct agc ggt gct aat      3212
Val Tyr Val Ala Asp Ala Ser Leu Leu Pro Thr Ala Ser Gly Ala Asn
        665                 670                 675

cct atg gtc acc acc atg act ctt gca aga cat gtt gcg tta ggt ttg      3260
Pro Met Val Thr Thr Met Thr Leu Ala Arg His Val Ala Leu Gly Leu
    680                 685                 690

gca gac tcc ttg aag acc aag gcc aag ttg tagttctgta tacgtatctt        3310
Ala Asp Ser Leu Lys Thr Lys Ala Lys Leu
695                 700

ataatttaga tttcctttta ttgacggtaa acattcagga taggtactac ccttgctgca    3370

aaagcccagc acgccccaat cgcgatgact tgagcgaagc aaacacgcac acaaaagggg    3430

tacacaaaaa ataacgagat gcccttgaag cacacaccca aacacgatgg aacacaagat    3490

ggccctagaa agtacaaaaa aagtaaaggc acttgattcc gcccattaat taagg         3545


<210> SEQ ID NO 8
<211> LENGTH: 704
<212> TYPE: PRT
```

<213> ORGANISM: Candida tropicalis

<400> SEQUENCE: 8

```
Met Ala Pro Phe Leu Pro Asp Gln Val Asp Tyr Lys His Val Asp Thr
1               5                   10                  15

Leu Met Leu Leu Cys Asp Gly Ile Ile His Glu Thr Thr Val Asp Glu
            20                  25                  30

Ile Lys Asp Val Ile Ala Pro Asp Phe Pro Ala Asp Lys Tyr Glu Glu
        35                  40                  45

Tyr Val Arg Thr Phe Thr Lys Pro Ser Glu Thr Pro Gly Phe Arg Glu
    50                  55                  60

Thr Val Tyr Asn Thr Val Asn Ala Asn Thr Met Asp Ala Ile His Gln
65                  70                  75                  80

Phe Ile Ile Leu Thr Asn Val Leu Gly Ser Arg Val Leu Ala Pro Ala
                85                  90                  95

Leu Thr Asn Ser Leu Thr Pro Ile Lys Asp Met Ser Leu Glu Asp Arg
            100                 105                 110

Glu Lys Leu Leu Ala Ser Trp Arg Asp Ser Pro Ile Ala Ala Lys Arg
        115                 120                 125

Lys Leu Phe Arg Leu Val Ser Thr Leu Thr Leu Val Thr Phe Thr Arg
    130                 135                 140

Leu Ala Asn Glu Leu His Leu Lys Ala Ile His Tyr Pro Gly Arg Glu
145                 150                 155                 160

Asp Arg Glu Lys Ala Tyr Glu Thr Gln Glu Ile Asp Pro Phe Lys Tyr
                165                 170                 175

Gln Phe Leu Glu Lys Pro Lys Phe Tyr Gly Ala Glu Leu Tyr Leu Pro
            180                 185                 190

Asp Ile Asp Val Ile Ile Ile Gly Ser Gly Ala Gly Ala Gly Val Val
        195                 200                 205

Ala His Thr Leu Thr Asn Asp Gly Phe Lys Ser Leu Val Leu Glu Lys
    210                 215                 220

Gly Arg Tyr Phe Ser Asn Ser Glu Leu Asn Phe Asp Asp Lys Asp Gly
225                 230                 235                 240

Val Gln Glu Leu Tyr Gln Ser Gly Gly Thr Leu Thr Thr Val Asn Gln
                245                 250                 255

Gln Leu Phe Val Leu Ala Gly Ser Thr Phe Gly Gly Gly Thr Thr Val
            260                 265                 270

Asn Trp Ser Ala Cys Leu Lys Thr Pro Phe Lys Val Arg Lys Glu Trp
        275                 280                 285

Tyr Asp Glu Phe Gly Val Asp Phe Ala Ala Asp Glu Ala Tyr Asp Lys
    290                 295                 300

Ala Gln Asp Tyr Val Trp Gln Gln Met Gly Ala Ser Thr Glu Gly Ile
305                 310                 315                 320

Thr His Ser Leu Ala Asn Glu Ile Ile Ile Glu Gly Gly Lys Lys Leu
                325                 330                 335

Gly Tyr Lys Ala Lys Val Leu Asp Gln Asn Ser Gly Gly His Pro His
            340                 345                 350

His Arg Cys Gly Phe Cys Tyr Leu Gly Cys Lys His Gly Ile Lys Gln
        355                 360                 365

Gly Ser Val Asn Asn Trp Phe Arg Asp Ala Ala Ala His Gly Ser Gln
    370                 375                 380

Phe Met Gln Gln Val Arg Val Leu Gln Ile Leu Asn Lys Lys Gly Ile
385                 390                 395                 400
```

-continued

```
Ala Tyr Gly Ile Leu Cys Glu Asp Val Val Thr Gly Ala Lys Phe Thr
                405                 410                 415

Ile Thr Gly Pro Lys Lys Phe Val Val Ala Ala Gly Ala Leu Asn Thr
            420                 425                 430

Pro Ser Val Leu Val Asn Ser Gly Phe Lys Asn Lys Asn Ile Gly Lys
        435                 440                 445

Asn Leu Thr Leu His Pro Val Ser Val Val Phe Gly Asp Phe Gly Lys
    450                 455                 460

Asp Val Gln Ala Asp His Phe His Asn Ser Ile Met Thr Ala Leu Cys
465                 470                 475                 480

Ser Glu Ala Ala Asp Leu Asp Gly Lys Gly His Gly Cys Arg Ile Glu
                485                 490                 495

Thr Ile Leu Asn Ala Pro Phe Ile Gln Ala Ser Phe Leu Pro Trp Arg
            500                 505                 510

Gly Ser Asn Glu Ala Arg Arg Asp Leu Leu Arg Tyr Asn Asn Met Val
        515                 520                 525

Ala Met Leu Leu Leu Ser Arg Asp Thr Thr Ser Gly Ser Val Ser Ser
    530                 535                 540

His Pro Thr Lys Pro Glu Ala Leu Val Val Glu Tyr Asp Val Asn Lys
545                 550                 555                 560

Phe Asp Arg Asn Ser Ile Leu Gln Ala Leu Leu Val Thr Ala Asp Leu
                565                 570                 575

Leu Tyr Ile Gln Gly Ala Lys Arg Ile Leu Ser Pro Gln Pro Trp Val
            580                 585                 590

Pro Ile Phe Glu Ser Asp Lys Pro Lys Asp Lys Arg Ser Ile Lys Asp
        595                 600                 605

Glu Asp Tyr Val Glu Trp Arg Ala Lys Val Ala Lys Ile Pro Phe Asp
    610                 615                 620

Thr Tyr Gly Ser Pro Tyr Gly Ser Ala His Gln Met Ser Ser Cys Arg
625                 630                 635                 640

Met Ser Gly Lys Gly Pro Lys Tyr Gly Ala Val Asp Thr Asp Gly Arg
                645                 650                 655

Leu Phe Glu Cys Ser Asn Val Tyr Val Ala Asp Ala Ser Leu Leu Pro
            660                 665                 670

Thr Ala Ser Gly Ala Asn Pro Met Val Thr Thr Met Thr Leu Ala Arg
        675                 680                 685

His Val Ala Leu Gly Leu Ala Asp Ser Leu Lys Thr Lys Ala Lys Leu
    690                 695                 700
```

<210> SEQ ID NO 9
<211> LENGTH: 4158
<212> TYPE: DNA
<213> ORGANISM: Candida tropicalis
<220> FEATURE:
<221> NAME/KEY: CDS
<222> LOCATION: (1521)..(3632)

<400> SEQUENCE: 9

```
tctcaccaag tacgagaacg agcttgttga tagagcttag acttgtcttt tgtatttgta      60

atctgacgtt gaccgtttga gtttttcctg tgatatcacg taaatctggc aaccagcttt     120

ctattttttt tgcaacactt tttctcttca ccactctcag aaccaatgcc accgaagaag     180

ggtctcaacc aggaggaaaa gctctcgtca atcctcgcct ggttccaaag cagccactgc     240

ttctatacgc tcaaagaggt tgaacagaag gctagcaaag cgtgcaagat ctcgtctatg     300

cagatcaagg acttggttgc aaccttagtc aacgaaggtt tagtggaaca ggaaaaatgt     360
```

-continued

```
gggaccacca acttgtactg gtcgttcccg tactcggaac acaaacgcaa gctacagaga    420

tacgagcagc taagacaatc cgttgccaaa cttcaagcga ataaaggcaa gttggcggaa    480

gagttgcgaa acgcgtgtgg tgagcgtgac atggacagca ataggctaaa ccggatgcaa    540

cagtgcgatc agcttgttca cgaggcggca cgcctccagg aggaactaaa actgtcgagg    600

cagagagata ccattgacga gttggttcag gccattgact tcttcaacga gctgatagag    660

accgtcctca gctacatcag ccatcagtcg gggaccagcg tgtcggtatt gaaaacggag    720

tttgagatac ccgcagaact agaagaggct ccccagataa acaatgccgg agttagtgcg    780

taaatcgagc atgcatacgt tggagagaaa tagagaaaca gatttccggt gaaacgctac    840

aacacagacg aggaatacag aatggaacat gacggaaata taatatccga ggaaagacga    900

aagtacgaca tggaactccg ttactgcaac atcgatcgtg ctagatacga catagaacaa    960

tgttgctatt acatggaaag ctgttgctac aatccagaat acggttgtac tcaagggaga   1020

tgaggctggg agccgagtgg tacataaata ggcatatagg accgtcactt ggtctaggat   1080

cgtgtagagg gtggaagagg taggcaagat ccattctaat ctactgagtg acggctaata   1140

tacgatcagc gttctcaggc gagcacagtc attcctcatt tctgtacata cgttgcccct   1200

ttatgttttt tttcacagga tgctcacgcc caacatttcc ccccacattt tattacccac   1260

attgagccgt caaatgcatt ttttttatcc gtcgcttgct aagacaaaat tccacatgct   1320

ttgtctcaga gtatataaac aacggggcaa aaaaacatgg ggttaatagc ttattcgtgg   1380

attgatattt ttatatttta gttcgcccct ttcgccacca agctcaattg gactatttgt   1440

cagtggtgta taagctagag attactagac tgcttttctg attcttgatt ttccctttc    1500

attagttcca gtacctagag atg aat acc ttc ttg cca gac gtg ctc gaa tac   1553
                      Met Asn Thr Phe Leu Pro Asp Val Leu Glu Tyr
                      1               5                   10

aaa cac gtc gac acc ctt ttg tta ttg tgt gac ggg atc atc cac gaa      1601
Lys His Val Asp Thr Leu Leu Leu Leu Cys Asp Gly Ile Ile His Glu
            15                  20                  25

acc aca gtc gat cag atc aag gac gcc att gct ccc gac ttc cct gag      1649
Thr Thr Val Asp Gln Ile Lys Asp Ala Ile Ala Pro Asp Phe Pro Glu
        30                  35                  40

gac cag tac gag gag tat ctc aag acc ttc acc aag cca tct gag acc      1697
Asp Gln Tyr Glu Glu Tyr Leu Lys Thr Phe Thr Lys Pro Ser Glu Thr
    45                  50                  55

cct ggg ttc aga gaa gcc gtc tac gac acg atc aac gcc acc cca acc      1745
Pro Gly Phe Arg Glu Ala Val Tyr Asp Thr Ile Asn Ala Thr Pro Thr
60                  65                  70                  75

gat gcc gtg cac atg tgt att gtc ttg acc acc gca ttg gac tcc aga      1793
Asp Ala Val His Met Cys Ile Val Leu Thr Thr Ala Leu Asp Ser Arg
                80                  85                  90

atc ttg gcc ccc acg ttg acc aac tcg ttg acg cct atc aag gat atg      1841
Ile Leu Ala Pro Thr Leu Thr Asn Ser Leu Thr Pro Ile Lys Asp Met
            95                  100                 105

acc ttg aag gag cgt gaa caa ttg ttg gcc tct tgg cgt gat tcc ccg      1889
Thr Leu Lys Glu Arg Glu Gln Leu Leu Ala Ser Trp Arg Asp Ser Pro
        110                 115                 120

att gcg gca aag aga aga ttg ttc aga ttg att tcc tcg ctt acc ttg      1937
Ile Ala Ala Lys Arg Arg Leu Phe Arg Leu Ile Ser Ser Leu Thr Leu
    125                 130                 135

acg acg ttt acg aga ttg gcc agc gaa ttg cac ttg aaa gcc atc cac      1985
Thr Thr Phe Thr Arg Leu Ala Ser Glu Leu His Leu Lys Ala Ile His
140                 145                 150                 155
```

-continued

```
tac cct ggc aga gac ttg cgt gaa aag gcg tat gaa acc cag gtg gtt      2033
Tyr Pro Gly Arg Asp Leu Arg Glu Lys Ala Tyr Glu Thr Gln Val Val
            160                 165                 170

gac cct ttc agg tac tcg ttt atg gag aaa cca aag ttt gac ggc gcc      2081
Asp Pro Phe Arg Tyr Ser Phe Met Glu Lys Pro Lys Phe Asp Gly Ala
        175                 180                 185

gaa ttg tac ttg cca gat atc gac gtc atc atc att gga tca ggc gcc      2129
Glu Leu Tyr Leu Pro Asp Ile Asp Val Ile Ile Ile Gly Ser Gly Ala
    190                 195                 200

ggt gct ggt gtc atg gcc cac act ctc gcc aac gac ggg ttc aag acc      2177
Gly Ala Gly Val Met Ala His Thr Leu Ala Asn Asp Gly Phe Lys Thr
205                 210                 215

ttg gtt ttg gaa aag gga aag tat ttc agc aac tcc gag ttg aac ttt      2225
Leu Val Leu Glu Lys Gly Lys Tyr Phe Ser Asn Ser Glu Leu Asn Phe
220                 225                 230                 235

aat gac gct gat ggc gtg aaa gag ttg tac caa ggt aaa ggt gct ttg      2273
Asn Asp Ala Asp Gly Val Lys Glu Leu Tyr Gln Gly Lys Gly Ala Leu
            240                 245                 250

gcc acc acc aat cag cag atg ttt att ctt gcc ggt tcc act ttg ggc      2321
Ala Thr Thr Asn Gln Gln Met Phe Ile Leu Ala Gly Ser Thr Leu Gly
        255                 260                 265

ggt ggt acc act gtc aac tgg tct gct tgc ctt aaa aca cca ttt aaa      2369
Gly Gly Thr Thr Val Asn Trp Ser Ala Cys Leu Lys Thr Pro Phe Lys
    270                 275                 280

gtg cgt aag gag tgg tac gac gag ttt ggt ctt gaa ttt gct gcc gat      2417
Val Arg Lys Glu Trp Tyr Asp Glu Phe Gly Leu Glu Phe Ala Ala Asp
285                 290                 295

gaa gcc tac gac aaa gcg cag gat tat gtt tgg aaa caa atg ggt gct      2465
Glu Ala Tyr Asp Lys Ala Gln Asp Tyr Val Trp Lys Gln Met Gly Ala
300                 305                 310                 315

tca aca gat gga atc act cac tcc ttg gcc aac gaa gtt gtg gtt gaa      2513
Ser Thr Asp Gly Ile Thr His Ser Leu Ala Asn Glu Val Val Val Glu
            320                 325                 330

gga ggt aag aag ttg ggc tac aag agc aag gaa att gag cag aac aac      2561
Gly Gly Lys Lys Leu Gly Tyr Lys Ser Lys Glu Ile Glu Gln Asn Asn
        335                 340                 345

ggt ggc cac cct gac cac cca tgt ggt ttc tgt tac ttg ggc tgt aag      2609
Gly Gly His Pro Asp His Pro Cys Gly Phe Cys Tyr Leu Gly Cys Lys
    350                 355                 360

tac ggt att aaa cag ggt tct gtg aat aac tgg ttt aga gac gca gct      2657
Tyr Gly Ile Lys Gln Gly Ser Val Asn Asn Trp Phe Arg Asp Ala Ala
365                 370                 375

gcc cac ggg tcc aag ttc atg caa caa gtc aga gtt gtg caa atc ctc      2705
Ala His Gly Ser Lys Phe Met Gln Gln Val Arg Val Val Gln Ile Leu
380                 385                 390                 395

aac aag aat ggc gtc gct tat ggt atc ttg tgt gag gat gtc gaa acc      2753
Asn Lys Asn Gly Val Ala Tyr Gly Ile Leu Cys Glu Asp Val Glu Thr
            400                 405                 410

gga gtc agg ttc act att agt ggc ccc aaa aag ttt gtt gtt tct gct      2801
Gly Val Arg Phe Thr Ile Ser Gly Pro Lys Lys Phe Val Val Ser Ala
        415                 420                 425

ggt tct ttg aac acg cca act gtg ttg acc aac tcc gga ttc aag aac      2849
Gly Ser Leu Asn Thr Pro Thr Val Leu Thr Asn Ser Gly Phe Lys Asn
    430                 435                 440

aag cac att ggt aag aac ttg acg ttg cac cca gtt tcc acc gtg ttt      2897
Lys His Ile Gly Lys Asn Leu Thr Leu His Pro Val Ser Thr Val Phe
445                 450                 455

ggt gac ttt ggc aga gac gtg caa gcc gac cat ttc cac aaa tct att      2945
Gly Asp Phe Gly Arg Asp Val Gln Ala Asp His Phe His Lys Ser Ile
460                 465                 470                 475
```

-continued

```
atg act tcg ctt tgt tac gag gtt gct gac ttg gac ggc aag ggc cac     2993
Met Thr Ser Leu Cys Tyr Glu Val Ala Asp Leu Asp Gly Lys Gly His
                480                 485                 490

gga tgc aga atc gaa acc atc ttg aac gct cca ttc atc caa gct tct     3041
Gly Cys Arg Ile Glu Thr Ile Leu Asn Ala Pro Phe Ile Gln Ala Ser
            495                 500                 505

ttg ttg cca tgg aga gga agt gac gag gtc aga aga gac ttg ttg cgt     3089
Leu Leu Pro Trp Arg Gly Ser Asp Glu Val Arg Arg Asp Leu Leu Arg
        510                 515                 520

tac aac aac atg gtg gcc atg ttg ctt atc acg cgt gat acc acc agt     3137
Tyr Asn Asn Met Val Ala Met Leu Leu Ile Thr Arg Asp Thr Thr Ser
    525                 530                 535

ggt tca gtt tct gct gac cca aag aag ccc gac gct ttg att gtc gac     3185
Gly Ser Val Ser Ala Asp Pro Lys Lys Pro Asp Ala Leu Ile Val Asp
540                 545                 550                 555

tat gag att aac aag ttt gac aag aat gcc atc ttg caa gct ttc ttg     3233
Tyr Glu Ile Asn Lys Phe Asp Lys Asn Ala Ile Leu Gln Ala Phe Leu
                560                 565                 570

atc act tcc gac atg ttg tac att gaa ggt gcc aag aga atc ctc agt     3281
Ile Thr Ser Asp Met Leu Tyr Ile Glu Gly Ala Lys Arg Ile Leu Ser
            575                 580                 585

cca cag cca tgg gtg cca atc ttt gag tcg aac aag cca aag gag caa     3329
Pro Gln Pro Trp Val Pro Ile Phe Glu Ser Asn Lys Pro Lys Glu Gln
        590                 595                 600

aga acg atc aag gac aag gac tat gtt gag tgg aga gcc aag gct gct     3377
Arg Thr Ile Lys Asp Lys Asp Tyr Val Glu Trp Arg Ala Lys Ala Ala
    605                 610                 615

aag ata cct ttc gac acc tac ggt tct gca tat ggg tcc gca cat caa     3425
Lys Ile Pro Phe Asp Thr Tyr Gly Ser Ala Tyr Gly Ser Ala His Gln
620                 625                 630                 635

atg tcc acc tgt cgt atg tcc gga aag ggt cct aaa tac ggt gct gtt     3473
Met Ser Thr Cys Arg Met Ser Gly Lys Gly Pro Lys Tyr Gly Ala Val
                640                 645                 650

gat act gat ggt aga ttg ttt gaa tgt tcg aat gtc tat gtt gct gat     3521
Asp Thr Asp Gly Arg Leu Phe Glu Cys Ser Asn Val Tyr Val Ala Asp
            655                 660                 665

gct agt gtt ttg cct act gcc agc ggt gcc aac cca atg ata tcc acc     3569
Ala Ser Val Leu Pro Thr Ala Ser Gly Ala Asn Pro Met Ile Ser Thr
        670                 675                 680

atg acc ttt gct aga cag att gcg tta ggt ttg gct gac tcc ttg aag     3617
Met Thr Phe Ala Arg Gln Ile Ala Leu Gly Leu Ala Asp Ser Leu Lys
    685                 690                 695

acc aaa ccc aag ttg tagagagacg gaaatacgac acttatatac tagatgtatc     3672
Thr Lys Pro Lys Leu
700

ttacaattta tattctcgat gatggctttt actatctcct atgttacact ataatgacat   3732

caccacaacc tctactactg tctccagtat cctccttgct gttgaccgta cccaccagcc   3792

tgttgattga accctgtgaa ctgtggttgc tgttgagcgt accccacgtt agtgaactgc   3852

ggttgttggg caaactgctg tacgggctgt tgctgctgct gctgttgttg ttgttgttgt   3912

tgtcccgtgg gctggttgta caacgacatg atgttctgct tgtttgtctg ttgggcaacc   3972

aactgtgggt tattcatctg catcaactgc tgctggtgtt gagggttgtt tggatccaag   4032

tactcttgcc cgttggcgtc gatataagaa atctgccccg tgactgggtc agtgtactgg   4092

tatatctgtg gcatgccacc agcttgtgca ggcatgccgg ttgccaatgg cacctgtgct   4152

tgcgtc                                                              4158
```

-continued

<210> SEQ ID NO 10
<211> LENGTH: 704
<212> TYPE: PRT
<213> ORGANISM: Candida tropicalis

<400> SEQUENCE: 10

```
Met Asn Thr Phe Leu Pro Asp Val Leu Glu Tyr Lys His Val Asp Thr
1               5                   10                  15

Leu Leu Leu Leu Cys Asp Gly Ile Ile His Glu Thr Thr Val Asp Gln
            20                  25                  30

Ile Lys Asp Ala Ile Ala Pro Asp Phe Pro Glu Asp Gln Tyr Glu Glu
        35                  40                  45

Tyr Leu Lys Thr Phe Thr Lys Pro Ser Glu Thr Pro Gly Phe Arg Glu
    50                  55                  60

Ala Val Tyr Asp Thr Ile Asn Ala Thr Pro Thr Asp Ala Val His Met
65                  70                  75                  80

Cys Ile Val Leu Thr Thr Ala Leu Asp Ser Arg Ile Leu Ala Pro Thr
                85                  90                  95

Leu Thr Asn Ser Leu Thr Pro Ile Lys Asp Met Thr Leu Lys Glu Arg
            100                 105                 110

Glu Gln Leu Leu Ala Ser Trp Arg Asp Ser Pro Ile Ala Ala Lys Arg
        115                 120                 125

Arg Leu Phe Arg Leu Ile Ser Ser Leu Thr Leu Thr Thr Phe Thr Arg
    130                 135                 140

Leu Ala Ser Glu Leu His Leu Lys Ala Ile His Tyr Pro Gly Arg Asp
145                 150                 155                 160

Leu Arg Glu Lys Ala Tyr Glu Thr Gln Val Val Asp Pro Phe Arg Tyr
                165                 170                 175

Ser Phe Met Glu Lys Pro Lys Phe Asp Gly Ala Glu Leu Tyr Leu Pro
            180                 185                 190

Asp Ile Asp Val Ile Ile Ile Gly Ser Gly Ala Gly Ala Gly Val Met
        195                 200                 205

Ala His Thr Leu Ala Asn Asp Gly Phe Lys Thr Leu Val Leu Glu Lys
    210                 215                 220

Gly Lys Tyr Phe Ser Asn Ser Glu Leu Asn Phe Asn Asp Ala Asp Gly
225                 230                 235                 240

Val Lys Glu Leu Tyr Gln Gly Lys Gly Ala Leu Ala Thr Thr Asn Gln
                245                 250                 255

Gln Met Phe Ile Leu Ala Gly Ser Thr Leu Gly Gly Gly Thr Thr Val
            260                 265                 270

Asn Trp Ser Ala Cys Leu Lys Thr Pro Phe Lys Val Arg Lys Glu Trp
        275                 280                 285

Tyr Asp Glu Phe Gly Leu Glu Phe Ala Ala Asp Glu Ala Tyr Asp Lys
    290                 295                 300

Ala Gln Asp Tyr Val Trp Lys Gln Met Gly Ala Ser Thr Asp Gly Ile
305                 310                 315                 320

Thr His Ser Leu Ala Asn Glu Val Val Val Glu Gly Gly Lys Lys Leu
                325                 330                 335

Gly Tyr Lys Ser Lys Glu Ile Glu Gln Asn Asn Gly Gly His Pro Asp
            340                 345                 350

His Pro Cys Gly Phe Cys Tyr Leu Gly Cys Lys Tyr Gly Ile Lys Gln
        355                 360                 365

Gly Ser Val Asn Asn Trp Phe Arg Asp Ala Ala Ala His Gly Ser Lys
    370                 375                 380
```

-continued

```
Phe Met Gln Gln Val Arg Val Val Gln Ile Leu Asn Lys Asn Gly Val
385                 390                 395                 400

Ala Tyr Gly Ile Leu Cys Glu Asp Val Glu Thr Gly Val Arg Phe Thr
                405                 410                 415

Ile Ser Gly Pro Lys Lys Phe Val Val Ser Ala Gly Ser Leu Asn Thr
            420                 425                 430

Pro Thr Val Leu Thr Asn Ser Gly Phe Lys Asn Lys His Ile Gly Lys
        435                 440                 445

Asn Leu Thr Leu His Pro Val Ser Thr Val Phe Gly Asp Phe Gly Arg
    450                 455                 460

Asp Val Gln Ala Asp His Phe His Lys Ser Ile Met Thr Ser Leu Cys
465                 470                 475                 480

Tyr Glu Val Ala Asp Leu Asp Gly Lys Gly His Gly Cys Arg Ile Glu
                485                 490                 495

Thr Ile Leu Asn Ala Pro Phe Ile Gln Ala Ser Leu Leu Pro Trp Arg
            500                 505                 510

Gly Ser Asp Glu Val Arg Arg Asp Leu Leu Arg Tyr Asn Asn Met Val
        515                 520                 525

Ala Met Leu Leu Ile Thr Arg Asp Thr Thr Ser Gly Ser Val Ser Ala
    530                 535                 540

Asp Pro Lys Lys Pro Asp Ala Leu Ile Val Asp Tyr Glu Ile Asn Lys
545                 550                 555                 560

Phe Asp Lys Asn Ala Ile Leu Gln Ala Phe Leu Ile Thr Ser Asp Met
                565                 570                 575

Leu Tyr Ile Glu Gly Ala Lys Arg Ile Leu Ser Pro Gln Pro Trp Val
            580                 585                 590

Pro Ile Phe Glu Ser Asn Lys Pro Lys Glu Gln Arg Thr Ile Lys Asp
        595                 600                 605

Lys Asp Tyr Val Glu Trp Arg Ala Lys Ala Ala Lys Ile Pro Phe Asp
    610                 615                 620

Thr Tyr Gly Ser Ala Tyr Gly Ser Ala His Gln Met Ser Thr Cys Arg
625                 630                 635                 640

Met Ser Gly Lys Gly Pro Lys Tyr Gly Ala Val Asp Thr Asp Gly Arg
                645                 650                 655

Leu Phe Glu Cys Ser Asn Val Tyr Val Ala Asp Ala Ser Val Leu Pro
            660                 665                 670

Thr Ala Ser Gly Ala Asn Pro Met Ile Ser Thr Met Thr Phe Ala Arg
        675                 680                 685

Gln Ile Ala Leu Gly Leu Ala Asp Ser Leu Lys Thr Lys Pro Lys Leu
    690                 695                 700
```

```
<210> SEQ ID NO 11
<211> LENGTH: 3753
<212> TYPE: DNA
<213> ORGANISM: Candida tropicalis
<220> FEATURE:
<221> NAME/KEY: CDS
<222> LOCATION: (1099)..(3213)

<400> SEQUENCE: 11

tgttgataga gcttagactt gtgttttgta tttgtaatct gacgttgatc gtttgatatt      60

ttcctgtgat atcacgtaaa ttcggcaacc aactttttac tttttgcaac actttctctt     120

caccactctc agaaccaatg ccaccgaaga agggtctcag ccaggaggaa aagctctcgg     180

cactcctcac ctggttccaa gccagtcatt gcttctacac actcaaggag gttgaacaga     240
```

-continued

```
aggcgagcaa agcgtgcaag atctcgtcta tgcagatcaa ggacttggtt gcaagcttag    300

tcaacgaagg tttggtagaa caggaaaagt gtgggaccac aaacttgtac tggtcgttcc    360

agtactcgga attcaaacgg aagctacaga gatacgggca gctaagacaa tcagccgcca    420

aacttcaagc ggataaaggc aagttggcgg aagagttgcg aaacgcatgt ggtgaacggg    480

acatggacaa caataggcaa gaccggatgc aacaatacga tcaccttgtt aacgaggcgg    540

cacgtctcca ggaggaacta aaactgtcaa ggcagataga taccattgac gagttagttc    600

aggccattga tttcttcaac gagctgatag agaccgtcct cagctacatc agccatcagt    660

cagggaccag cgtgtcgata ttgaaaacgg agtttgagat acccgcagaa ctagaagagg    720

ccccccagat aagcaatgcc ggagttagtg cgtaaatcga gcaggcatac attgcccctt    780

tgtatttttt cacaggatgc tcaccccacc acgcccaaca tttcccccca cattttatta    840

cccacattga gccgtcaaat gcattttttt atccgtcgct agctaaacca aaattccaca    900

tgcgttgcct cagagtatat aaacaacggg gcaaaaaaca tgggattaat agcttatttg    960

tggattgata tttttatatt ttagttcgcc ccttctacga ccaagctcaa ttggactatt   1020

tgtcagtggt gtataagcta gagattacta gactgctttt ctgattcttg atcatcccct   1080

tagttccagt gcctagag atg aat acc ttc ttg cca gac gtg ctc gaa tac     1131
                    Met Asn Thr Phe Leu Pro Asp Val Leu Glu Tyr
                    1               5                   10

aaa cac gtc gat acc ctt ttg tta tta tgt gac ggg atc atc cac gaa     1179
Lys His Val Asp Thr Leu Leu Leu Leu Cys Asp Gly Ile Ile His Glu
            15                  20                  25

acc aca gtc gac cag atc agg gac gcc att gct ccc gac ttc cct gaa     1227
Thr Thr Val Asp Gln Ile Arg Asp Ala Ile Ala Pro Asp Phe Pro Glu
        30                  35                  40

gac cag tac gag gag tat ctc aag acc ttc acc aag cca tct gag acc     1275
Asp Gln Tyr Glu Glu Tyr Leu Lys Thr Phe Thr Lys Pro Ser Glu Thr
    45                  50                  55

cct ggg ttc aga gaa gcc gtc tac gac acg atc aac agc acc cca acc     1323
Pro Gly Phe Arg Glu Ala Val Tyr Asp Thr Ile Asn Ser Thr Pro Thr
60                  65                  70                  75

gag gct gtg cac atg tgt att gta ttg acc acc gca ttg gac tcg aga     1371
Glu Ala Val His Met Cys Ile Val Leu Thr Thr Ala Leu Asp Ser Arg
                80                  85                  90

atc ttg gcc ccc acg ttg acc aac tcg ttg acg cct atc aag gat atg     1419
Ile Leu Ala Pro Thr Leu Thr Asn Ser Leu Thr Pro Ile Lys Asp Met
            95                  100                 105

acc ttg aaa gag cgt gaa caa ttg ttg gct gcc tgg cgt gat tcc ccg     1467
Thr Leu Lys Glu Arg Glu Gln Leu Leu Ala Ala Trp Arg Asp Ser Pro
        110                 115                 120

atc gcg gcc aag aga aga ttg ttc aga ttg att tcc tca ctt acc ttg     1515
Ile Ala Ala Lys Arg Arg Leu Phe Arg Leu Ile Ser Ser Leu Thr Leu
    125                 130                 135

acg acc ttt acg aga ttg gcc agc gac ttg cac ttg aga gcc atc cac     1563
Thr Thr Phe Thr Arg Leu Ala Ser Asp Leu His Leu Arg Ala Ile His
140                 145                 150                 155

tac cct ggc aga gac ttg cgt gaa aag gca tat gaa acc cag gtg gtt     1611
Tyr Pro Gly Arg Asp Leu Arg Glu Lys Ala Tyr Glu Thr Gln Val Val
                160                 165                 170

gac cct ttc agg tac tcg ttt atg gaa aaa cca aag ttt gac ggc acc     1659
Asp Pro Phe Arg Tyr Ser Phe Met Glu Lys Pro Lys Phe Asp Gly Thr
            175                 180                 185

gag ttg tac ttg cca gat atc gac gtc atc atc att gga tcc ggt gcc     1707
Glu Leu Tyr Leu Pro Asp Ile Asp Val Ile Ile Ile Gly Ser Gly Ala
```

-continued

```
        190                 195                 200

ggt gct ggt gtc atg gcc cac act tta gcc aac gac ggg tac aag acc      1755
Gly Ala Gly Val Met Ala His Thr Leu Ala Asn Asp Gly Tyr Lys Thr
    205                 210                 215

ttg gtt ttg gaa aag gga aag tat ttc agc aac tcc gag ttg aac ttt      1803
Leu Val Leu Glu Lys Gly Lys Tyr Phe Ser Asn Ser Glu Leu Asn Phe
220                 225                 230                 235

aat gat gcc gat ggt atg aaa gag ttg tac caa ggt aaa tgt gcg ttg      1851
Asn Asp Ala Asp Gly Met Lys Glu Leu Tyr Gln Gly Lys Cys Ala Leu
                240                 245                 250

acc acc acg aac cag cag atg ttt att ctt gcc ggt tcc act ttg ggc      1899
Thr Thr Thr Asn Gln Gln Met Phe Ile Leu Ala Gly Ser Thr Leu Gly
            255                 260                 265

ggt ggt acc act gtt aac tgg tct gct tgt ctt aaa aca cca ttt aaa      1947
Gly Gly Thr Thr Val Asn Trp Ser Ala Cys Leu Lys Thr Pro Phe Lys
        270                 275                 280

gtg cgt aag gag tgg tac gac gag ttt ggt ctt gaa ttt gct gcc gac      1995
Val Arg Lys Glu Trp Tyr Asp Glu Phe Gly Leu Glu Phe Ala Ala Asp
    285                 290                 295

gaa gcc tac gac aaa gca caa gac tat gtt tgg aaa caa atg ggc gct      2043
Glu Ala Tyr Asp Lys Ala Gln Asp Tyr Val Trp Lys Gln Met Gly Ala
300                 305                 310                 315

tct acc gaa gga atc act cac tct ttg gcg aac gcg gtt gtg gtt gaa      2091
Ser Thr Glu Gly Ile Thr His Ser Leu Ala Asn Ala Val Val Val Glu
                320                 325                 330

gga ggt aag aag ttg ggt tac aag agc aag gaa atc gag cag aac aat      2139
Gly Gly Lys Lys Leu Gly Tyr Lys Ser Lys Glu Ile Glu Gln Asn Asn
            335                 340                 345

ggt ggc cat cct gac cac ccc tgt ggt ttc tgt tac ttg ggc tgt aag      2187
Gly Gly His Pro Asp His Pro Cys Gly Phe Cys Tyr Leu Gly Cys Lys
        350                 355                 360

tac ggt att aag cag ggt tct gtg aat aac tgg ttt aga gac gca gct      2235
Tyr Gly Ile Lys Gln Gly Ser Val Asn Asn Trp Phe Arg Asp Ala Ala
    365                 370                 375

gcc cac ggg tcc aag ttc atg caa caa gtc aga gtt gtg caa atc ctc      2283
Ala His Gly Ser Lys Phe Met Gln Gln Val Arg Val Val Gln Ile Leu
380                 385                 390                 395

cac aat aaa ggc gtc gct tat ggc atc ttg tgt gag gat gtc gag acc      2331
His Asn Lys Gly Val Ala Tyr Gly Ile Leu Cys Glu Asp Val Glu Thr
                400                 405                 410

gga gtc aaa ttc act atc agt ggc ccc aaa aag ttt gtt gtt tct gca      2379
Gly Val Lys Phe Thr Ile Ser Gly Pro Lys Lys Phe Val Val Ser Ala
            415                 420                 425

ggt tct ttg aac acg cca acg gtg ttg acc aac tcc gga ttc aag aac      2427
Gly Ser Leu Asn Thr Pro Thr Val Leu Thr Asn Ser Gly Phe Lys Asn
        430                 435                 440

aaa cac atc ggt aag aac ttg acg ttg cac cca gtt tcg acc gtg ttt      2475
Lys His Ile Gly Lys Asn Leu Thr Leu His Pro Val Ser Thr Val Phe
    445                 450                 455

ggt gac ttt ggc aga gac gtg caa gcc gac cat ttc cac aaa tct att      2523
Gly Asp Phe Gly Arg Asp Val Gln Ala Asp His Phe His Lys Ser Ile
460                 465                 470                 475

atg act tcg ctc tgt tac gaa gtc gct gac ttg gac ggc aag ggc cac      2571
Met Thr Ser Leu Cys Tyr Glu Val Ala Asp Leu Asp Gly Lys Gly His
                480                 485                 490

gga tgc aga atc gag acc atc ttg aac gct cca ttc atc caa gct tct      2619
Gly Cys Arg Ile Glu Thr Ile Leu Asn Ala Pro Phe Ile Gln Ala Ser
            495                 500                 505

ttg ttg cca tgg aga gga agc gac gag gtc aga aga gac ttg ttg cgt      2667
```

-continued

```
Leu Leu Pro Trp Arg Gly Ser Asp Glu Val Arg Arg Asp Leu Leu Arg
        510                 515                 520

tac aac aac atg gtg gcc atg ttg ctt atc acc cgt gac acc acc agt     2715
Tyr Asn Asn Met Val Ala Met Leu Leu Ile Thr Arg Asp Thr Thr Ser
    525                 530                 535

ggt tca gtt tct gct gac cca aag aag ccc gac gct ttg att gtc gac     2763
Gly Ser Val Ser Ala Asp Pro Lys Lys Pro Asp Ala Leu Ile Val Asp
540                 545                 550                 555

tat gac atc aac aag ttt gac aag aat gcc atc ttg caa gct ttc ttg     2811
Tyr Asp Ile Asn Lys Phe Asp Lys Asn Ala Ile Leu Gln Ala Phe Leu
                560                 565                 570

atc acc tcc gac atg ttg tac atc gaa ggt gcc aag aga atc ctc agt     2859
Ile Thr Ser Asp Met Leu Tyr Ile Glu Gly Ala Lys Arg Ile Leu Ser
            575                 580                 585

cca cag gca tgg gtg cca atc ttt gag tcg aac aag cca aag gag caa     2907
Pro Gln Ala Trp Val Pro Ile Phe Glu Ser Asn Lys Pro Lys Glu Gln
        590                 595                 600

aga aca atc aag gac aag gac tat gtc gaa tgg aga gcc aag gct gcc     2955
Arg Thr Ile Lys Asp Lys Asp Tyr Val Glu Trp Arg Ala Lys Ala Ala
    605                 610                 615

aag ata cct ttc gac acc tac ggt tct gcc tat ggg tcc gca cat caa     3003
Lys Ile Pro Phe Asp Thr Tyr Gly Ser Ala Tyr Gly Ser Ala His Gln
620                 625                 630                 635

atg tcc acc tgt cgt atg tcc gga aag ggt cct aaa tac ggc gcc gtt     3051
Met Ser Thr Cys Arg Met Ser Gly Lys Gly Pro Lys Tyr Gly Ala Val
                640                 645                 650

gat acc gat ggt aga ttg ttt gaa tgt tcg aat gtc tat gtt gct gat     3099
Asp Thr Asp Gly Arg Leu Phe Glu Cys Ser Asn Val Tyr Val Ala Asp
            655                 660                 665

gct agt gtt ttg cct act gcc agc ggt gcc aac cca atg atc tcc acc     3147
Ala Ser Val Leu Pro Thr Ala Ser Gly Ala Asn Pro Met Ile Ser Thr
        670                 675                 680

atg acg ttt gct aga cag att gcg tta ggt ttg gct gac tct ttg aag     3195
Met Thr Phe Ala Arg Gln Ile Ala Leu Gly Leu Ala Asp Ser Leu Lys
    685                 690                 695

acc aaa ccc aag ttg tag agagagacag aaatacgaca cttatatact            3243
Thr Lys Pro Lys Leu
700

agatgtatct tacaatttat attttcgatg atggctttta ctatctccta tgttacacta   3303

taatgacatc accacatctt ctactactgt ctccagtatc ctccttgctg ttgaccgtat   3363

ccaccagcct gttggttgaa ccccgtgaac tgtggttgct gttgagcgta ccccacgtta   3423

gtgaactgcg gttgttgggt aaactgctgt acgggctgtt gttgctgttg ctgttgttgc   3483

tgttgttgct gttgttgctg ttgttgctgt tgttgttgtt gtcccgttgg ctggttgtac   3543

aacgacatga tgttctgctt gtttgtctgc tgggcaacca actgtgggtt attcatctgc   3603

atcaactgct gctggtgctg aggggttgttt ggatccaagt actcctgccc gttggcgtcg   3663

atataagaaa tctgccccgt gactgggtca gtgtactggt atatctgtgg catgccaccc   3723

gcttgtgcag gcatgccggt tgccaatggc                                    3753


<210> SEQ ID NO 12
<211> LENGTH: 704
<212> TYPE: PRT
<213> ORGANISM: Candida tropicalis

<400> SEQUENCE: 12

Met Asn Thr Phe Leu Pro Asp Val Leu Glu Tyr Lys His Val Asp Thr
1               5                   10                  15
```

-continued

```
Leu Leu Leu Leu Cys Asp Gly Ile Ile His Glu Thr Thr Val Asp Gln
            20                  25                  30

Ile Arg Asp Ala Ile Ala Pro Asp Phe Pro Glu Asp Gln Tyr Glu Glu
        35                  40                  45

Tyr Leu Lys Thr Phe Thr Lys Pro Ser Glu Thr Pro Gly Phe Arg Glu
    50                  55                  60

Ala Val Tyr Asp Thr Ile Asn Ser Thr Pro Thr Glu Ala Val His Met
65                  70                  75                  80

Cys Ile Val Leu Thr Thr Ala Leu Asp Ser Arg Ile Leu Ala Pro Thr
                85                  90                  95

Leu Thr Asn Ser Leu Thr Pro Ile Lys Asp Met Thr Leu Lys Glu Arg
            100                 105                 110

Glu Gln Leu Leu Ala Ala Trp Arg Asp Ser Pro Ile Ala Ala Lys Arg
        115                 120                 125

Arg Leu Phe Arg Leu Ile Ser Ser Leu Thr Leu Thr Thr Phe Thr Arg
    130                 135                 140

Leu Ala Ser Asp Leu His Leu Arg Ala Ile His Tyr Pro Gly Arg Asp
145                 150                 155                 160

Leu Arg Glu Lys Ala Tyr Glu Thr Gln Val Val Asp Pro Phe Arg Tyr
                165                 170                 175

Ser Phe Met Glu Lys Pro Lys Phe Asp Gly Thr Glu Leu Tyr Leu Pro
            180                 185                 190

Asp Ile Asp Val Ile Ile Ile Gly Ser Gly Ala Gly Ala Gly Val Met
        195                 200                 205

Ala His Thr Leu Ala Asn Asp Gly Tyr Lys Thr Leu Val Leu Glu Lys
    210                 215                 220

Gly Lys Tyr Phe Ser Asn Ser Glu Leu Asn Phe Asn Asp Ala Asp Gly
225                 230                 235                 240

Met Lys Glu Leu Tyr Gln Gly Lys Cys Ala Leu Thr Thr Thr Asn Gln
                245                 250                 255

Gln Met Phe Ile Leu Ala Gly Ser Thr Leu Gly Gly Gly Thr Thr Val
            260                 265                 270

Asn Trp Ser Ala Cys Leu Lys Thr Pro Phe Lys Val Arg Lys Glu Trp
        275                 280                 285

Tyr Asp Glu Phe Gly Leu Glu Phe Ala Ala Asp Glu Ala Tyr Asp Lys
    290                 295                 300

Ala Gln Asp Tyr Val Trp Lys Gln Met Gly Ala Ser Thr Glu Gly Ile
305                 310                 315                 320

Thr His Ser Leu Ala Asn Ala Val Val Val Glu Gly Gly Lys Lys Leu
                325                 330                 335

Gly Tyr Lys Ser Lys Glu Ile Glu Gln Asn Asn Gly Gly His Pro Asp
            340                 345                 350

His Pro Cys Gly Phe Cys Tyr Leu Gly Cys Lys Tyr Gly Ile Lys Gln
        355                 360                 365

Gly Ser Val Asn Asn Trp Phe Arg Asp Ala Ala Ala His Gly Ser Lys
    370                 375                 380

Phe Met Gln Gln Val Arg Val Val Gln Ile Leu His Asn Lys Gly Val
385                 390                 395                 400

Ala Tyr Gly Ile Leu Cys Glu Asp Val Glu Thr Gly Val Lys Phe Thr
                405                 410                 415

Ile Ser Gly Pro Lys Lys Phe Val Val Ser Ala Gly Ser Leu Asn Thr
            420                 425                 430
```

-continued

```
Pro Thr Val Leu Thr Asn Ser Gly Phe Lys Asn Lys His Ile Gly Lys
        435                 440                 445

Asn Leu Thr Leu His Pro Val Ser Thr Val Phe Gly Asp Phe Gly Arg
    450                 455                 460

Asp Val Gln Ala Asp His Phe His Lys Ser Ile Met Thr Ser Leu Cys
465                 470                 475                 480

Tyr Glu Val Ala Asp Leu Asp Gly Lys Gly His Gly Cys Arg Ile Glu
                485                 490                 495

Thr Ile Leu Asn Ala Pro Phe Ile Gln Ala Ser Leu Leu Pro Trp Arg
            500                 505                 510

Gly Ser Asp Glu Val Arg Arg Asp Leu Leu Arg Tyr Asn Asn Met Val
        515                 520                 525

Ala Met Leu Leu Ile Thr Arg Asp Thr Thr Ser Gly Ser Val Ser Ala
    530                 535                 540

Asp Pro Lys Lys Pro Asp Ala Leu Ile Val Asp Tyr Asp Ile Asn Lys
545                 550                 555                 560

Phe Asp Lys Asn Ala Ile Leu Gln Ala Phe Leu Ile Thr Ser Asp Met
                565                 570                 575

Leu Tyr Ile Glu Gly Ala Lys Arg Ile Leu Ser Pro Gln Ala Trp Val
            580                 585                 590

Pro Ile Phe Glu Ser Asn Lys Pro Lys Glu Gln Arg Thr Ile Lys Asp
        595                 600                 605

Lys Asp Tyr Val Glu Trp Arg Ala Lys Ala Ala Lys Ile Pro Phe Asp
    610                 615                 620

Thr Tyr Gly Ser Ala Tyr Gly Ser Ala His Gln Met Ser Thr Cys Arg
625                 630                 635                 640

Met Ser Gly Lys Gly Pro Lys Tyr Gly Ala Val Asp Thr Asp Gly Arg
                645                 650                 655

Leu Phe Glu Cys Ser Asn Val Tyr Val Ala Asp Ala Ser Val Leu Pro
            660                 665                 670

Thr Ala Ser Gly Ala Asn Pro Met Ile Ser Thr Met Thr Phe Ala Arg
        675                 680                 685

Gln Ile Ala Leu Gly Leu Ala Asp Ser Leu Lys Thr Lys Pro Lys Leu
    690                 695                 700


<210> SEQ ID NO 13
<211> LENGTH: 8
<212> TYPE: PRT
<213> ORGANISM: Candida tropicalis

<400> SEQUENCE: 13

Cys Gly Phe Cys Tyr Leu Gly Cys
1               5


<210> SEQ ID NO 14
<211> LENGTH: 12
<212> TYPE: PRT
<213> ORGANISM: Candida tropicalis

<400> SEQUENCE: 14

Ile Ile Gly Ser Gly Ala Gly Ala Gly Val Met Ala
1               5                   10


<210> SEQ ID NO 15
<211> LENGTH: 12
<212> TYPE: PRT
<213> ORGANISM: Candida tropicalis
<220> FEATURE:
```

```
<221> NAME/KEY: misc_feature
<222> LOCATION: (6)..(6)
<223> OTHER INFORMATION: Xaa can be any naturally occurring amino acid

<400> SEQUENCE: 15

Ile Ile Gly Ser Gly Xaa Gly Ala Gly Val Val Ala
1               5                   10


<210> SEQ ID NO 16
<211> LENGTH: 12
<212> TYPE: PRT
<213> ORGANISM: Candida tropicalis

<400> SEQUENCE: 16

Ile Ile Gly Ser Gly Ala Gly Ala Gly Val Val Ala
1               5                   10


<210> SEQ ID NO 17
<211> LENGTH: 12
<212> TYPE: PRT
<213> ORGANISM: Candida albicans

<400> SEQUENCE: 17

Ile Ile Gly Ser Gly Ala Gly Ser Gly Val Val Ala
1               5                   10


<210> SEQ ID NO 18
<211> LENGTH: 8
<212> TYPE: PRT
<213> ORGANISM: Candida tropicalis

<400> SEQUENCE: 18

Ala Gly Ser Thr Phe Gly Gly Gly
1               5


<210> SEQ ID NO 19
<211> LENGTH: 8
<212> TYPE: PRT
<213> ORGANISM: Candida tropicalis

<400> SEQUENCE: 19

Ala Gly Ser Thr Leu Gly Gly Gly
1               5


<210> SEQ ID NO 20
<211> LENGTH: 9
<212> TYPE: PRT
<213> ORGANISM: Candida tropicalis

<400> SEQUENCE: 20

Asn Trp Ser Ala Cys Leu Lys Thr Pro
1               5


<210> SEQ ID NO 21
<211> LENGTH: 9
<212> TYPE: PRT
<213> ORGANISM: Candida albicans

<400> SEQUENCE: 21

Asn Trp Ser Ala Cys Ile Lys Thr Pro
1               5


<210> SEQ ID NO 22
<211> LENGTH: 8
<212> TYPE: PRT
```

<213> ORGANISM: Candida tropicalis
<220> FEATURE:
<221> NAME/KEY: misc_feature
<222> LOCATION: (3)..(3)
<223> OTHER INFORMATION: Xaa can be any naturally occurring amino acid

<400> SEQUENCE: 22

Cys Gly Xaa Cys His Leu Gly Cys
1               5

<210> SEQ ID NO 23
<211> LENGTH: 8
<212> TYPE: PRT
<213> ORGANISM: Candida tropicalis

<400> SEQUENCE: 23

Cys Gly Phe Cys His Leu Gly Cys
1               5

<210> SEQ ID NO 24
<211> LENGTH: 11
<212> TYPE: PRT
<213> ORGANISM: Candida tropicalis
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 24

Ile Gly Xaa Asn Leu Xaa Leu His Pro Val Ser
1               5                   10

<210> SEQ ID NO 25
<211> LENGTH: 11
<212> TYPE: PRT
<213> ORGANISM: Candida tropicalis

<400> SEQUENCE: 25

Ile Gly Lys Asn Leu Thr Leu His Pro Val Ser
1               5                   10

<210> SEQ ID NO 26
<211> LENGTH: 11
<212> TYPE: PRT
<213> ORGANISM: Candida albicans

<400> SEQUENCE: 26

Ile Gly Ala Asn Leu Thr Leu His Pro Val Thr
1               5                   10

<210> SEQ ID NO 27
<211> LENGTH: 12
<212> TYPE: PRT
<213> ORGANISM: Candida tropicalis
<220> FEATURE:
<221> NAME/KEY: misc_feature
<222> LOCATION: (7)..(7)
<223> OTHER INFORMATION: Xaa can be any naturally occurring amino acid

<400> SEQUENCE: 27

Ser Ala His Gln Met Ser Xaa Cys Arg Met Ser Gly
1               5                   10

<210> SEQ ID NO 28
<211> LENGTH: 12
<212> TYPE: PRT
<213> ORGANISM: Candida tropicalis

<400> SEQUENCE: 28

```
Ser Ala His Gln Met Ser Thr Cys Arg Met Ser Gly
1               5                   10
```

<210> SEQ ID NO 29
<211> LENGTH: 12
<212> TYPE: PRT
<213> ORGANISM: Candida tropicalis

<400> SEQUENCE: 29

```
Ser Ala His Gln Met Ser Ser Cys Arg Met Ser Gly
1               5                   10
```

<210> SEQ ID NO 30
<211> LENGTH: 9
<212> TYPE: PRT
<213> ORGANISM: Candida tropicalis
<220> FEATURE:
<221> NAME/KEY: misc_feature
<222> LOCATION: (6)..(6)
<223> OTHER INFORMATION: Xaa can be any naturally occurring amino acid

<400> SEQUENCE: 30

```
Pro Thr Ala Ser Gly Xaa Asn Pro Met
1               5
```

<210> SEQ ID NO 31
<211> LENGTH: 9
<212> TYPE: PRT
<213> ORGANISM: Candida tropicalis

<400> SEQUENCE: 31

```
Pro Thr Ala Ser Gly Ala Asn Pro Met
1               5
```

<210> SEQ ID NO 32
<211> LENGTH: 24
<212> TYPE: DNA
<213> ORGANISM: Candida tropicalis
<220> FEATURE:
<221> NAME/KEY: misc_feature
<222> LOCATION: (3)..(3)
<223> OTHER INFORMATION: y is c or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: y is c or t
<220> FEATURE:
<221> NAME/KEY: misc_feature
<222> LOCATION: (12)..(12)
<223> OTHER INFORMATION: y is c or t
<220> FEATURE:
<221> NAME/KEY: misc_feature
<222> LOCATION: (15)..(15)
<223> OTHER INFORMATION: y is c or t
<220> FEATURE:
<221> NAME/KEY: misc_feature
<222> LOCATION: (16)..(16)
<223> OTHER INFORMATION: y is c or t
<220> FEATURE:
<221> NAME/KEY: misc_feature
<222> LOCATION: (18)..(18)

```
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: y is c or t

<400> SEQUENCE: 32

tgyggnttyt gytayytngg ntgy                                              24


<210> SEQ ID NO 33
<211> LENGTH: 36
<212> TYPE: DNA
<213> ORGANISM: Candida tropicalis
<220> FEATURE:
<221> NAME/KEY: misc_feature
<222> LOCATION: (3)..(3)
<223> OTHER INFORMATION: h is a or t or c
<220> FEATURE:
<221> NAME/KEY: misc_feature
<222> LOCATION: (6)..(6)
<223> OTHER INFORMATION: h is a or t or c
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (10)..(10)
<223> OTHER INFORMATION: w is a or t
<220> FEATURE:
<221> NAME/KEY: misc_feature
<222> LOCATION: (11)..(11)
<223> OTHER INFORMATION: s is g or c
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t

<400> SEQUENCE: 33

athathggnw snggngcngg ngcnggngtn atggcn                                 36


<210> SEQ ID NO 34
<211> LENGTH: 24
```

<212> TYPE: DNA
<213> ORGANISM: Candida tropicalis
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (7)..(7)
<223> OTHER INFORMATION: w is a or t
<220> FEATURE:
<221> NAME/KEY: misc_feature
<222> LOCATION: (8)..(8)
<223> OTHER INFORMATION: s is g or c
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (13)..(13)
<223> OTHER INFORMATION: y is c or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 34
gcnggnwsna cnytnggngg nggn 24

<210> SEQ ID NO 35
<211> LENGTH: 18
<212> TYPE: DNA
<213> ORGANISM: Candida tropicalis

<400> SEQUENCE: 35
tcgtggcgtg actctcct 18

<210> SEQ ID NO 36
<211> LENGTH: 18
<212> TYPE: DNA
<213> ORGANISM: Candida cloacae

<400> SEQUENCE: 36
tcatggagag actctcct 18

<210> SEQ ID NO 37
<211> LENGTH: 18
<212> TYPE: DNA
<213> ORGANISM: Candida cloacae

<400> SEQUENCE: 37

-continued tcatggagag actctcca 18

<210> SEQ ID NO 38
<211> LENGTH: 16
<212> TYPE: DNA
<213> ORGANISM: Candida tropicalis

<400> SEQUENCE: 38
ctggtgctgg tgtagt 16

<210> SEQ ID NO 39
<211> LENGTH: 16
<212> TYPE: DNA
<213> ORGANISM: Candida cloacae

<400> SEQUENCE: 39
caggagcagg tgtggt 16

<210> SEQ ID NO 40
<211> LENGTH: 16
<212> TYPE: DNA
<213> ORGANISM: Candida cloacae

<400> SEQUENCE: 40
cgggagcagg agtggt 16

<210> SEQ ID NO 41
<211> LENGTH: 19
<212> TYPE: DNA
<213> ORGANISM: Candida tropicalis

<400> SEQUENCE: 41
ttggtaccca tgcttgtgg 19

<210> SEQ ID NO 42
<211> LENGTH: 19
<212> TYPE: DNA
<213> ORGANISM: Candida cloacae

<400> SEQUENCE: 42
ttggtaccca agcttgtgg 19

<210> SEQ ID NO 43
<211> LENGTH: 19
<212> TYPE: DNA
<213> ORGANISM: Candida cloacae

<400> SEQUENCE: 43
ttggtaccca agcttgtag 19

<210> SEQ ID NO 44
<211> LENGTH: 18
<212> TYPE: DNA
<213> ORGANISM: Candida tropicalis

<400> SEQUENCE: 44
tcgtggcgtg actcccct 18

<210> SEQ ID NO 45
<211> LENGTH: 18
<212> TYPE: DNA
<213> ORGANISM: Candida tropicalis

<400> SEQUENCE: 45
tcttggcgtg attccccg 18

<210> SEQ ID NO 46
<211> LENGTH: 18
<212> TYPE: DNA
<213> ORGANISM: Candida tropicalis

<400> SEQUENCE: 46
gcctggcgtg attccccg 18

<210> SEQ ID NO 47
<211> LENGTH: 16
<212> TYPE: DNA
<213> ORGANISM: Candida tropicalis

<400> SEQUENCE: 47
ccggtgctgg tgtcgt 16

<210> SEQ ID NO 48
<211> LENGTH: 16
<212> TYPE: DNA
<213> ORGANISM: Candida tropicalis

<400> SEQUENCE: 48
ccggtgctgg tgtcat 16

<210> SEQ ID NO 49
<211> LENGTH: 16
<212> TYPE: DNA
<213> ORGANISM: Candida tropicalis

<400> SEQUENCE: 49
ccggtgctgg tgtcat 16

<210> SEQ ID NO 50
<211> LENGTH: 19
<212> TYPE: DNA
<213> ORGANISM: Candida tropicalis

<400> SEQUENCE: 50
ttggcaccca tggttgggg 19

<210> SEQ ID NO 51
<211> LENGTH: 19
<212> TYPE: DNA
<213> ORGANISM: Candida tropicalis

<400> SEQUENCE: 51
ttggcaccca tggctgtgg 19

<210> SEQ ID NO 52
<211> LENGTH: 19
<212> TYPE: DNA
<213> ORGANISM: Candida tropicalis

<400> SEQUENCE: 52
ttggcaccca tgcctgtgg 19

<210> SEQ ID NO 53
<211> LENGTH: 26
<212> TYPE: DNA
<213> ORGANISM: Candida tropicalis -continued

<400> SEQUENCE: 53
ccgaattcga catggctcca tttttg 26

<210> SEQ ID NO 54
<211> LENGTH: 30
<212> TYPE: DNA
<213> ORGANISM: Candida tropicalis

<400> SEQUENCE: 54
ccggatccat tactacaact tggccttggt 30

<210> SEQ ID NO 55
<211> LENGTH: 26
<212> TYPE: DNA
<213> ORGANISM: Candida tropicalis

<400> SEQUENCE: 55
ccagtgaatt cagatgaata ccttct 26

<210> SEQ ID NO 56
<211> LENGTH: 26
<212> TYPE: DNA
<213> ORGANISM: Candida tropicalis

<400> SEQUENCE: 56
ccggatcccc gtctcactac aacttg 26

<210> SEQ ID NO 57
<211> LENGTH: 18
<212> TYPE: DNA
<213> ORGANISM: Candida tropicalis

<400> SEQUENCE: 57
atcaacgcca ccccaacc 18

<210> SEQ ID NO 58
<211> LENGTH: 36
<212> TYPE: DNA
<213> ORGANISM: Candida tropicalis

<400> SEQUENCE: 58
ggtttctcca taaacgagta cctgaaaggg tcaacc 36

<210> SEQ ID NO 59
<211> LENGTH: 18
<212> TYPE: DNA
<213> ORGANISM: Candida tropicalis

<400> SEQUENCE: 59
atctgtctag caaaggtc 18

<210> SEQ ID NO 60
<211> LENGTH: 36
<212> TYPE: DNA
<213> ORGANISM: Candida tropicalis

<400> SEQUENCE: 60
ggttgaccct ttcaggtact cgtttatgga gaaacc 36

<210> SEQ ID NO 61
<211> LENGTH: 31
<212> TYPE: DNA
<213> ORGANISM: Candida tropicalis

<400> SEQUENCE: 61
ccttaattaa tgcatactcg gagcatatcg c 31

<210> SEQ ID NO 62
<211> LENGTH: 28
<212> TYPE: DNA
<213> ORGANISM: Candida tropicalis

<400> SEQUENCE: 62
ccttaattaa tgggcggaat caagtgcc 28

<210> SEQ ID NO 63
<211> LENGTH: 30
<212> TYPE: DNA
<213> ORGANISM: Candida tropicalis

<400> SEQUENCE: 63
ccttaattaa tctcaccaag tacgagaacg 30

<210> SEQ ID NO 64
<211> LENGTH: 28
<212> TYPE: DNA
<213> ORGANISM: Candida tropicalis

<400> SEQUENCE: 64
ccttaattaa gacgcaagca caggtgcc 28

<210> SEQ ID NO 65
<211> LENGTH: 29
<212> TYPE: DNA
<213> ORGANISM: Candida tropicalis

<400> SEQUENCE: 65
ccttaattaa agtctccaag ttgaccgac 29

<210> SEQ ID NO 66
<211> LENGTH: 26
<212> TYPE: DNA
<213> ORGANISM: Candida tropicalis

<400> SEQUENCE: 66
aaatggagcc atggtcgtga tgtgtg 26

<210> SEQ ID NO 67
<211> LENGTH: 29
<212> TYPE: DNA
<213> ORGANISM: Candida tropicalis

<400> SEQUENCE: 67
cacatcacga ccatggctcc atttttgcc 29

<210> SEQ ID NO 68
<211> LENGTH: 28
<212> TYPE: DNA
<213> ORGANISM: Candida tropicalis

<400> SEQUENCE: 68
ccttaattaa tgggcggaat caagtgcc 28

<210> SEQ ID NO 69
<211> LENGTH: 29
<212> TYPE: DNA

-continued

```
<213> ORGANISM: Candida tropicalis

<400> SEQUENCE: 69

ccttaattaa agtctccaag ttgaccgac                                          29


<210> SEQ ID NO 70
<211> LENGTH: 26
<212> TYPE: DNA
<213> ORGANISM: Candida tropicalis

<400> SEQUENCE: 70

gaaggtattc atggtcgtga tgtgtg                                             26


<210> SEQ ID NO 71
<211> LENGTH: 29
<212> TYPE: DNA
<213> ORGANISM: Candida tropicalis

<400> SEQUENCE: 71

cacatcacga ccatgaatac cttcttgcc                                          29


<210> SEQ ID NO 72
<211> LENGTH: 28
<212> TYPE: DNA
<213> ORGANISM: Candida tropicalis

<400> SEQUENCE: 72

ccttaattaa gacgcaagca caggtgcc                                           28
```